(12) United States Patent
Sasisekharan et al.

(10) Patent No.: US 9,499,607 B2
(45) Date of Patent: Nov. 22, 2016

(54) ANTI-DENGUE VIRUS ANTIBODIES AND USES THEREOF

(71) Applicant: Massachusetts Institute of Technology, Cambridge, MA (US)

(72) Inventors: Ram Sasisekharan, Cambridge, MA (US); Luke Nathaniel Robinson, Cambridge, MA (US); Kannan Tharakaraman, Arlington, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 0 days.

(21) Appl. No.: 13/951,066

(22) Filed: Jul. 25, 2013

(65) Prior Publication Data

US 2014/0056913 A1 Feb. 27, 2014

Related U.S. Application Data

(60) Provisional application No. 61/780,209, filed on Mar. 13, 2013, provisional application No. 61/680,385, filed on Aug. 7, 2012.

(51) Int. Cl.
*C07K 16/10* (2006.01)
*C12N 7/01* (2006.01)

(52) U.S. Cl.
CPC .......... *C07K 16/10* (2013.01); *C07K 16/1081* (2013.01); *C07K 2317/33* (2013.01); *C07K 2317/34* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,472,509 A | 9/1984 | Gansow et al. | |
| 4,938,948 A | 7/1990 | Ring et al. | |
| 5,021,236 A | 6/1991 | Gries et al. | |
| 5,196,066 A | 3/1993 | Kusuda et al. | |
| 5,500,161 A | 3/1996 | Andrianov et al. | |
| 5,695,390 A | 12/1997 | Mizuno et al. | |
| 5,741,957 A | 4/1998 | Deboer et al. | |
| 5,750,172 A | 5/1998 | Meade et al. | |
| 5,756,687 A | 5/1998 | Denman et al. | |
| 5,827,690 A | 10/1998 | Meade et al. | |
| 8,637,035 B2 | 1/2014 | Wu et al. | |
| 9,212,217 B2 | 12/2015 | Robinson et al. | |
| 2005/0106660 A1 | 5/2005 | Vogt et al. | |
| 2005/0147614 A1 | 7/2005 | Begent et al. | |
| 2006/0058510 A1 | 3/2006 | Skerra et al. | |
| 2006/0088908 A1 | 4/2006 | Skerra et al. | |
| 2007/0134256 A1 | 6/2007 | Lai et al. | |
| 2009/0312190 A1 | 12/2009 | Chinea Santiago et al. | |
| 2010/0285564 A1 | 11/2010 | Skerra et al. | |
| 2010/0317547 A1 | 12/2010 | Gregory et al. | |
| 2011/0008256 A1 | 1/2011 | Lai et al. | |
| 2011/0189226 A1 | 8/2011 | Bouckenooghe et al. | |
| 2011/0212105 A1 | 9/2011 | Huerta Galindo et al. | |
| 2012/0014945 A1 | 1/2012 | Wu et al. | |
| 2012/0039846 A1 | 2/2012 | Foung et al. | |
| 2015/0368321 A1 | 12/2015 | Sasisekharan et al. | |

FOREIGN PATENT DOCUMENTS

| | | |
|---|---|---|
| SG | 173482 A1 | 9/2011 |
| WO | WO-2006/056464 A2 | 6/2006 |
| WO | WO-2010/043977 A2 | 4/2010 |
| WO | WO-2010093335 A1 | 8/2010 |
| WO | WO-2013089647 A1 | 6/2013 |

OTHER PUBLICATIONS

Bedouelle et al., Diversity and junction residues as hotspots of binding energy in an antibody neutralizing the dengue virus, FEBS J, 273:34-46 (2006).
Cockburn et al., Mechanism of Dengue Virus Broad Cross-Neutralization by a Monoclonal Antibody, Structure 20:303-314 (Feb. 8, 2012).
International Search Report for PCT/US13/52062, 6 pages (Feb. 19, 2014).
Supplement to Cockburn et al., Chain A, Crystal Structure of the Dengue Virus Serotype 4 Envelope Protein Domain Lii in Complex with the Variable Domains of Mab 4e11, NCBI 1-3 (Nov. 21, 2013).
Written Opinion for PCT/US13/052062, 9 pages (Feb. 19, 2014).
Guzman et al., Dengue: a continuing global threat, Nature Reviews: Microbiology 8: S7-S16 (2010).
McBride et al., Dengue viral infections; pathogenesis and epidemiology, Microbes and Infection 2:1041-1050 (2000).
Allison, The mode of action of immunological adjuvants, Dev. Biol. Stand., 92:3-11, (1998).
Altschul, et al., Basic local alignment search tool, J. Mol. Biol., 215(3): 403-410 (1990).
Altschul, et al., Gapped BLAST and PSI-BLAST: a new generation of protein database search programs, Nucleic Acids Res. 25:3389-3402, (1997).
Altschul, S.F. and Gish, W., Local Alignment Statistics, Methods in Enzymology, 266(27):460-480 (1996).
Artpradit, C. et al., Recognition of heparan sulfate by clinical strains of dengue virus serotype 1 using recombinant subviral particles, Virus Res., 176(1-2):69-77 (2013).

(Continued)

*Primary Examiner* — Stacy B Chen
(74) *Attorney, Agent, or Firm* — Choate, Hall & Stewart LLP; Brenda Herschbach Jarrell; Cassandra G. Luca

(57) ABSTRACT

The present invention provides, among other things, antibody agents (e.g., antibodies, and/or antigen-binding fragments thereof) that bind to DV epitopes, as well as compositions containing them and methods of designing, providing, formulating, using, identifying and/or characterizing them. In some embodiments, provided antibody agents show significant binding to a plurality of DV serotypes. In some embodiments, provided antibody agents show significant binding to all four DV serotypes. Such antibody agents are useful, for example, in the prophylaxis, treatment, diagnosis, and/or study of DV.

10 Claims, 15 Drawing Sheets

(56) References Cited

OTHER PUBLICATIONS

Baxevanis, et al., Bioinformatics : A Practical Guide to the Analysis of Genes and Proteins, Wiley, (1998).
Cumber et al., Comparative Stabilities in vitro and in vivo of a recombinant mouse antibody FvCys fragment and a bisFvCys conjuigate, J Immunology 149(1):120-126, (1992).
Dosztányi, Z. et al., ANCHOR: web server for predicting protein binding regions in disordered proteins, Bioinformatics, 25(20):2745-6 (2009).
Dowd, K.A. and Pierson, T.C., Antibody-mediated neutralization of flaviviruses: a reductionist view, Virology, 411(2):306-15 (2011).
Genbank Accession No. CAA10343.1, GI:4033567, first referenced Dec. 16, 1998, updated Jun. 12, 1999 (2 pages).
Genbank Accession No. CAA10344.1, GI:4033569, first referenced Dec. 16, 1998, updated Jun. 12, 1999 (3 pages).
Guirakhoo, F. et al., Fusion activity of flaviviruses: comparison of mature and immature (prM-containing) tick-borne encephalitis virions, J. Gen. Virol. 72 ( Pt 6):1323-9 (1991).
Heinz, F.X. et al., Structural changes and functional control of the tick-borne encephalitis virus glycoprotein E by the heterodimeric association with protein prM, Virology, 198(1):109-17 (1994).
Hijikata, M. et al., Equilibrium centrifugation studies of hepatitis C virus: evidence for circulating immune complexes, J. Virol., 67(4):1953-8 (1993).
International Search Report for PCT/US2015/015510, 4 pages (May 28, 2015).
Kimura, Y. et al., Attachment of hepatitis C virus to cultured cells: a novel predictive factor for successful interferon therapy, J. Med. Virol., 56(1):25-32 (1998).
Kohl et al., Designed to be stable: Crystal structure of a consensus ankryrin repeat protein, PNAS, 100(4):1700-1705, (2003).
Kuhn, R.J. et al., Structure of dengue virus: implications for flavivirus organization, maturation, and fusion, Cell, 108(5):717-25 (2002).
Lai, C.Y. et al., Antibodies to envelope glycoprotein of dengue virus during the natural course of infection are predominantly cross-reactive and recognize epitopes containing highly conserved residues at the fusion loop of domain II, J. Virol., 82(13):6631-43 (2008).
Liu et al., Antibody like eptidomimetics as large scale immunodetection probes, Cell Mol Biol (Noisy-le-grand). 49(2):209-16, (2003).
Lok, S.M. et al., Binding of a neutralizing antibody to dengue virus alters the arrangement of surface glycoproteins, Nat. Struct. Mol. Biol., 15(3):312-7 (2008).
Misener, et al., Bioinformatics Methods and Protocols (Methods in Molecular Biology) 132, Humana Press, (1999).
Morita, T. et al., Detection of hepatitis C virus RNA in circulating immune complexes by RT-PCR. Hepatogastroenterology, 43(9):582-5 (1996).
Pack et al., Miniantibodies: Use of Amphipathic Helices to Produce Functional, Flexibly Linked Dimeric Fv Fragments with High Avidity in *Escherichia coli*, Biochemistry 31(6):15791584, (1992).
Perera, R. et al., Closing the door on flaviviruses: entry as a target for antiviral drug design, Antiviral Res., 80(1):11-22 (2008).

Phillips et al., Enhanced antibody response to lipsome-associated protein antigens: preferential stimulation of IgG2a/b production, Vaccine, 10(3)1 51-158, (1992).
Pierson, T.C. et al., Structural insights into the mechanisms of antibody-mediated neutralization of flavivirus infection: implications for vaccine development, Cell Host Microbe., 4(3):229-38 (2008).
Roehrig, J.T. et al., Monoclonal antibody mapping of the envelope glycoprotein of the dengue 2 virus, Jamaica, Virology, 246(2):317-28 (1998).
Sato, K. et al., Demonstration of sugar moiety on the surface of hepatitis C virions recovered from the circulation of infected humans, Virology, 196(1):354-7 (1993).
Skerra A., Engineered protein scaffolds for molecular recognition, J. Mol. Recognit. 13:167-187, (2000).
Skerra A.,Anticalins: a new class of engineered ligand-binding proteins with antibody-like properties, Reviews in Molecular Biotechnology, 74(4):257-275, (2001).
Sukupolvi-Petty, S. et al., Type- and subcomplex-specific neutralizing antibodies against domain III of dengue virus type 2 envelope protein recognize adjacent epitopes, J. Virol., 81(23):12816-26 (2007).
Tharakaraman, K. et al., Redesign of a cross-reactive antibody to dengue virus with broad-spectrum activity and increased in vivo potency, Proc. Natl. Acad. Sci. U S A., 110(17):E1555-64 (2013).
Thullier, P. et al., A recombinant Fab neutralizes dengue virus in vitro, Journal of Biotechnology, 69: 183-190 (1999).
Unkeless et al., Structure and function of human and murine receptors for IgG, Ann. Rev. Immunol., 6:251-281 (1988).
Wahala, W.M. and Silva, A.M., The human antibody response to dengue virus infection, Viruses, 3(12):2374-95 (2011).
Whitehead, S.S. et al., Prospects for a dengue virus vaccine, Nat. Rev. Microbiol., 5(7):51828 (2007).
Written Opinion for PCT/US2015/015510, 8 pages (May 28, 2015).
Yu, I.M. et al., Association of the pr peptides with dengue virus at acidic pH blocks membrane fusion, J. Virol., 83(23):12101-7 (2009).
Bobrovnik, S.A., Determination of antibody affinity by ELISA. Theory, Journal of Biochemical & Biophysical Methods, 57:213-236 (2003).
Friguet, B. et al., Measurements of the true affinity constant in solution of antigen-antibody complexes by enzyme-linked immunosorbent assay, Journal of Immunology Methods, 77(2):305-319 (1985).
Martineau, Pierre, Chapter 41 Affinity Measurements by Competition ELISA, Springer, 657-665 (2010).
Meyers, E. and Miller, W., Optimal alignments in linear space, CABIOS, 4(1):11-17 (1988).
Author Not Known, Definition of Null Mutation, Medical Dictionary, The Free Dictionary, 3 pages, retrieved on Apr. 17, 2015 <http://medical-dictionary.thefreedictionary.com/null+mutation>.
Beltramello, M. et al., The human immune response to Dengue virus is dominated by highly cross-reactive antibodies endowed with neutralizing and enhancing activity, Cell Host. Microbe., 8(3):271-83 (2010).
Extended European Search Report for EP 13827926.0, 13 pages (Apr. 25, 2016).
Setthapramote, C. et al., Human monoclonal antibodies to neutralize all dengue virus serotypes using lymphocytes from patients at acute phase of the secondary infection, Biochem. Biophys. Res. Commun., 423(4):867-72 (2012).

```
                    ┌─────────┐
                    │  Start  │
                    └────┬────┘
                         ▼
              ┌─────────────────────┐
              │ Homology modeling   │
              │ of Fv from sequence │
              └──────────┬──────────┘
                         ▼
        ┌────────────────────────────────┐
        │ Computational docking between  │
        │ Ab and Ag based on shape       │
        │ complementarity and energetics │
        └───────────────┬────────────────┘
                        ▼
   ┌──────────────────────────────────────────┐
   │ Understand the determinants of affinity  │
   │ and specificity from existing Ag-Ab      │
   │ complexes and prune docking decoys from  │
   │ native-like structures                   │
   └────────────────────┬─────────────────────┘
                        ▼
              ┌─────────────────────┐
              │ Validation of the   │
              │ model by Ala-scanning│
              └──────────┬──────────┘
                         ▼
     ┌────────────────────────────────────────┐
     │ Identify serotype-specific structural  │
     │ elements and rationally design single  │
     │ mutations for simultaneous targeting   │
     │ of all four serotypes                  │
     └───────────────────┬────────────────────┘
                         ▼
    ┌─────────────────────────────────────────┐
    │ Determination of Kd values of single    │
    │ mutant antibodies by EDIII-based        │
    │ indirect ELISA and shortlisting         │
    │ mutations with targeted activities      │
    │ for generating optimized antibodies     │
    └─────────────────────────────────────────┘
```

```
                    A                    B              C            D
                 ━━━━━▶              ━━━━━▶          ━━▶         ━━▶
              307                           329
rED3_s1    MCTQ FKL KE AETQHGTVLV Q KY E D DAPCKIPFSSQDEKGVTQNGRLITANPIVT
rED3_s2    MCTQ FKV KE AETQHGTMVI Q YE G D DSPCKIPFEIMDLEKKHVLGRLITVNPIVI
rED3_s3    MCTN FVL KE SETQHGTILI V YK G D DAPCKIPFSTEDGQGKAHNGRLITANPVVT
rED3_s4    MCSQ FSI KE AETQHGTTVV V KY E A GAPCKVPIEIRDVNKEKVVGRIISSTPLAE

E          F                  G
                 ━━━▶       ━━▶              ━━━━━▶
           361 364                     385 388 390
rED3_s1    KEK VNIEAEPPFGESYIVVGAGE KA KL N FK
rED3_s2    KDS INIEAEPPFGDSYIIIGVEP GQ KL N FK
rED3_s3    KEE VNIEAEPPFGESNIVIGIGD NA KI N YK
rED3_s4    NSV TNIELEPPFGDSYIVIGVGN SA TL N FR
```

(B)

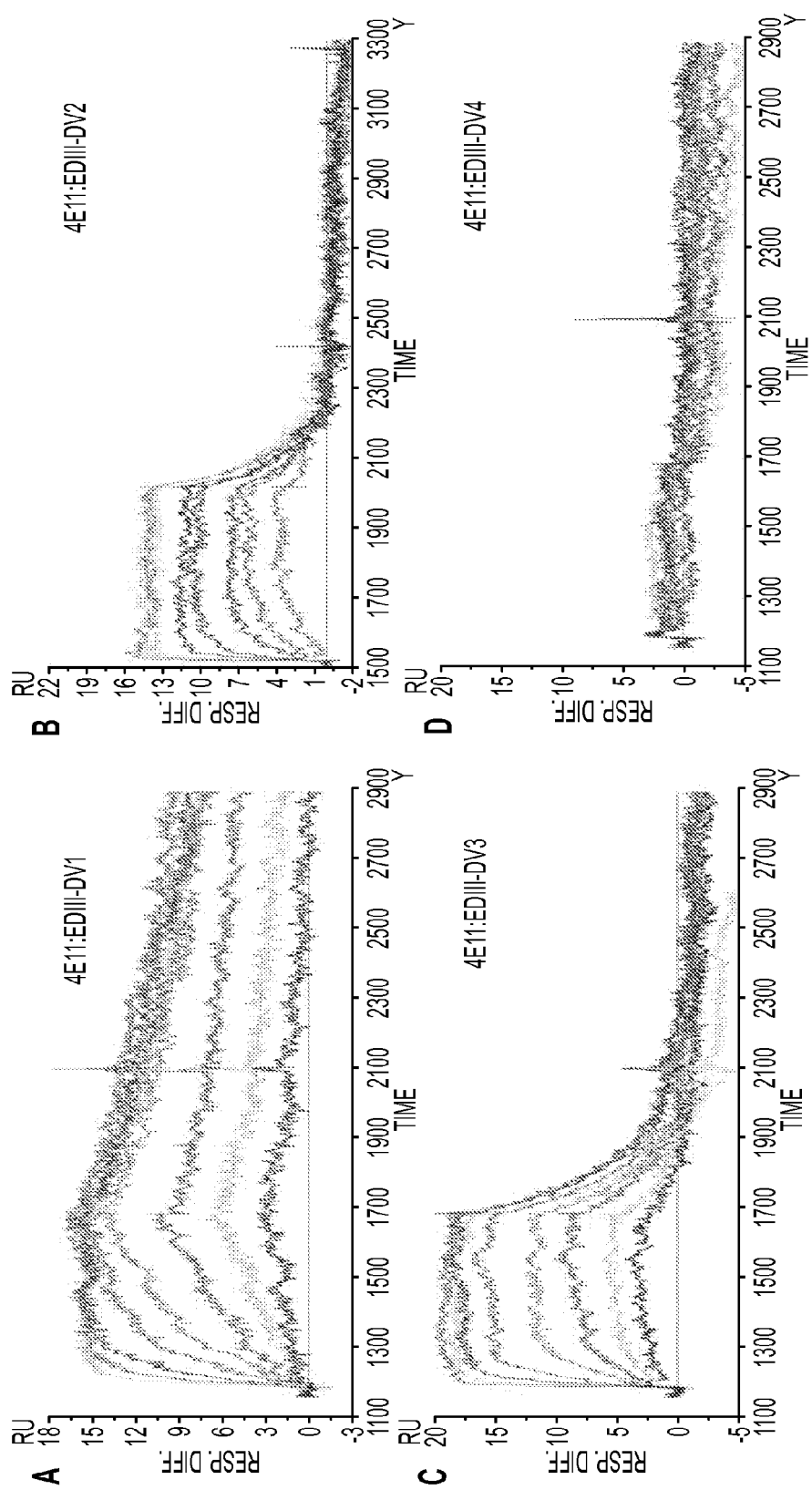
FIG. 8A-D

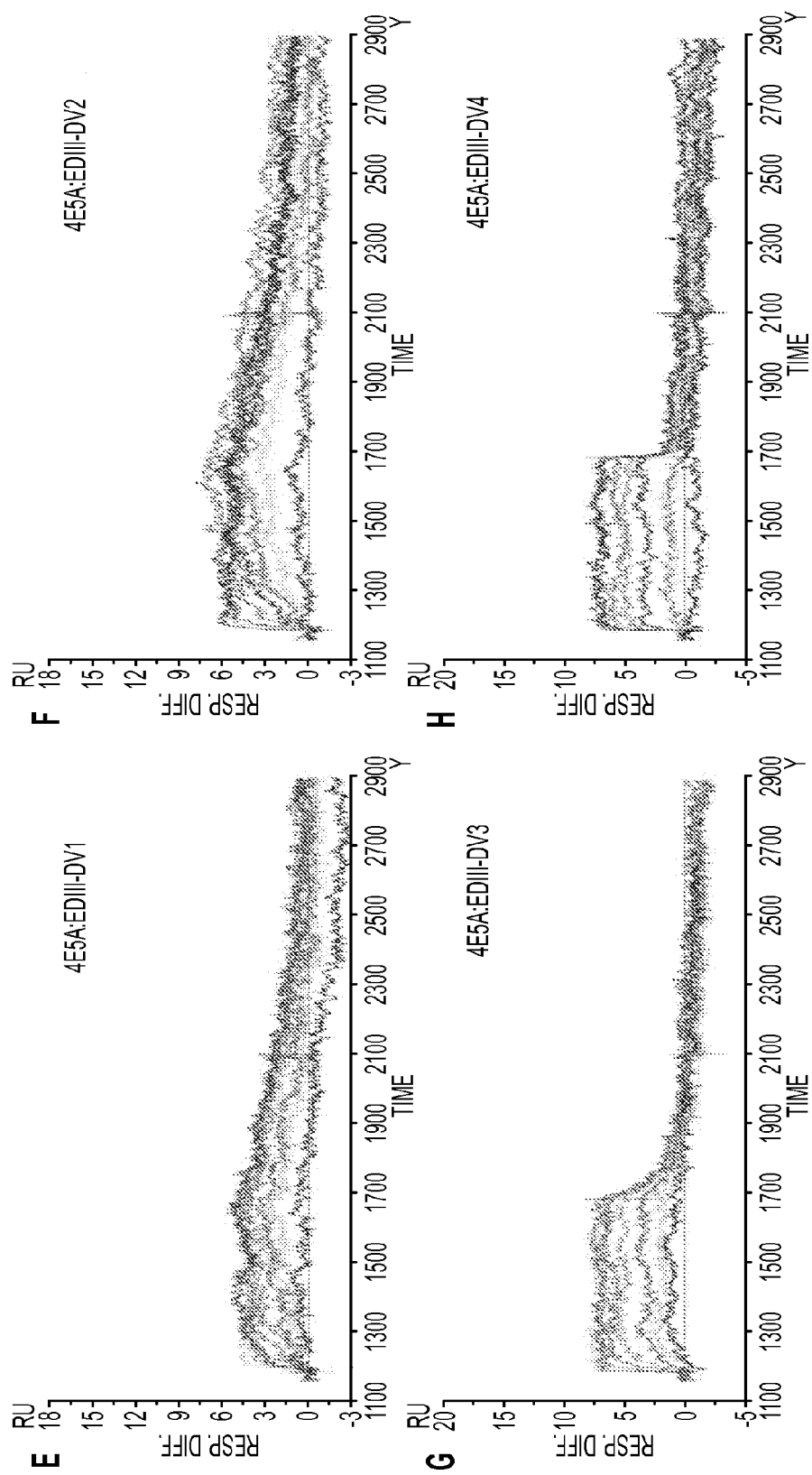
FIG. 8E-H

```
                        SEQUENCE LISTING

<160> NUMBER OF SEQ ID NOS: 28

<210> SEQ ID NO 1
<211> LENGTH: 117
<212> TYPE: PRT
<213> ORGANISM: Artificial Sequence
<220> FEATURE:
<223> OTHER INFORMATION: wt 4E11 HC

<400> SEQUENCE: 1

Glu Val Lys Leu Leu Glu Gln Ser Gly Ala Glu Leu Val Lys Pro Gly
1               5                   10                  15

Ala Ser Val Arg Leu Ser Cys Thr Ala Ser Gly Phe Asn Ile Lys Asp
            20                  25                  30

Thr Tyr Met Ser Trp Val Lys Gln Arg Pro Glu Gln Gly Leu Glu Trp
        35                  40                  45

Ile Gly Arg Ile Asp Pro Ala Asn Gly Asp Thr Lys Tyr Asp Pro Lys
    50                  55                  60

Phe Gln Gly Lys Ala Thr Ile Thr Ala Asp Thr Ser Ser Asn Thr Ala
65                  70                  75                  80

Tyr Leu His Leu Ser Ser Leu Thr Ser Gly Asp Thr Ala Val Tyr Tyr
                85                  90                  95

Cys Ser Arg Gly Trp Glu Gly Phe Ala Tyr Trp Gly Gln Gly Thr Leu
```

```
                100                 105                 110
Val Thr Val Ser Ala
            115

<210> SEQ ID NO 2
<211> LENGTH: 112
<212> TYPE: PRT
<213> ORGANISM: Artificial Sequence
<220> FEATURE:
<223> OTHER INFORMATION: wt 4E11 LC

<400> SEQUENCE: 2

Glu Leu Val Met Thr Gln Thr Pro Ala Ser Leu Ala Val Ser Leu Gly
1               5                   10                  15

Gln Arg Ala Thr Ile Ser Cys Arg Ala Ser Glu Asn Val Asp Arg Tyr
            20                  25                  30

Gly Asn Ser Phe Met His Trp Tyr Gln Gln Lys Ala Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Phe Cys Gln Arg Ser Asn
                85                  90                  95

Glu Val Pro Trp Thr Phe Gly Gly Gly Thr Lys Leu Glu Ile Lys Arg
            100                 105                 110

<210> SEQ ID NO 3
<211> LENGTH: 26
<212> TYPE: PRT
<213> ORGANISM: Artificial Sequence
<220> FEATURE:
<223> OTHER INFORMATION: wt 4E11 HC FR1

<400> SEQUENCE: 3

Glu Val Lys Leu Leu Glu Gln Ser Gly Ala Glu Leu Val Lys Pro Gly
1               5                   10                  15

Ala Ser Val Arg Leu Ser Cys Thr Ala Ser
            20                  25

<210> SEQ ID NO 4
<211> LENGTH: 19
<212> TYPE: PRT
<213> ORGANISM: Artificial Sequence
<220> FEATURE:
<223> OTHER INFORMATION: wt 4E11 HC FR2

<400> SEQUENCE: 4

Tyr Met Ser Trp Val Lys Gln Arg Pro Glu Gln Gly Leu Glu Trp Ile
1               5                   10                  15

Gly Arg Ile

<210> SEQ ID NO 5
<211> LENGTH: 41
<212> TYPE: PRT
<213> ORGANISM: Artificial Sequence
<220> FEATURE:
<223> OTHER INFORMATION: wt 4E11 HC FR3

<400> SEQUENCE: 5

Thr Lys Tyr Asp Pro Lys Phe Gln Gly Lys Ala Thr Ile Thr Ala Asp
1               5                   10                  15
```

Thr Ser Ser Asn Thr Ala Tyr Leu His Leu Ser Ser Leu Thr Ser Gly
            20                  25                  30

Asp Thr Ala Val Tyr Tyr Cys Ser Arg
        35                  40

<210> SEQ ID NO 6
<211> LENGTH: 11
<212> TYPE: PRT
<213> ORGANISM: Artificial Sequence
<220> FEATURE:
<223> OTHER INFORMATION: wt 4E11 HC FR4

<400> SEQUENCE: 6

Trp Gly Gln Gly Thr Leu Val Thr Val Ser Ala
1               5                   10

<210> SEQ ID NO 7
<211> LENGTH: 7
<212> TYPE: PRT
<213> ORGANISM: Artificial Sequence
<220> FEATURE:
<223> OTHER INFORMATION: wt 4E11 HC CDR1

<400> SEQUENCE: 7

Gly Phe Asn Ile Lys Asp Thr
1               5

<210> SEQ ID NO 8
<211> LENGTH: 6
<212> TYPE: PRT
<213> ORGANISM: Artificial Sequence
<220> FEATURE:
<223> OTHER INFORMATION: wt 4E11 HC CDR2

<400> SEQUENCE: 8

Asp Pro Ala Asn Gly Asp
1               5

<210> SEQ ID NO 9
<211> LENGTH: 7
<212> TYPE: PRT
<213> ORGANISM: Artificial Sequence
<220> FEATURE:
<223> OTHER INFORMATION: wt 4E11 HC CDR3

<400> SEQUENCE: 9

Gly Trp Glu Gly Phe Ala Tyr
1               5

<210> SEQ ID NO 10
<211> LENGTH: 23
<212> TYPE: PRT
<213> ORGANISM: Artificial Sequence
<220> FEATURE:
<223> OTHER INFORMATION: wt 4E11 LC FR1

<400> SEQUENCE: 10

Glu Leu Val Met Thr Gln Thr Pro Ala Ser Leu Ala Val Ser Leu Gly
1               5                   10                  15

Gln Arg Ala Thr Ile Ser Cys
            20

<210> SEQ ID NO 11
<211> LENGTH: 15
<212> TYPE: PRT

<213> ORGANISM: Artificial Sequence
<220> FEATURE:
<223> OTHER INFORMATION: wt 4E11 LC FR2

<400> SEQUENCE: 11

Trp Tyr Gln Gln Lys Ala Gly Gln Pro Pro Lys Leu Leu Ile Tyr
1               5                   10                  15

<210> SEQ ID NO 12
<211> LENGTH: 32
<212> TYPE: PRT
<213> ORGANISM: Artificial Sequence
<220> FEATURE:
<223> OTHER INFORMATION: wt 4E11 LC FR3

<400> SEQUENCE: 12

Gly Ile Pro Ala Arg Phe Ser Gly Ser Gly Ser Arg Thr Asp Phe Thr
1               5                   10                  15

Leu Thr Ile Asn Pro Val Glu Ala Asp Asp Val Ala Thr Tyr Phe Cys
            20                  25                  30

<210> SEQ ID NO 13
<211> LENGTH: 11
<212> TYPE: PRT
<213> ORGANISM: Artificial Sequence
<220> FEATURE:
<223> OTHER INFORMATION: wt 4E11 LC FR4

<400> SEQUENCE: 13

Phe Gly Gly Gly Thr Lys Leu Glu Ile Lys Arg
1               5                   10

<210> SEQ ID NO 14
<211> LENGTH: 15
<212> TYPE: PRT
<213> ORGANISM: Artificial Sequence
<220> FEATURE:
<223> OTHER INFORMATION: wt 4E11 LC CDR1

<400> SEQUENCE: 14

Arg Ala Ser Glu Asn Val Asp Arg Tyr Gly Asn Ser Phe Met His
1               5                   10                  15

<210> SEQ ID NO 15
<211> LENGTH: 7
<212> TYPE: PRT
<213> ORGANISM: Artificial Sequence
<220> FEATURE:
<223> OTHER INFORMATION: wt 4E11 LC CDR2

<400> SEQUENCE: 15

Arg Ala Ser Asn Leu Glu Ser
1               5

<210> SEQ ID NO 16
<211> LENGTH: 9
<212> TYPE: PRT
<213> ORGANISM: artificial
<220> FEATURE:
<223> OTHER INFORMATION: wt 4E11 LC CDR3

<400> SEQUENCE: 16

Gln Arg Ser Asn Glu Val Pro Trp Thr
1               5

<210> SEQ ID NO 17

```
<211> LENGTH: 93
<212> TYPE: PRT
<213> ORGANISM: Dengue virus type 1

<400> SEQUENCE: 17

Met Cys Thr Gly Ser Phe Lys Leu Glu Lys Glu Val Ala Glu Thr Gln
1               5                   10                  15

His Gly Thr Val Leu Val Gln Val Lys Tyr Glu Gly Thr Asp Ala Pro
            20                  25                  30

Cys Lys Ile Pro Phe Ser Ser Gln Asp Glu Lys Gly Val Thr Gln Asn
        35                  40                  45

Gly Arg Leu Ile Thr Ala Asn Pro Ile Val Thr Asp Lys Glu Lys Pro
    50                  55                  60

Val Asn Ile Glu Ala Glu Pro Pro Phe Gly Glu Ser Tyr Ile Val Val
65                  70                  75                  80

Gly Ala Gly Glu Lys Ala Leu Lys Leu Ser Trp Phe Lys
                85                  90

<210> SEQ ID NO 18
<211> LENGTH: 93
<212> TYPE: PRT
<213> ORGANISM: Dengue virus type 2

<400> SEQUENCE: 18

Met Cys Thr Gly Lys Phe Lys Val Val Lys Glu Ile Ala Glu Thr Gln
1               5                   10                  15

His Gly Thr Met Val Ile Arg Val Gln Tyr Glu Gly Asp Asp Ser Pro
            20                  25                  30

Cys Lys Ile Pro Phe Glu Ile Met Asp Leu Glu Lys Lys His Val Leu
        35                  40                  45

Gly Arg Leu Ile Thr Val Asn Pro Ile Val Ile Glu Lys Asp Ser Pro
    50                  55                  60

Ile Asn Ile Glu Ala Glu Pro Pro Phe Gly Asp Ser Tyr Ile Ile Ile
65                  70                  75                  80

Gly Val Glu Pro Gly Gln Leu Lys Leu Asn Trp Phe Lys
                85                  90

<210> SEQ ID NO 19
<211> LENGTH: 93
<212> TYPE: PRT
<213> ORGANISM: Dengue virus type 3

<400> SEQUENCE: 19

Met Cys Thr Asn Thr Phe Val Leu Lys Lys Glu Val Ser Glu Thr Gln
1               5                   10                  15

His Gly Thr Ile Leu Ile Lys Val Glu Tyr Lys Gly Glu Asp Ala Pro
            20                  25                  30

Cys Lys Ile Pro Phe Ser Thr Glu Asp Gly Gln Gly Lys Ala His Asn
        35                  40                  45

Gly Arg Leu Ile Thr Ala Asn Pro Val Val Thr Lys Lys Glu Glu Pro
    50                  55                  60

Val Asn Ile Glu Ala Glu Pro Pro Phe Gly Glu Ser Asn Ile Val Ile
65                  70                  75                  80

Gly Ile Gly Asp Asn Ala Leu Lys Ile Asn Trp Tyr Lys
                85                  90

<210> SEQ ID NO 20
<211> LENGTH: 93
```

```
<212> TYPE: PRT
<213> ORGANISM: Dengue virus type 4

<400> SEQUENCE: 20

Met Cys Ser Gly Lys Phe Ser Ile Asp Lys Glu Met Ala Glu Thr Gln
1               5                   10                  15

His Gly Thr Thr Val Val Lys Val Lys Tyr Glu Gly Ala Gly Ala Pro
            20                  25                  30

Cys Lys Val Pro Ile Glu Ile Arg Asp Val Asn Lys Glu Lys Val Val
        35                  40                  45

Gly Arg Ile Ile Ser Ser Thr Pro Leu Ala Glu Asn Thr Asn Ser Val
50                  55                  60

Thr Asn Ile Glu Leu Glu Pro Pro Phe Gly Asp Ser Tyr Ile Val Ile
65                  70                  75                  80

Gly Val Gly Asn Ser Ala Leu Thr Leu His Trp Phe Arg
                85                  90

<210> SEQ ID NO 21
<211> LENGTH: 117
<212> TYPE: PRT
<213> ORGANISM: Artificial Sequence
<220> FEATURE:
<223> OTHER INFORMATION: HC of provided antibody agents

<400> SEQUENCE: 21

Glu Val Lys Leu Leu Glu Gln Ser Gly Ala Glu Leu Val Lys Pro Gly
1               5                   10                  15

Ala Ser Val Arg Leu Ser Cys Thr Ala Ser Gly Phe Asn Ile Lys Asp
            20                  25                  30

Thr Tyr Met Ser Trp Val Lys Gln Arg Pro Glu Gln Gly Leu Glu Trp
        35                  40                  45

Ile Gly Arg Ile Asp Pro Glu Asn Gly Asp Thr Lys Tyr Asp Pro Lys
50                  55                  60

Phe Gln Gly Lys Ala Thr Ile Thr Ala Asp Thr Ser Ser Asn Thr Ala
65                  70                  75                  80

Tyr Leu His Leu Ser Ser Leu Thr Ser Gly Asp Thr Ala Val Tyr Tyr
                85                  90                  95

Cys Ser Arg Gly Trp Glu Gly Phe Ala Tyr Trp Gly Gln Gly Thr Leu
            100                 105                 110

Val Thr Val Ser Ala
        115

<210> SEQ ID NO 22
<211> LENGTH: 112
<212> TYPE: PRT
<213> ORGANISM: Artificial Sequence
<220> FEATURE:
<223> OTHER INFORMATION: LC of provided antibody agents

<400> SEQUENCE: 22

Glu Leu Val Met Thr Gln Thr Pro Ala Ser Leu Ala Val Ser Leu Gly
1               5                   10                  15

Gln Arg Ala Thr Ile Ser Cys Arg Ala Ser Glu Asn Val Asp Lys Tyr
            20                  25                  30

Gly Asn Ser Phe Met His Trp Tyr Gln Gln Lys Ala Gly Gln Pro Pro
        35                  40                  45

Lys Leu Leu Ile Tyr Arg Ala Ser Glu Leu Gln Trp Gly Ile Pro Ala
50                  55                  60
```

```
Arg Phe Ser Gly Ser Gly Ser Arg Thr Asp Phe Thr Leu Thr Ile Asn
 65                  70                  75                  80

Pro Val Glu Ala Asp Asp Val Ala Thr Tyr Phe Cys Gln Arg Ser Asn
                 85                  90                  95

Glu Val Pro Trp Thr Phe Gly Gly Gly Thr Lys Leu Glu Ile Lys Arg
            100                 105                 110

<210> SEQ ID NO 23
<211> LENGTH: 7
<212> TYPE: PRT
<213> ORGANISM: Artificial Sequence
<220> FEATURE:
<223> OTHER INFORMATION: HC CDR1 of provided antibody agents

<400> SEQUENCE: 23

Gly Phe Asn Ile Lys Asp Thr
1               5

<210> SEQ ID NO 24
<211> LENGTH: 6
<212> TYPE: PRT
<213> ORGANISM: Artificial Sequence
<220> FEATURE:
<223> OTHER INFORMATION: HC CDR2 of provided antibody agents

<400> SEQUENCE: 24

Asp Pro Glu Asn Gly Asp
1               5

<210> SEQ ID NO 25
<211> LENGTH: 7
<212> TYPE: PRT
<213> ORGANISM: artificial
<220> FEATURE:
<223> OTHER INFORMATION: HC CDR3 of provided antibody agents

<400> SEQUENCE: 25

Gly Trp Glu Gly Phe Ala Tyr
1               5

<210> SEQ ID NO 26
<211> LENGTH: 15
<212> TYPE: PRT
<213> ORGANISM: Artificial Sequence
<220> FEATURE:
<223> OTHER INFORMATION: LC CDR1 of provided antibody agents

<400> SEQUENCE: 26

Arg Ala Ser Glu Asn Val Asp Lys Tyr Gly Asn Ser Phe Met His
1               5                   10                  15

<210> SEQ ID NO 27
<211> LENGTH: 7
<212> TYPE: PRT
<213> ORGANISM: Artificial Sequence
<220> FEATURE:
<223> OTHER INFORMATION: LC CDR2 of provided antibody agents

<400> SEQUENCE: 27

Arg Ala Ser Glu Leu Gln Trp
1               5

<210> SEQ ID NO 28
<211> LENGTH: 9
<212> TYPE: PRT
<213> ORGANISM: Artificial Sequence
```

```
<220> FEATURE:
<223> OTHER INFORMATION: LC CDR3 of provided antibody agents

<400> SEQUENCE: 28

Gln Arg Ser Asn Glu Val Pro Trp Thr
1               5
```

ANTI-DENGUE VIRUS ANTIBODIES AND USES THEREOF

CROSS-REFERENCE TO RELATED APPLICATIONS

This application claims the benefit under 35 U.S.C. §119 (e) of U.S. Provisional Application No. 61/680,385, filed Aug. 7, 2012, and U.S. Provisional Application No. 61/780,209, filed Mar. 13, 2013, the contents of each which are incorporated herein by reference in their entirety.

GOVERNMENT SUPPORT

This invention was made with government support under grant number R37 GM057073 awarded by the National Institutes of Health. The government has certain rights in the invention.

SEQUENCE LISTING

The present specification makes reference to a Sequence Listing (submitted electronically as a .txt file named "Sequence Listing.txt" on Jul. 25, 2013). The .txt file was generated on Jul. 22, 2013 and is 12.6 kb in size. The entire contents of the Sequence Listing are herein incorporated by reference.

BACKGROUND

Dengue virus (DV) is a member of the virus family Falviviridae and is transmitted to people by several species of mosquito within the genus *Aedes*, principally *Aedes aegypti*. Over 3.6 billion people worldwide are at risk of being infected with DV and more than 200 million infections of DV are estimated to occur each year globally (McBride et al., 2000 Microbes & Infection 2:1041-1050, Guzman et al., 2010 Nature Rev. Microbiol. 8:S7-16). Dengue Fever is the most medically relevant arboviral disease in humans. The significant increases in incidence, geographical outreach, and severity of disease cases of Dengue are making DV a major human pathogen. Unfortunately, effective therapeutic regimens are not currently available; the most effective current prevention measures lie in mosquito control.

SUMMARY

The present invention provides methods and compositions for the treatment and/or prevention of DV infection. Among other things, the present invention provides antibody agents that neutralize all four DV serotypes. In some embodiments, provided antibody agents are variants of reference antibody 4E11; in some such embodiments, provided antibody agents have amino acid sequences that show high overall sequence identity with that of 4E11, or a relevant fragment thereof, yet include specific sequence variations as compared with 4E11 and show a significant improvement in neutralization of at least one DV serotype as compared with that observed for 4E11.

The present invention provides the insight that reference antibody 4E11, has certain desirable attributes, including binding to all four DV serotypes and having potent neutralizing ability of three of the four DV serotypes, but also lacks the ability to effectively neutralize the fourth DV serotype. The present invention identifies the source of the problem of 4E11's inability to effectively neutralize this fourth DV serotype. In particular, the present invention defines structural feature modifications that improve the ability of an antibody agent whose sequence contains the modification(s) to neutralize the relevant DV serotype, as compared with the ability of 4E11, which lacks the modifications. The present invention therefore defines and provides antibodies having structures that include the relevant structural feature modifications (but may otherwise be substantially identical to that of 4E11) and being characterized by an ability to neutralize DV serotype 4 (DV4). In some embodiments, provided antibody agents show abilities to neutralize each of the other three DV serotypes that are not significantly reduced as compared that of 4E11. Indeed, in some embodiments, provided antibody agents are characterized by a surprising increase in neutralization capability with respect to one or more of the other three DV serotypes (DV1-4) as compared with that observed with 4E11.

The present invention provides technologies for defining structural modifications that impart biological activities of interest to polypeptides, while maintaining structural features required to preserve other activities.

In some embodiments, the present invention provides antibody agents that bind to DV epitopes, as well as compositions containing them and methods of designing, providing, formulating, using, identifying and/or characterizing them. In some embodiments, provided antibody agents show significant binding to a plurality of DV serotypes. In some embodiments, provided antibody agents show significant binding to all four DV serotypes. Provided antibody agents are useful, for example, in the prophylaxis, treatment, diagnosis, and/or study of DV.

In some embodiments, provided antibody agents cross-compete with one or more previously-described reference anti-DV antibodies. In some embodiments, provided antibody agents bind to an epitope that is or comprises an amino acid sequence within SEQ ID NO. 17 (EDIII-DV1), SEQ ID NO. 18 (EDIII-DV2), SEQ ID NO. 19 (EDIII-DV3), SEQ ID NO. 20 (EDIII-DV4) and/or combinations thereof. In some embodiments, provided antibody agents do not significantly cross-compete with one or more particular previously-described anti-DV antibodies.

In some embodiments, provided antibody agents neutralize DV in established model systems with greater potency than does one or more previously-described reference anti-DV antibodies. The present invention encompasses, among other things, the recognition that provided antibody agents may offer greater therapeutic and/or prophylactic benefit than do previously-described anti-DV antibodies.

Provided antibody agents are useful in a variety of contexts including, for example, in therapeutic, prophylactic, diagnostic, and/or research applications. In some embodiments, provided antibody agents are useful in the treatment of chronic and/or acute DV infection, for example by administering to a subject suffering from or susceptible to such infection a therapeutically effective amount of one or more provided such provided antibody agents. In some embodiments, a therapeutically effective amount is an amount sufficient to achieve one or more particular biological effects, including, but not limited to, (i) reducing severity or frequency of, and/or delaying onset or re-emergence of one or more symptoms or characteristics of DV infection in an individual susceptible to or suffering from DV infection; and/or (ii) reducing risk of infection and/or of development of one or more symptoms or characteristics of DV infection in an individual exposed or at risk of exposure to DV infection. In some embodiments, the one or more symptoms or characteristics of DV infection is or comprises high fever and at least one or more additional symptoms selected for example from severe headache, severe eye pain, joint pain, muscle pain, bone pain, rash, mild bleeding manifestation (e.g., nose or gum bleeding, petechiae, easy bruising), abdominal pain, vomiting, black, tarry stools, drowsiness or irritability, pale, cold or clammy skin, difficulty breathing, low white cell count, circulating viral particles in an individual or one or more tissues (e.g., blood, bone marrow) or organs (e.g., liver) thereof. In some embodiments, an individual suffering from DV infection displays high fever and at least two such additional symptoms.

In some embodiments, provided antibody agents may be used to prevent, reduce recurrence of, and/or delay onset of one or more symptoms or characteristics of DV infection. In some embodiments, provided antibody agents may be used, for example, for passive immunization of individuals recently exposed to DV or at risk of being exposed to DV, newborn babies born to DV-positive mothers, and/or liver transplantation patients (e.g., to prevent possible recurrent DV infections in such patients).

In some embodiments, the present invention provides viral mimic agents whose structure includes one or more conserved elements of certain DV antigens, for example sufficient to permit the viral mimic agent to mimic one or more biological activities of the relevant DV antigen. In some embodiments, such viral mimic agents include such conserved structural elements of DV antigens, for example as defined herein, and lack one or more other structural elements of the DV antigens. In some embodiments, provided viral mimic agents are or comprise one or more polypeptides. In some embodiments, provided viral mimic agent polypeptides have amino acid sequences that include one or more conserved sequence elements from a DV antigen; in some embodiments, provided viral mimic agent polypeptides lack one or more other sequence elements from the DV antigen. For example, in some embodiments, provided viral mimic agent polypeptides are or comprise fragments of a DV antigen.

In some embodiments, the present invention provides therapeutic methods of treatment, utilized after development of one or more symptoms of DV infection. In some embodiments, the present invention provides therapeutic methods of prophylaxis, utilized prior to development of one or more symptoms of DV infection, and/or prior to exposure to DV, DV infection, or risk thereof. In some particular embodiments, the present invention provides passive immunization technologies.

In some embodiments, the present invention provides diagnostic methods of detecting DV in and/or otherwise characterizing samples such as clinical, environmental, and/or research samples.

The present invention provides systems for designing, identifying, and/or characterizing useful anti-DV antibody agents. For example, in some embodiments, the present invention provides empirical computational approaches that capture particular physicochemical features common to protein interfaces. In some embodiments, such approaches permit prediction of protein-protein interactions (e.g., antigen-antibody interactions), including for example predicting which amino acid sequences might show particularly high interaction affinity. In some embodiments, provided approaches are usefully applied to design, identify, and/or characterize sequences that differ from a reference sequence and show one or more improved characteristics (e.g., improved affinity) with regard to their protein-protein interactions.

The present invention provides systems for stratifying patients based on their immunological response to DV. The present invention provides methods for identifying those patients likely to respond well to DV immunotherapy. For example, a patient's serum may be used to test for the presence of antibodies directed against a particular epitope of DV (e.g., epitope to which provided antibody agents specifically binds). If the patient does not have adequate levels of antibodies directed to such an epitope, one or more provided DV antibody agents may be administered to the patient. The patient's own immune response may be supplemented with provided DV antibody agents. In some embodiments, immunotherapy aids in clearance of DV virus and/or resolution of DV infection. In some embodiments, immunotherapy in accordance with the present invention treats and/or prevents chronic DV infection.

In some embodiments, the present invention provides methods of designing, identifying and/or characterizing useful antibody agents. For example, in some embodiments, such methods involve determining whether a test antibody agent competes for antigen binding with one or more reference anti-DV antibodies and/or other antibody agents. In some embodiments, a test antibody agent is identified as a useful antibody agent if it cross-competes with one or more reference DV antibodies.

In some embodiments, provided antibody agents are combined with one or more additional pharmaceutically acceptable substances to provide pharmaceutical compositions. The present invention provides pharmaceutical compositions for treatment, prevention, diagnosis and/or characterization of DV infection.

In some embodiments, pharmaceutical compositions comprise antibody agents that are or comprise, for example, human antibodies or fragments or variants thereof that bind to any DV serotype and neutralize DV infection in vitro. In some embodiments, pharmaceutical compositions comprise antibody agents that are or comprise, for example human antibodies or fragments or variants thereof that bind to any DV serotype and neutralize DV infection in vivo. In some embodiments, DV neutralization by provided antibody agents in in vitro systems is correlative and/or predictive of DV neutralization by provided antibody agents in vivo (e.g., in humans and/or other mammals).

In some embodiments, provided antibody agents may be utilized together with one or more other therapies for treating, reducing incidence, frequency, or severity of, and/or delaying onset of DV infection or one or more symptoms or characteristics thereof. For example, in some embodiments, provided antibody agents are utilized together with one or more anti-viral agents, anti-inflammatories, pain relievers, immunomodulating therapeutics and combination therapy, which preferably involves other DV targets. For example, in some embodiments, in some embodiments, provided antibody agents are administered in combination with one or more interferons (e.g., interferon $\alpha$-2b, interferon-$\gamma$, etc.), analgesics (preferably containing acetaminophen and not aspirin and/or ibuprofen), anti-DV monoclonal antibodies, anti-DV polyclonal antibodies, RNA polymerase inhibitors, protease inhibitors, nucleoside analogs, helicase inhibitors, immunomodulators, antisense compounds, short interfering RNAs (siRNAs), short hairpin RNAs (shRNAs), micro RNAs (miRNAs), RNA aptamers, ribozymes, and combinations thereof.

Thus, in some embodiments, the invention specifically provides an antibody agent which binds to and neutralizes each of Dengue Virus serotypes D1, D2, D3, and D4. In some embodiments, the antibody agent binds to an epitope that is or comprises an amino acid sequence within: SEQ ID NO. 17 (EDIII-DV1), SEQ ID NO. 18 (EDIII-DV2), SEQ ID NO. 19 (EDIII-DV3), SEQ ID NO. 20 (EDIII-DV4), or combinations thereof. In some embodiments, the antibody agent binds to an epitope in the A-strand region of envelop glycoprotein of Dengue virus.

In some embodiments, the epitope comprises on or more residues corresponding to that at a position selected from the group consisting of 305, 306, 307, 308, 309, 310, 311, 312, 323, 325, 327, 329, 360, 361, 362, 363, 364, 385, 387, 388, 389, 390, 391, and combinations thereof, of any one of SEQ ID NOs. 17-20. In some embodiments, the corresponding residue at position 305 is selected from the group consisting of: serine, lysine, and threonine. In some embodiments, the corresponding residue at position 310 is lysine. In some embodiments, the corresponding residue at position 311 is lysine. In some embodiments, the corresponding residue at position 323 is selected from the group consisting of arginine, lysine, and glutamine. In some embodiments, the corresponding residue at position 327 is selected from the group consisting of lysine and glutamate. In some embodiments, the corresponding residue at position 329 is selected from the group consisting of arginine, aspartate, glutamate, and threonine.

In some embodiments, the invention provides an antibody agent whose heavy chain variable region and/or light chain variable region includes at least one complementarity determining region (CDR) sharing at least 80% sequence identity with a CDR of reference antibody 4E11, but differs by substitution of at least one amino residue within the CDR. In some embodiments, the antibody agent includes at least one CDR that is substantially identical to a reference CDR of antibody 4E11 in that it is either identical to such reference CDR or includes between 1-5 substitutions of amino acids within such reference CDR. In some embodiments, the reference CDR is selected from the group consisting of one found between residues 27 and 33 of the 4E11 heavy chain (SEQ ID NO. 1), one found between residues 53 and 58 of the 4E11 heavy chain (SEQ ID NO. 1), one found between residues 100 and 106 of the 4E11 heavy chain (SEQ ID NO. 1), one found between residues 24 and 38 of the 4E11 light chain (SEQ ID NO. 2), one found between residues 54 and 60 of the 4E11 light chain (SEQ ID NO. 2), one found between residues 93 and 101 of the 4E11 light chain (SEQ ID NO. 2); and combinations thereof. In some embodiments, the antibody agent includes at least one CDR that is substantially identical to a reference CDR set forth below, in that it is either identical to such reference CDR or includes between 1-5 substitutions of amino acids within such reference CDR reference CDRs: GFNIKDT (SEQ ID NO. 7), DPANGD (SEQ ID NO. 8), GWEGFAY (SEQ ID NO. 9), RASENVDKYGNSFMH (SEQ ID NO. 14), RASNLES (SEQ ID NO. 15), and/or QRSNEVPWT (SEQ ID NO. 16). In some embodiments, the reference CDR is a heavy chain CDR. In some embodiments, the reference CDR is a light chain CDR. In some embodiments, the antibody agent includes at least one heavy chain CDR that is substantially identical to a heavy chain reference CDR and also includes at least one light chain CDR that is identical to a light chain reference CDR. In some embodiments, each of the CDRs in the antibody agent is substantially identical to one of the reference CDRs.

In some embodiments, the invention provides an antibody agent whose heavy chain variable region includes at least one complementarity determining region (CDR) sharing at least 95% sequence identity with a CDR of reference antibody 4E11, but differs by substitution of at least one amino acid residue within the CDR. In some embodiments, the antibody agent includes at least one CDR that is substantially identical to a reference CDR of antibody 4E11 in that it is either identical to such reference CDR or includes between 1-5 substitutions of amino acids within such reference CDR. In some embodiments, the reference CDR is selected from the group consisting of one found between residues 27 and 33 of the 4E11 heavy chain (SEQ ID NO. 1), one found between residues 53 and 58 of the 4E11 heavy chain (SEQ ID NO. 1), one found between residues 100 and 106 of the 4E11 heavy chain (SEQ ID NO. 1), one found between residues 24 and 38 of the 4E11 light chain (SEQ ID NO. 2), one found between residues 54 and 60 of the 4E11 light chain (SEQ ID NO. 2), one found between residues 93 and 101 of the 4E11 light chain (SEQ ID NO. 2), and combinations thereof. In some embodiments, the antibody agent includes at least one CDR that is substantially identical to a reference CDR set forth below, in that it is either identical to such reference CDR or includes between 1-5 substitutions of amino acids within such reference CDR reference CDRs: GFNIKDT (SEQ ID NO. 7), DPANGD (SEQ ID NO. 8), GWEGFAY (SEQ ID NO. 9), RASENVDKYGNSFMH (SEQ ID NO. 14), RASNLES (SEQ ID NO. 15), and/or QRSNEVPWT (SEQ ID NO. 16). In some embodiments, the reference CDR is a heavy chain CDR. In some embodiments, the reference CDR is a light chain CDR. In some embodiments, the antibody agent includes at least one heavy chain CDR that is substantially identical to a heavy chain reference CDR and also includes at least one light chain CDR that is identical to a light chain reference CDR. In some embodiments, each of the CDRs in the antibody agent is substantially identical to one of the reference CDRs. In some embodiments, the heavy chain variable region CDR has substitution of the amino acid residue at position 55. In some embodiments, the substitute amino acid at position 55 is selected form the group consisting of glutamate and aspartate. In some embodiments, the light chain variable region CDR has substitution of the amino acid residue at positions selected from the group consisting of 31, 57, 59, 60, and combinations thereof. In some embodiments, the substitute amino acid residue at position 31 is lysine. In some embodiments, the substitute amino acid residue at position 57 is selected from the group consisting of glutamate and serine. In some embodiments, the substitute amino acid residue at position 59 is selected from the group consisting of glutamine and asparagine. In some embodiments, the substitute amino acid residue at position 60 is selected from the group consisting of tryptophan, tyrosine, and arginine.

In some embodiments, the invention provides an antibody agent which is an IgG. In some embodiments, an antibody agent is a monoclonal antibody. In some embodiments, an antibody agent is selected from the group consisting of: a mouse antibody, a humanized antibody, a human antibody, a purified antibody, an isolated antibody, a chimeric antibody, a polyclonal antibody, and combinations thereof. In some embodiments, an antibody agent is provided wherein the antigen binding fragment is selected from the group consisting of: a Fab fragment, a Fab' fragment, a F(ab')$_2$ fragment, a Fd fragment, a Fd' fragment, a Fv fragment, a dAb fragment, a scFv fragment, an isolated CDR region, a dsFv diabody, a single chain antibody, and combinations thereof.

In some embodiments, the invention provides a cell line expressing an antibody agent specific to Dengue virus, wherein the antibody agent binds to and neutralizes each of Dengue Virus serotypes D1, D2, D3, and D4. In some embodiments, the invention provides a pharmaceutical composition including one or more antibody agents wherein the antibody agent binds to and neutralizes each of Dengue Virus serotypes D1, D2, D3, and D4 and a pharmaceutically acceptable excipient. In some embodiments, a pharmaceutical composition further includes at least one additional antiviral agent.

In some embodiments, the invention provides methods of treating a subject in need thereof, including the step of administering an antibody agent wherein the antibody agent binds to and neutralizes each of Dengue Virus serotypes D1, D2, D3, and D4. In some embodiments, the invention provides kits including at least one antibody agent wherein the antibody agent binds to and neutralizes each of Dengue Virus serotypes D1, D2, D3, and D4, a syringe, needle, or applicator for administration of the at least one antibody or fragment to a subject, and instructions for use.

In some embodiments, the invention provides methods of manufacturing pharmaceutical compositions, the method including the steps of providing an antibody agent wherein the antibody agent binds to and neutralizes each of Dengue Virus serotypes D1, D2, D3, and D4, and formulating the antibody agent with at least one pharmaceutically acceptable carrier, so that a pharmaceutical composition is generated. In some embodiments, the pharmaceutical composition is a liquid composition. In some embodiments, the pharmaceutical composition is formulated for parenteral administration. In some embodiments, the pharmaceutical composition is formulated for intravenous administration. In some embodiments, the pharmaceutical composition is formulated for intravenous administration to a child.

BRIEF DESCRIPTION OF THE DRAWING

The Figures of the Drawing are for illustration purposes only, not for limitation.

FIG. 4 shows a flowchart of the antibody design approach.

FIGS. 6A-B illustrate sequence and structural determinants of poor DV4 binding. (A) Sequence alignment of EDIII domain region of four serotypes: EDIII-DV1 (rED3_s1, SEQ ID NO. 17), EDIII-DV2 (rED3_s2, SEQ ID NO. 18), EDIII-DV3 (rED3_s3, SEQ ID NO. 19), and EDIII-DV4 (rED3_s4, SEQ ID NO. 20). Putative mAb binding residues are shaded in grey. Residues at 307, 329, 361, 364, 385, 388 and 390 differentiate DV4 from reminder of the sequences; these are numbered. Residue contacts made by the five mAb mutations are boxed. Notably, 5 out of 6 new contacts are formed against conserved epitope residues of A & B strands. This explains why the new mutations are not detrimental to DV1-3 binding. (B) Structural model of 4E11/EDIII interaction. Sequence positions that discriminate DV4 from other strains are labeled and the side chains of amino acids therein represented as sticks.

FIG. 7 demonstrates that affinity-enhancing mutations localize to the periphery of the 4E11:EDIII-DV4 interface. The positive positions identified in the binding screen are highlighted and shown in a structural model of 4E11:EDIII-DV4 interaction. All positive mutations are located at the periphery of the binding interface. The two panels represent different views of the same model. EDIII (top), VH (right), and VL (left) proteins are represented respectively, in each panel.

FIGS. 8A-H show surface plasmon resonance (SPR) sensograms of 4E11 WT and 4E5A with antigens EDIII of DV1-4.

FIG. 9 illustrates in vitro neutralizing activity of antibodies assessed by focus reduction neutralization test (FRNT). Neutralization assays were performed with DV1-4 and antibodies 4E11 WT, m4E11 WT, 4E5A, and 4G2. Serial dilutions of antibody were mixed with equal amounts of virus and added to Vero cell monolayers with a viscous overlay. After 4-6 days, cells were fixed and foci were immunostained and counted. Data points represent averages of duplicates with error bars representing standard deviation. A standard four-parameter logistic model was fit to the data using least squares regression. 4E5A shows similar neutralizing activity to 4E11 and m4E11 for DV1-3 and a substantial increase in neutralizing activity to DV4. 4G2, a representative flavivirus fusion-loop specific antibody, demonstrates lower neutralizing activity for DV1-3 and only slightly higher activity to DV4 relative to 4E5A.

FIG. 10 shows in vivo prophylactic DV2 challenge model. The data show virus in the serum of AF129 mice on day 3 after virus challenge. Mice treated with AB1 or placebo 1 day prior to virus challenge. RNA extracted from the serum of the mice was amplified by QRT-PCR and an approximate $Log_{10}CCID_{50}$ titer was extrapolated based on a curve from control RNA taken from a sample of known titer. The dashed line represents the approximate limit of detection.

FIG. 11 demonstrates amino acid frequencies in paratope and epitope. Data generated from 77 antigen-antibody complexes.

DEFINITIONS

In order for the present invention to be more readily understood, certain terms are first defined below; those of ordinary skill in the art will appreciate and understand the use and scope of these terms as defined below and/or otherwise used herein.

Figure 1:
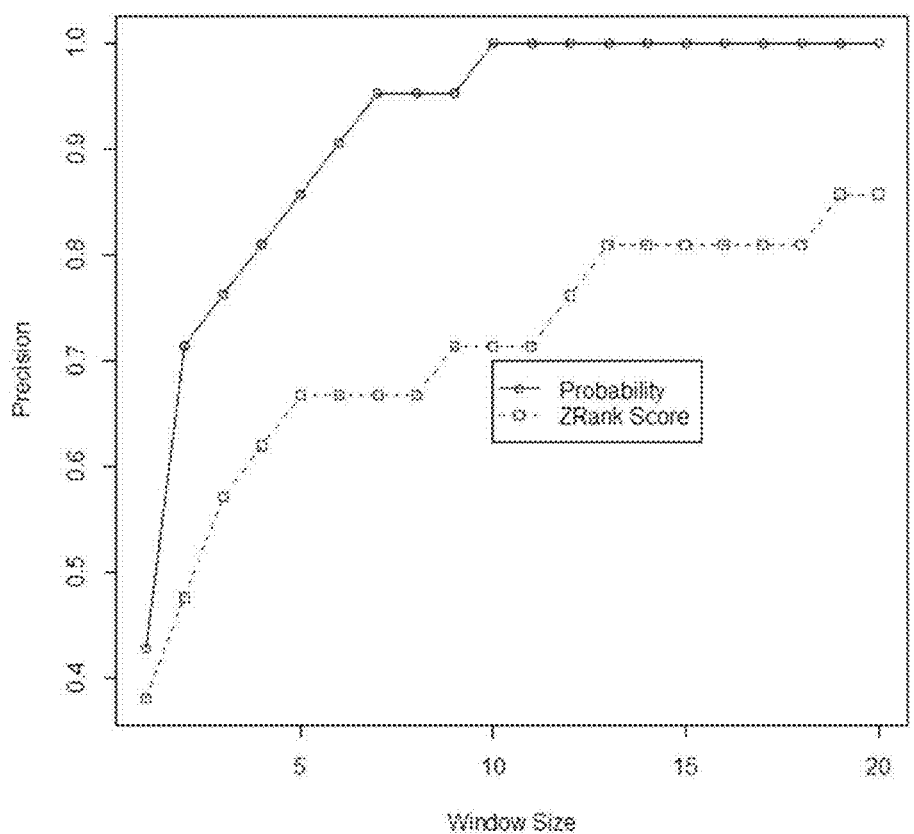
FIG. 1 shows the effect of window size on prediction accuracy. The window size represents the number of predicted positives. Prediction accuracy is determined by the number of test case structures (overall 37) correctly predicted. When the window size is one (i.e., when one out of 101 structures is predicted to be positive), nearly half of the x-ray structures (48%~18 out of 37) were correctly identified, the binomial probability of which is 1.46E-26 (n=37, p=0.009, number of successes=18) if the structures were chosen at random. The prediction accuracy of MLR-method is seen to be a logarithmically increasing function of window size with accuracy reaching 85% at window size 5 and 100% at window size 10. On the contrary, ZRANK fails to predict 100% of the structures even when the window size is 20.

Adult: As used herein, the term "adult" refers to a human eighteen years of age or older. Body weights among adults can vary widely with a typical range being 90 pounds to 250 pounds.

Affinity: As is known in the art, "affinity" is a measure of the tightness with a particular ligand (e.g., an antibody) binds to its partner (e.g., an epitope). Affinities can be measured in different ways.

Amino acid: As used herein, term "amino acid," in its broadest sense, refers to any compound and/or substance that can be incorporated into a polypeptide chain. In some embodiments, an amino acid has the general structure $H_2N-C(H)(R)-COOH$. In some embodiments, an amino acid is a naturally occurring amino acid. In some embodiments, an amino acid is a synthetic amino acid; in some embodiments, an amino acid is a d-amino acid; in some embodiments, an amino acid is an l-amino acid. "Standard amino acid" refers to any of the twenty standard l-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Animal: As used herein, the term "animal" refers to any member of the animal kingdom. In some embodiments, "animal" refers to humans, of either sex and at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In certain embodiments, the animal is susceptible to infection by DV. In some embodiments, an animal may be a transgenic animal, genetically engineered animal, and/or a clone.

Antibody agent: As used herein, the term "antibody agent" refers to an agent that specifically binds to a particular antigen. In some embodiments, the term encompasses any polypeptide with immunoglobulin structural elements sufficient to confer specific binding. Suitable antibody agents include, but are not limited to, human antibodies, primatized antibodies, chimeric antibodies, bi-specific antibodies, humanized antibodies, conjugated antibodies (i.e., antibodies conjugated or fused to other proteins, radiolabels, cytotoxins), Small Modular ImmunoPharmaceuticals ("SMIPs™"), single chain antibodies, cameloid antibodies, and antibody fragments. As used herein, the term "antibody agent" also includes intact monoclonal antibodies, polyclonal antibodies, single domain antibodies (e.g., shark single domain antibodies (e.g., IgNAR or fragments thereof)), multispecific antibodies (e.g. bi-specific antibodies) formed from at least two intact antibodies, and antibody fragments so long as they exhibit the desired biological activity. In some embodiments, the term encompasses stapled peptides. In some embodiments, the term encompasses one or more antibody-like binding peptidomimetics. In some embodiments, the term encompasses one or more antibody-like binding scaffold proteins. In come embodiments, the term encompasses monobodies or adnectins. In many embodiments, an antibody agent is or comprises a polypeptide whose amino acid sequence includes one or more structural elements recognized by those skilled in the art as a complementarity determining region (CDR); in some embodiments an antibody agent is or comprises a polypeptide whose amino acid sequence includes at least one CDR (e.g., at least one heavy chain CDR and/or at least one light chain CDR) that is substantially identical to one found in a reference antibody. In some embodiments an included CDR is substantially identical to a reference CDR in that it is either identical in sequence or contains between 1-5 amino acid substitutions as compared with the reference CDR. In some embodiments an included CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR. In some embodiments an included CDR is substantially identical to a reference CDR in that it shows at least 96%, 96%, 97%, 98%, 99%, or 100% sequence identity with the reference CDR. In some embodiments an included CDR is substantially identical to a reference CDR in that at least one amino acid within the included CDR is deleted, added, or substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments an included CDR is substantially identical to a reference CDR in that at least one amino acid within the included CDR is substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an antibody agent is or comprises a polypeptide whose amino acid sequence includes structural elements recognized by those skilled in the art as an immunoglobulin variable domain. In some embodiments, an antibody agent is a polypeptide protein having a binding domain which is homologous or largely homologous to an immunoglobulin-binding domain Antibody: As is known in the art, an "antibody" is an immunoglobulin that binds specifically to a particular antigen. The term encompasses immunoglobulins that are naturally produced in that they are generated by an organism reacting to the antigen, and also those that are synthetically produced or engineered. An antibody may be monoclonal or polyclonal. An antibody may be a member of any immunoglobulin class, including any of the human classes: IgG, IgM, IgA, and IgD. A typical immunoglobulin (antibody) structural unit as understood in the art, is known to comprise a tetramer. Each tetramer is composed of two identical pairs of polypeptide chains, each pair having one "light" (approximately 25 kD) and one "heavy" chain (approximately 50-70 kD). The N-terminus of each chain defines a variable region of about 100 to 110 or more amino acids primarily responsible for antigen recognition. The terms "variable light chain" (VL) and "variable heavy chain" (VH) refer to these light and heavy chains respectively. Each variable region is further subdivided into hypervariable (HV) and framework (FR) regions. The hypervariable regions comprise three areas of hypervariability sequence called complementarity determining regions (CDR 1, CDR 2 and CDR 3), separated by four framework regions (FR1, FR2, FR2, and FR4) which form a beta-sheet structure and serve as a scaffold to hold the HV regions in position. The C-terminus of each heavy and light chain defines a constant region consisting of one domain for the light chain (CL) and three for the heavy chain (CH1, CH2 and CH3). In some embodiments, the term "full length" is used in reference to an antibody to mean that it contains two heavy chains and two light chains, optionally associated by disulfide bonds as occurs with naturally-produced antibodies. In some embodiments, an antibody is produced by a cell. In some embodiments, an antibody is produced by chemical synthesis. In some embodiments, an antibody is derived from a mammal. In some embodiments, an antibody is derived from an animal such as, but not limited to, mouse, rat, horse, pig, or goat. In some embodiments, an antibody is produced using a recombinant cell culture system. In some embodiments, an antibody may be a purified antibody (for example, by immune-affinity chromatography). In some embodiments, an antibody may be a human antibody. In some embodiments, an antibody may be a humanized antibody (antibody from non-human species whose protein sequences have been modified to increase their similarity to antibody variants produced naturally in humans). In some embodiments, an antibody may be a chimeric antibody (antibody made by combining genetic material from a non-human source, e.g., mouse, rat, horse, or pig, with genetic material from humans).

Antibody fragment: As used herein, an "antibody fragment" includes a portion of an intact antibody, such as, for example, the antigen-binding or variable region of an antibody. Examples of antibody fragments include Fab, Fab', F(ab')2, and Fv fragments; triabodies; tetrabodies; linear antibodies; single-chain antibody molecules; and multi specific antibodies formed from antibody fragments. For example, antibody fragments include isolated fragments, "Fv" fragments, consisting of the variable regions of the heavy and light chains, recombinant single chain polypeptide molecules in which light and heavy chain variable regions are connected by a peptide linker ("ScFv proteins"), and minimal recognition units consisting of the amino acid residues that mimic the hypervariable region. In many embodiments, an antibody fragment contains sufficient sequence of the parent antibody of which it is a fragment that it binds to the same antigen as does the parent antibody; in some embodiments, a fragment binds to the antigen with a comparable affinity to that of the parent antibody and/or competes with the parent antibody for binding to the antigen. Examples of antigen binding fragments of an antibody include, but are not limited to, Fab fragment, Fab' fragment, F(ab')2 fragment, scFv fragment, Fv fragment, dsFv diabody, dAb fragment, Fd' fragment, Fd fragment, and an isolated complementarity determining region (CDR) region. An antigen binding fragment of an antibody may be produced by any means. For example, an antigen binding fragment of an antibody may be enzymatically or chemically produced by fragmentation of an intact antibody and/or it may be recombinantly produced from a gene encoding the partial antibody sequence. Alternatively or additionally, antigen binding fragment of an antibody may be wholly or partially synthetically produced. An antigen binding fragment of an antibody may optionally comprise a single chain antibody fragment. Alternatively or additionally, an antigen binding fragment of an antibody may comprise multiple chains which are linked together, for example, by disulfide linkages. An antigen binding fragment of an antibody may optionally comprise a multimolecular complex. A functional antibody fragment typically comprises at least about 50 amino acids and more typically comprises at least about 200 amino acids.

Antiviral agent: As used herein, the term "antiviral agent" refers to a class of medication used specifically for treating viral infections by inhibiting, deactivating, or destroying virus particles. In general, an antiviral agent may be or comprise a compound of any chemical class (e.g., a small molecule, metal, nucleic acid, polypeptide, lipid and/or carbohydrate). In some embodiments, an antiviral agent is or comprises an antibody or antibody mimic. In some embodiments, an antiviral agent is or comprises a nucleic acid agent (e.g., an antisense oligonucleotide, a siRNA, a shRNA, etc) or mimic thereof. In some embodiments, an antiviral agent is or comprises a small molecule. In some embodiments, an antiviral agent is or comprises a naturally-occurring compound (e.g., small molecule). In some embodiments, an antiviral agent has a chemical structure that is generated and/or modified by the hand of man.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Baby: As used herein, the term "baby" refers to a human under two years of age. Typical body weights for a baby rages from 3 pounds up to 20 pounds.

Biologically active: As used herein, the phrase "biologically active" refers to a characteristic of any substance that has activity in a biological system (e.g., cell culture, organism, etc.). For instance, a substance that, when administered to an organism, has a biological effect on that organism, is considered to be biologically active. In particular embodiments, where a protein or polypeptide is biologically active, a portion of that protein or polypeptide that shares at least one biological activity of the protein or polypeptide is typically referred to as a "biologically active" portion.

Characteristic portion: As used herein, the term "characteristic portion" is used, in the broadest sense, to refer to a portion of a substance whose presence (or absence) correlates with presence (or absence) of a particular feature, attribute, or activity of the substance. In some embodiments, a characteristic portion of a substance is a portion that is found in the substance and in related substances that share the particular feature, attribute or activity, but not in those that do not share the particular feature, attribute or activity. In certain embodiments, a characteristic portion shares at least one functional characteristic with the intact substance. For example, in some embodiments, a "characteristic portion" of a protein or polypeptide is one that contains a continuous stretch of amino acids, or a collection of continuous stretches of amino acids, that together are characteristic of a protein or polypeptide. In some embodiments, each such continuous stretch generally contains at least 2, 5, 10, 15, 20, 50, or more amino acids. In general, a characteristic portion of a substance (e.g., of a protein, antibody, etc.) is one that, in addition to the sequence and/or structural identity specified above, shares at least one functional characteristic with the relevant intact substance. In some embodiments, a characteristic portion may be biologically active.

Child: As used herein, the term "child" refers to a human between two and 18 years of age. Body weight can vary widely across ages and specific children, with a typical range being 30 pounds to 150 pounds.

Combination therapy: The term "combination therapy", as used herein, refers to those situations in which two or more different pharmaceutical agents are administered in overlapping regimens so that the subject is simultaneously exposed to both agents.

Comparable: The term "comparable" is used herein to describe two (or more) sets of conditions or circumstances that are sufficiently similar to one another to permit comparison of results obtained or phenomena observed. In some embodiments, comparable sets of conditions or circumstances are characterized by a plurality of substantially identical features and one or a small number of varied features. Those of ordinary skill in the art will appreciate that sets of conditions are comparable to one another when characterized by a sufficient number and type of substantially identical features to warrant a reasonable conclusion that differences in results obtained or phenomena observed under the different sets of conditions or circumstances are caused by or indicative of the variation in those features that are varied.

Corresponding to: As used herein, the term "corresponding to" is often used to designate the position/identity of an amino acid residue in a polypeptide of interest. Those of ordinary skill will appreciate that, for purposes of simplicity, residues in a polypeptide are often designated using a canonical numbering system based on a reference related polypeptide, so that an amino acid "corresponding to" a residue at position 190, for example, need not actually be the $190^{th}$ amino acid in a particular amino acid chain but rather corresponds to the residue found at 190 in the reference polypeptide; those of ordinary skill in the art readily appreciate how to identify "corresponding" amino acids.

Dosage form: As used herein, the terms "dosage form" and "unit dosage form" refer to a physically discrete unit of a therapeutic protein (e.g., antibody) for the patient to be treated. Each unit contains a predetermined quantity of active material calculated to produce the desired therapeutic effect. It will be understood, however, that the total dosage of the composition will be decided by the attending physician within the scope of sound medical judgment.

Dosing regimen: A "dosing regimen" (or "therapeutic regimen"), as that term is used herein, is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount.

DV serotype: As used herein, the term "serotype" generally refers to distinct variations within DVs. The four different DV serotypes (DV1-4) comprising the DV genetic group differ from one another by approximately 25% to 40% at the amino acid level. The four serotypes of DV vary in pathogenicities but all are prevalent in areas of Asia, Africa, Central and South America. Infection with one of these serotypes provides life-long immunity to that serotype however it also increases risk of severe disease upon a secondary infection from a heterologous DV serotype.

Epitope: As used herein, the term "epitope" has its meaning as understood in the art. It will be appreciated by those of ordinary skill in the art that an epitope also known as antigenic determinant, is a molecular region of an antigen that is recognized by the immune system, specifically by antibodies, B cells, or T cells. It will be further appreciated that epitopes can be composed of sugars, lipids, or amino acids. The epitopes of protein antigens are divided into two categories, conformational epitopes and linear epitopes, based on their structure and interaction with the paratope (part of an antibody that recognizes the epitope). A conformational epitope is composed of discontinuous sections of the antigen's amino acid sequence and these epitopes interact with the paratope based on the 3-D surface features and shape or tertiary structure of the antigen. Linear epitopes interact with the paratope based on their primary structure and a linear epitope is formed by a continuous sequence of amino acids from the antigen.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein.

Functional: As used herein, a "functional" biological molecule is a biological molecule in a form in which it exhibits a property and/or activity by which it is characterized.

Gene: As used herein, the term "gene" has its meaning as understood in the art. It will be appreciated by those of ordinary skill in the art that the term "gene" may include gene regulatory sequences (e.g., promoters, enhancers, etc.) and/or intron sequences. It will further be appreciated that definitions of gene include references to nucleic acids that do not encode proteins but rather encode functional RNA molecules such as tRNAs, RNAi-inducing agents, etc. For the purpose of clarity we note that, as used in the present application, the term "gene" generally refers to a portion of a nucleic acid that encodes a protein; the term may optionally encompass regulatory sequences, as will be clear from context to those of ordinary skill in the art. This definition is not intended to exclude application of the term "gene" to non-protein-coding expression units but rather to clarify that, in most cases, the term as used in this document refers to a protein-coding nucleic acid.

Gene product or expression product: As used herein, the term "gene product" or "expression product" generally refers to an RNA transcribed from the gene (pre- and/or post-processing) or a polypeptide (pre- and/or post-modification) encoded by an RNA transcribed from the gene.

Homology: As used herein, the term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar.

Identity: As used herein, the term "identity" refers to the overall relatedness between polymeric molecules, e.g., between nucleic acid molecules (e.g., DNA molecules and/or RNA molecules) and/or between polypeptide molecules. Calculation of the percent identity of two nucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4: 11-17), which has been incorporated into the ALIGN program (version 2.0) using a PAM 120 weight residue table, a gap length penalty of 12 and a gap penalty of 4. The percent identity between two nucleotide sequences can, alternatively, be determined using the GAP program in the GCG software package using an NWSgapdna.CMP matrix.

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.).

Mimotope: As used herein, the term "mimotope" refers to a macromolecule which mimics the structure of an epitope. In some embodiments, a mimotope elicits an antibody response identical or similar to that elicited by its corresponding epitope. In some embodiments, an antibody that recognizes an epitope also recognizes a mimotope which mimics that epitope. In some embodiments, a mimotope is a peptide. In some embodiments, a mimotope is a small molecule, carbohydrate, lipid, or nucleic acid. In some embodiments, mimotopes are peptide or non-peptide mimotopes of conserved DV epitopes. In some embodiments, by mimicking the structure of a defined viral epitope, a mimotope interferes with the ability of DV virus particles to bind to its natural binding partners (e.g., DV target receptor, Rab5, GRP78), e.g., by binding to the natural binding partner itself.

Mutant: As used herein, the term "mutant" refers to an entity that shows significant structural identity with a reference entity but differs structurally from the reference entity in the presence or level of one or more chemical moieties as compared with the reference entity. In many embodiments, a mutant also differs functionally from its reference entity. In general, whether a particular entity is properly considered to be a "mutant" of a reference entity is based on its degree of structural identity with the reference entity. As will be appreciated by those skilled in the art, any biological or chemical reference entity has certain characteristic structural elements. A mutant, by definition, is a distinct chemical entity that shares one or more such characteristic structural elements. To give but a few examples, a small molecule may have a characteristic core structural element (e.g., a macrocycle core) and/or one or more characteristic pendent moieties so that a mutant of the small molecule is one that shares the core structural element and the characteristic pendent moieties but differs in other pendent moieties and/or in types of bonds present (single vs double, E vs Z, etc) within the core, a polypeptide may have a characteristic sequence element comprised of a plurality of amino acids having designated positions relative to one another in linear or three-dimensional space and/or contributing to a particular biological function, a nucleic acid may have a characteristic sequence element comprised of a plurality of nucleotide residues having designated positions relative to on another in linear or three-dimensional space. For example, a mutant polypeptide may differ from a reference polypeptide as a result of one or more differences in amino acid sequence and/or one or more differences in chemical moieties (e.g., carbohydrates, lipids, etc) covalently attached to the polypeptide backbone. In some embodiments, a mutant polypeptide shows an overall sequence identity with a reference polypeptide that is at least 85%, 86%, 87%, 88%, 89%, 90%, 91%, 92%, 93%, 94%, 95%, 96%, 97%, or 99%. Alternatively or additionally, in some embodiments, a mutant polypeptide does not share at least one characteristic sequence element with a reference polypeptide. In some embodiments, the reference polypeptide has one or more biological activities. In some embodiments, a mutant polypeptide shares one or more of the biological activities of the reference polypeptide. In some embodiments, a mutant polypeptide lacks one or more of the biological activities of the reference polypeptide. In some embodiments, a mutant polypeptide shows a reduced level of one or more biological activities as compared with the reference polypeptide.

Nucleic acid: As used herein, the term "nucleic acid," in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. In some embodiments, "nucleic acid" refers to individual nucleic acid residues (e.g., nucleotides and/or nucleosides). In some embodiments, "nucleic acid" refers to an oligonucleotide chain comprising individual nucleic acid residues. As used herein, the terms "oligonucleotide" and "polynucleotide" can be used interchangeably. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e., analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. The term "nucleic acid segment" is used herein to refer to a nucleic acid sequence that is a portion of a longer nucleic acid sequence. In many embodiments, a nucleic acid segment comprises at least 3, 4, 5, 6, 7, 8, 9, 10, or more residues. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present invention is specifically directed to "unmodified nucleic acids," meaning nucleic acids (e.g., polynucleotides and residues, including nucleotides and/or nucleosides) that have not been chemically modified in order to facilitate or achieve delivery.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre and post natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Pharmaceutical composition: As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Polypeptide: As used herein, a "polypeptide", generally speaking, is a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides sometimes include "non-natural" amino acids or other entities that nonetheless are capable of integrating into a polypeptide chain, optionally.

Protein: As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Polypeptides may contain l-amino acids, d-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

Recurrent DV infection: As used herein, a "recurrent DV infection" refers to reemergence of clinical and/or laboratory evidence of infection, e.g., one or more symptoms of infection or the presence of circulating DV particles and/or DV particles in the subject's liver.

Refractory: The term "refractory" as used herein, refers to any subject that does not respond with an expected clinical efficacy following the administration of provided compositions as normally observed by practicing medical personnel.

Serotype: In general, a "serotype" or "serovar" refers to distinct variations within a species of bacteria or viruses or among immune cells of different individuals. These microorganisms are typically classified together based on their cell surface antigens, allowing the epidemiologic classification of organisms to the sub-species level.

Small Molecule: In general, a "small molecule" is a molecule that is less than about 5 kilodaltons (kD) in size. In some embodiments, the small molecule is less than about 4 kD, 3 kD, about 2 kD, or about 1 kD. In some embodiments, the small molecule is less than about 800 daltons (D), about 600 D, about 500 D, about 400 D, about 300 D, about 200 D, or about 100 D. In some embodiments, a small molecule is less than about 2000 g/mol, less than about 1500 g/mol, less than about 1000 g/mol, less than about 800 g/mol, or less than about 500 g/mol. In some embodiments, small molecules are non-polymeric. In some embodiments, in accordance with the present invention, small molecules are not proteins, polypeptides, oligopeptides, peptides, polynucleotides, oligonucleotides, polysaccharides, glycoproteins, proteoglycans, etc.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantial sequence homology: The phrase "substantial homology" is used herein to refer to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains Substitution of one amino acid for another of the same type may often be considered a "homologous" substitution. Typical amino acid categorizations are summarized below:

| Alanine | Ala | A | nonpolar | neutral | 1.8 |
|---|---|---|---|---|---|
| Arginine | Arg | R | polar | positive | −4.5 |
| Asparagine | Asn | N | polar | neutral | −3.5 |
| Aspartic acid | Asp | D | polar | negative | −3.5 |
| Cysteine | Cys | C | nonpolar | neutral | 2.5 |
| Glutamic acid | Glu | E | polar | negative | −3.5 |
| Glutamine | Gln | Q | polar | neutral | −3.5 |
| Glycine | Gly | G | nonpolar | neutral | −0.4 |
| Histidine | His | H | polar | positive | −3.2 |
| Isoleucine | Ile | I | nonpolar | neutral | 4.5 |
| Leucine | Leu | L | nonpolar | neutral | 3.8 |
| Lysine | Lys | K | polar | positive | −3.9 |
| Methionine | Met | M | nonpolar | neutral | 1.9 |
| Phenylalanine | Phe | F | nonpolar | neutral | 2.8 |
| Proline | Pro | P | nonpolar | neutral | −1.6 |
| Serine | Ser | S | polar | neutral | −0.8 |
| Threonine | Thr | T | polar | neutral | −0.7 |
| Tryptophan | Trp | W | nonpolar | neutral | −0.9 |
| Tyrosine | Tyr | Y | polar | neutral | −1.3 |
| Valine | Val | V | nonpolar | neutral | 4.2 |

| Ambiguous Amino Acids | 3-Letter | 1-Letter |
|---|---|---|
| Asparagine or aspartic acid | Asx | B |
| Glutamine or glutamic acid | Glx | Z |
| Leucine or Isoleucine | Xle | J |
| Unspecified or unknown amino acid | Xaa | X |

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul, et al., "Gapped BLAST and PSI-BLAST: a new generation of protein database search programs", *Nucleic Acids Res.* 25:3389-3402, 1997; Baxevanis, et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999; all of the foregoing of which are incorporated herein by reference. In addition to identifying homologous sequences, the programs mentioned above typically provide an indication of the degree of homology. In some embodiments, two sequences are considered to be substantially homologous if at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or more of their corresponding residues are homologous over a relevant stretch of residues. In some embodiments, the relevant stretch is a complete sequence. In some embodiments, the relevant stretch is at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 225, at least 250, at least 275, at least 300, at least 325, at least 350, at least 375, at least 400, at least 425, at least 450, at least 475, at least 500 or more residues.

Substantial identity: The phrase "substantial identity" is used herein to refer to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul et al., *Nucleic Acids Res.* 25:3389-3402, 1997; Baxevanis et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Suffering from: An individual who is "suffering from" a disease, disorder, or condition (e.g., DV) has been diagnosed with and/or exhibits one or more symptoms of the disease, disorder, or condition. DV infection is frequently asymptomatic. In some embodiments, an individual who is suffering from DV has been exposed to and/or infected with DV, but does not display any symptoms of DV infection and/or has not been diagnosed with DV infection. In some embodiments, an individual who is suffering from DV is an individual who has one or more DV particles in his/her blood.

Susceptible to: An individual who is "susceptible to" a disease, disorder, or condition (e.g., DV) is at risk for developing the disease, disorder, or condition. In some embodiments, an individual who is susceptible to a disease, disorder, or condition does not display any symptoms of the disease, disorder, or condition. In some embodiments, an individual who is susceptible to a disease, disorder, or condition has not been diagnosed with the disease, disorder, and/or condition. In some embodiments, an individual who is susceptible to a disease, disorder, or condition is an individual who has been exposed to conditions associated with development of the disease, disorder, or condition (e.g., the individual has been exposed to DV). In some embodiments, a risk of developing a disease, disorder, and/or condition is a population-based risk (e.g., intravenous drug users; recipients of donated blood, blood products, and organs prior to 1992, when such products began to be screened; healthcare workers handling needles; babies born to DV-infected mothers; etc.).

Symptoms are reduced: According to the present invention, "symptoms are reduced" when one or more symptoms of a particular disease, disorder or condition is reduced in magnitude (e.g., intensity, severity, etc.) or frequency. For purposes of clarity, a delay in the onset of a particular symptom is considered one form of reducing the frequency of that symptom. To give but a few examples, exemplary symptoms of DV include, but are not limited to, sudden onset of fever, high fever (often over 40° C.), muscle and joint pains, headache, vomiting, diarrhea, occurrence of a rash as flushed skin or measles-like rash, petechiae (small red spots caused by broken capillaries that do not disappear when skin is pressed), bleeding from the mucous membranes, low white blood cell count, low platelets, metabolic acidosis, elevated level of aminotransferase from the liver, plasma leakage resulting in hemoconcentration (indicated by a rising hematocrit) and hypoalbuminemia, fluid accumulation in the chest and abdominal cavity (e.g., pleural effusion or ascites), gastrointestinal bleeding, shock and hemorrhage, positive tourniquet test, hypotension, infection of the brain or heart, impairment of vital organs (e.g., liver), neurological disorders such as transverse myelitis, and/or combinations thereof. It is not intended that the present invention be limited only to cases where the symptoms are eliminated. The present invention specifically contemplates treatment such that one or more symptoms is/are reduced (and the condition of the subject is thereby "improved"), albeit not completely eliminated.

Therapeutic agent: As used herein, the phrase "therapeutic agent" refers to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, etc. In some embodiments, a therapeutic agent is any substance that can be used to alleviate, ameliorate, relieve, inhibit, prevent, delay onset of, reduce severity of, and/or reduce incidence of one or more symptoms or features of a disease, disorder, and/or condition.

Therapeutically effective amount: As used herein, the term "therapeutically effective amount" refers to an amount of a therapeutic protein which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of a therapeutic protein or composition effective to treat, ameliorate, or prevent a desired disease or condition, or to exhibit a detectable therapeutic or preventative effect, such as by ameliorating symptoms associated with the disease, preventing or delaying the onset of the disease, and/or also lessening the severity or frequency of symptoms of the disease. A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific fusion protein employed; the duration of the treatment; and like factors as is well known in the medical arts.

Treatment: As used herein, the term "treatment" (also "treat" or "treating") refers to any administration of a substance (e.g., provided compositions) that partially or completely alleviates, ameliorates, relives, inhibits, delays onset of, reduces severity of, and/or reduces incidence of one or more symptoms, features, and/or causes of a particular disease, disorder, and/or condition (e.g., DV). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

Unit dose: The expression "unit dose" as used herein refers to an amount administered as a single dose and/or in a physically discrete unit of a pharmaceutical composition. In many embodiments, a unit dose contains a predetermined quantity of an active agent. In some embodiments, a unit dose contains an entire single dose of the agent. In some embodiments, more than one unit dose is administered to achieve a total single dose. In some embodiments, administration of multiple unit doses is required, or expected to be required, in order to achieve an intended effect. A unit dose may be, for example, a volume of liquid (e.g., an acceptable carrier) containing a predetermined quantity of one or more therapeutic agents, a predetermined amount of one or more therapeutic agents in solid form, a sustained release formulation or drug delivery device containing a predetermined amount of one or more therapeutic agents, etc. It will be appreciated that a unit dose may be present in a formulation that includes any of a variety of components in addition to the therapeutic agent(s). For example, acceptable carriers (e.g., pharmaceutically acceptable carriers), diluents, stabilizers, buffers, preservatives, etc., may be included as described infra. It will be appreciated by those skilled in the art, in many embodiments, a total appropriate daily dosage of a particular therapeutic agent may comprise a portion, or a plurality, of unit doses, and may be decided, for example, by the attending physician within the scope of sound medical judgment. In some embodiments, the specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts.

Vaccination: As used herein, the term "vaccination" refers to the administration of a composition intended to generate an immune response, for example to a disease-causing agent. For the purposes of the present invention, vaccination can be administered before, during, and/or after exposure to a disease-causing agent, and in certain embodiments, before, during, and/or shortly after exposure to the agent. In some embodiments, vaccination includes multiple administrations, appropriately spaced in time, of a vaccinating composition.

Vector: As used herein, "vector" refers to a nucleic acid molecule capable of transporting another nucleic acid to which it is associated. In some embodiment, vectors are capable of extra-chromosomal replication and/or expression of nucleic acids to which they are linked in a host cell such as a eukaryotic and/or prokaryotic cell. Vectors capable of directing the expression of operatively linked genes are referred to herein as "expression vectors."

Wild-type: As used herein, the term "wild-type" has its art-understood meaning that refers to an entity having a structure and/or activity as found in nature in a "normal" (as contrasted with mutant, diseased, altered, etc) state or context. Those of ordinary skill in the art will appreciate that wild type genes and polypeptides often exist in multiple different forms (e.g., alleles).

DV Nomenclature

It is well known by those skilled in the art that DV nomenclature typically utilizes Roman numerals (e.g., "I," "II," "III," "IV," etc.) that represents DV genotype and a lowercase letter (e.g., "a," "b," etc.) that represents DV subtype. Although the rules of nomenclature are generally accepted in the art, those of ordinary skill in the art recognize that the rules of nomenclature are not always strictly followed in publications, presentations, conversation, etc. Thus, those skilled in the art would recognize that, for example, it is implicit that "DV Ia," "DV genotype Ia," and "DV subtype Ia" could be used interchangeably by one of skill in the art, and that all three terms are intended to refer to DV genotype I, subtype a.

As used herein, Roman numerals (e.g., "I," "II," "III," "IV," etc.) are used to refer to DV genotype, and lowercase letters (e.g., "a," "b," etc.) are used to refer to DV subtypes. It will also be understood that, when DV of a particular genotype is referred to herein, it is meant to encompass all subtypes of the named genotype. To give but one example, "genotype I" is used herein to refer to all subtypes of genotype I (e.g., genotype I, subtype a; genotype I, subtype b; etc.).

As used herein, any Roman numeral (e.g., "I," "II," "III," "IV," etc.) that is present after the genotype and subtype designations will be understood to refer to the DV strain.

DETAILED DESCRIPTION OF CERTAIN EMBODIMENTS

The present invention provides useful anti-DV antibody agents with particular structural and/or functional characteristics, as well as compositions and methods relating to such antibody agents.

Dengue Virus (DV) Infection

DV infection represents a major arthropod-borne viral disease, with over 3.5 billion people living in areas of risk for the disease, and over 200 million infections worldwide, resulting in 21,000 deaths per year. Notably, the annual average number of reported Dengue Virus infections, the geographical spread, and the severity of disease have all increased dramatically in recent years. Dengue Virus epidemics can cause significant morbidity, leading to substantial economic costs and health care impacts (Guzman et al, 2010 Nature Reviews Microbiol. 8:S7-16).

DV infection is caused by any of the four related viruses primarily transmitted by *Aedes aegypti* mosquitoes and is endemic to tropical and sub-tropical regions. Infection in a mammal is initiated by injection of the DV during the blood meal of an infected *Aedes* mosquito, whereby the DV is primarily deposited in the extravascular tissues. The incubation period of DV after a mosquito bite is between 3 to 14 days. Dendritic cells, monocytes, and macrophages are among the first targets of DV. After initial replication in the skin and lymphatic ganglia, DV appears in the blood in the course of the acute febrile stage, generally 3 to 5 days.

Routine laboratory diagnosis of Dengue Virus infection is based on isolation of the DV and/or detection of antibodies specific to DV. Infection can cause several different syndromes, influenced by age and/or immunological status of the infected individual. Primary DV infection may be asymptomatic or may result in Dengue Fever. Dengue Fever is characterized by a high fever that typically has two phases and at least one additional symptom such as headache (often severe), pain (which can be severe) in any of a variety of body parts (e.g., eye, joint, muscle, bone, abdomen), skin eruptions or rash, mild bleeding manifestation (e.g., nose or gum bleeding, petechiae, easy bruising), lymphadenopathy, vomiting, discolored (black) stools, mood effects such as prostration, drowsiness or irritability, skin that is pale, cold, or clammy, difficulty breathing, low white cell count, circulating viral particles in one or more of an organism's tissues (e.g., blood, bone marrow, etc) and/or organs (e.g., liver) (see, for example, Center for Disease Control description; see also US 2011/0189226). Reduced leukocyte and platelet numbers frequently occur.

Dengue Hemorrhagic Fever (DHF) is a potentially deadly complication of DV infection. DHF is characterized by extreme lethargy and drowsiness, coupled with the high fever and other symptoms associated with Dengue Fever. Increased vascular permeability and abnormal homeostasis can lead to a decrease in blood volume, hypotension, and in severe cases, hypovolemic shock and internal bleeding. Two factors that appear to play a major role in the occurrence of hemorrhagic Dengue Fever are: rapid viral replication with a high level of viremia; and a major inflammatory response with the release of high levels of inflammatory mediators. Without treatment, the mortality rate for hemorrhagic Dengue Fever can reach 10%.

Children are particularly susceptible to the effects of DV infection, which can increase dramatically with repeated exposure. During initial Dengue Virus infections, most children experience subclinical infection or mild undifferentiated febrile syndromes. During secondary Dengue Virus infections the pathophysiology of the disease often changes dramatically. Sequential infections can result in an acute vascular permeability syndrome known as Dengue Shock Syndrome (DSS). DSS is usually a progression of DHF and is frequently fatal. DSS is characterized by rapid and poor volume pulse, hypotension, cold extremities, and restlessness. Without medical intervention, the fatality rate for DSS can reach 40-50% (Thullier et al, 1999 Journal of Biotechnology 69:183-190). The severity of DSS is age-dependent, with vascular leakage being most severe in young children.

DV infections in adults are often accompanied by a tendency for bleeding that can lead to severe hemorrhage. DV infections can be life-threatening when they occur in individuals with asthma, diabetes, and/or other chronic diseases (Guzman et al, 2010 Nature Reviews Microbiol. 8:S7-16).

The leading theory proposed to explain the increased risk of severe disease in secondary cases of DV is antibody dependent enhancement (ADE). Dengue Viruses (DVs) display antibody epitopes that are unique to each serotype as well as epitopes that are shared between or among serotypes. A subject has experienced (and recovered from) a primary DV infection may develops robust antibody responses that cross react with all DV serotypes (DV1-4). However, despite the cross reactivity, antibodies only prevent re-infection by the same (homologous) serotype and individuals are susceptible to subsequent infections with different (heterologous) serotypes. Individuals experiencing a secondary Dengue infection with a new serotype face a much greater risk of developing DHF, indicating that pre-existing immunity to DV can exacerbate disease. The ADE theory of DV postulates that weakly neutralizing antibodies from the first infection bind to the second serotype and enhance infection of FcγR bearing myeloid cells such as monocytes and macrophages (Wahala et al., 2011 Viruses 3: 2374-2395).

At least three types of mechanisms have been proposed to explain development of severe forms of DV infection: (i) they may be caused by particularly virulent virus strains; (ii) pre-existing subneutralizing antibodies could enhance the antibody-mediated uptake of DV by monocytes or macrophages, which are designated as host cells of DV (e.g., ADE); and (iii) antibodies directed against a non-structural protein of the virus (NS1) may cross-react with fibrinogen, thrombocytes and endothelial cells, thus triggering hemorrhages.

Currently, there is no specific treatment for Dengue Fever. Recommended therapies address symptoms, and include bed rest, control of the fever and pain through antipyretics and/or analgesics, and adequate hydration. Efforts focus on balancing liquid losses, replacement of coagulation factors and the infusion of heparin. The sequence and antigenic variability of DVs have challenged efforts to develop effective vaccines or therapeutics (Whitehead et al., 2007 Nature Reviews Microbiology 5:518-528). Unfortunately, the leading vaccine candidate recently demonstrated protective efficacy of only 30% in a phase II study (Thomas et al., 2011 Curr Op Infectious Disease 24:442-450; Sabchareon et al., 2012 Lancet 380(9853):1559-1567). Therefore, there is a need for the development of improved DV therapies, vaccines. Particularly valuable would be the development of treatments applicable to all DV serotypes. Such a therapy would have a tremendous impact on human health, especially in developing countries.

DV Antigens

DV infections are caused by four viruses (DV1-4), which are of similar serological type but differ antigenically. DVs are positive single-stranded RNA viruses belonging to the genus *flavivirus* within the Flaviviridae family. The virion comprises a spherical particle, 40-50 nm in diameter, with a lipopolysaccharide envelope. The RNA genome, which is approximately 11 kb in length, comprises a 5' type I end but lacks a 3' poly-A tail. The organization of the genome comprises the following elements: a 5' non-coding region (NCR), a region encoding structural proteins (capsid (C), pre-membrane/membrane (prM/M), envelope (E)) and a region encoding non-structural proteins (NS1-NS2A-NS2B-NS3-NS4A-NS4B-NS5) and a 3' NCR.

The viral genomic RNA is associated with the capsid proteins to form a nucleocapsid. As typical of flaviviruses, the Dengue viral genome encodes an uninterrupted coding region which is translated into a single polyprotein which is post-translationally processed. Important biological properties of DV, include receptor binding, hemagglutination of erythrocytes, induction of neutralizing antibodies and the protective immune response, are associated with the E protein (Wahala et al., 2011 Viruses 3:2374-2395).

The PrM protein, a glycoprotein of about 19 kDa, contains six highly conserved cysteine residues forming three disulfide bridges and is cleaved to Pr and M proteins by furin or furin-like protease during maturation.

The NS1 protein, also a glycoprotein of about 40 kDa, contains 12 highly conserved cysteine residues forming six disulfide bridges and is present intracellularly, on the cell surface, and outside the cells (Lai et al., 2008 Journal of Virology 82(13):1663'-43).

The E protein, a glycoprotein of approximately 55 kDa, contains 12 strictly conserved cysteine residues forming six disulfide bridges and is present as a heterodimer with PrM protein before the maturation of the virion. X-ray crystallographic studies of the ectodomain of E protein have revealed three distinct beta-barrel domains connected to the viral membrane by a helical stem anchor and two antiparallel transmembrane domains. Domain III (EDIII) adopts an immunoglobulin-like fold and has been suggested to play a critical role in receptor interactions. Domain II (EDII) is an elongated domain composed of two long finger-like structures and contains a highly conserved 13 amino acid fusion loop (EDII-FL) at the tip, and participates in the membrane fusion and, dimerization of E protein. The central domain of E (domain I; EDI) is a nine-stranded β-barrel that is connected to EDIII and EDII by one and four flexible linkers, respectively. E proteins are important for viral assembly, receptor attachment, entry, viral fusion, and possibly immune evasion during the flavivirus life cycle and, thus, are dynamic proteins required to adopt several distinct conformations and arrangements on the virus particle. Moreover, E protein is the major target of both neutralizing and enhancing antibodies (Lai et al, 2008 Journal of Virology 82:6631-6643; Pierson et al., 2008 Cell Host & Microbe. 4:229-38).

DVs are assembled on the membrane of the endoplasmic reticulum (ER) and the virus buds into the lumen of the ER as immature virus particles. Unlike mature virus particles that have a smooth surface, immature virus particles that bud into the ER have a rough surface created by trimers of E/prM heterodimers that form sixty spiked projections with icosahedral symmetry on the viral envelope (Perera et al., 2008 Antivir. Res. 80 11-22). The E proteins of each trimer project away from the surface of the virion and interact with prM via the distal end of EDII including the fusion loop. PrM on immature virions restricts the ability of E proteins to undergo oligomeric rearrangement in the low pH Golgi-derived secretory compartments during viral egress, thus preventing premature and adventitious fusion (Guirakhoo et al., 1991 Journal of Virology 72:1323-1329; Heinz et al., 1994 Journal of Virology 198(1):109-117). As immature virions traffic through the acidic compartments of the trans-Golgi network (TGN), changes in the orientation of prM and E proteins unmask a site for the cellular serine protease furin. In this low pH environment, the E proteins of immature virions form antiparallel dimers that lie flat against the surface of the virion and are arranged with T=3 quasi-icosahedral symmetry (Yu et al., 2009 Journal of Virology 83(23):12101-12107). The prM protein continues to mask the fusion loop of EDII until it is released after furin cleavage and a transition to neutral pH occurs in the extracellular space. The resulting mature and infectious viruses are relatively smooth particles composed of 90 E protein dimers and 180 copies of the ~70 amino acid M protein. In this configuration, E proteins on the mature DV exist in three distinct environments defined by their proximity to the 2-, 3-, or 5-fold axis of symmetry (Kuhn et al., 2002 Cell 108:717-25). Thus, all the E protein subunits are not in identical environments on the viral surface and steric and other considerations result in preferential interactions of some E subunits over others with receptors and antibodies.

Antibodies recognizing the highly conserved fusion loop on E protein demonstrate broad reactivity to all four DV serotypes; however their neutralization potency is typically limited, presumably due to this epitope being largely inaccessible in mature DV. Some antibodies which recognize the 'A' β-strand of E protein domain III (EDIII) have been shown to potently neutralize particular DV strains, but are not known to be effective against all four serotypes (Lok et al., Nature Structural & Molecular Biol. 15:312-317). The 'A' β-strand is part of a sub complex epitope centered at positions 305-308 (DV3 numbering) on the EDIII.

As described herein, the present invention encompasses the finding that the E antigen, and particularly the EDIII domain can serve as a useful antigenic target for broad-spectrum anti-DV antibody agents. The invention particularly demonstrates that antibodies that bind to the E antigen (e.g., to the EDIII domain) but do not neutralize all DV serotypes can be rationally engineered to produce variants, and/or other antibody agents, that do neutralize all of DV serotypes 1-4 (see, e.g., FIG. 3). Furthermore, the present invention demonstrates that antibodies that bind to the E antigen (e.g., to the EDIII domain) and neutralize some but not all DV serotypes can be rationally engineered to produce variants, and/or other antibody agents, that have gained neutralization activity, as compared with the parent antibody, against one or more particular strains and/or serotypes, without significantly depleting their activity, as compared with the parent antibody, against certain other strains and/or subtypes.

4E11 Antibody

Antibodies have proven to be an effective class of antiviral therapeutics, in part due to their high biochemical specificity and their established safety record. Additionally, antibodies have a long serum half-life (~21 days), enabling prophylactic uses in people, an application of particular need for infectious diseases which show rapid outbreaks, including Dengue Virus.

Antibodies that protect against flavivirus infection are believed to act through multiple mechanisms, including one or more of (1) direct neutralization of receptor binding, (2) inhibition of viral fusion, (3) Fc-γ-receptor-dependent viral clearance, (4) complement-mediated lysis of virus or infected cells, and (5) antibody-dependent cytotoxicity of infected cells (Pierson et al., 2008 Cell Host & Microbe 4:229-38). Flavivirus neutralization is thought to require binding by multiple antibodies (Dowd et al., 2011 Virology 411:306-15). Studies with E16, an EDIII binding mAb that neutralizes West Nile virus at a post attachment stage, indicate that ~30 antibodies need to bind for effective neutralization. Studies have suggested that both the affinity of antibody binding and the total number of accessible epitopes contribute to the neutralization potency of an antibody. Thus, even for an antibody that binds with high affinity, the antibody will fail to neutralize if the number of accessible epitopes is below certain level required for neutralization. Conversely, a lower affinity antibody may neutralize if many of the epitopes are accessible to binding.

As already noted, Dengue viruses (DVs) display antibody epitopes that are unique to each serotype and epitopes that are shared between serotypes. Most studies to understand how antibodies neutralize or enhance DV have been done with mouse monoclonal antibodies (mAbs). As E protein is the main antigen exposed on the surface of the virion, mouse mAbs that bind to E protein have been the focus of much analysis. Although neutralizing mouse mAbs have been mapped to all three domains, the most strongly neutralizing mAbs are serotype-specific and bind to EDIII, which protrudes from the surface of the virion. Two partially overlapping epitopes on EDIII designated the lateral ridge and A-strand epitopes are the main targets of mouse mAbs that neutralize DV.

The lateral ridge epitope interacts with serotype-specific strongly neutralizing antibodies. For example, mAb 3H5 maps to the EDIII-LR of DV serotype 2, and the epitope recognized by these mAbs is located on both the A-strand (amino acid 304) and the FG loop (residues 383 and 384) (Sukupolyi-Petty et al., 2007 Journal of Virology 81(23): 12816-12826).

However, not all antibodies that bind EDIII exhibit type-specific neutralizing activity. mAbs that bind to the A-strand epitope cross react with more than one serotype of DV and are designated Dengue Virus sub-complex neutralizing mAbs. For example, the sub complex-specific mAb 1A1D-2 recognizes an epitope centered on the A-strand of the lateral surface of EDIII and can neutralize infection by DV serotypes 1-3 (DV1-3), but not DV serotype 4 (DV4) (Lok et al., 2008 Nature Struct Mol Biot 15(3):312-317; Roehrig et al., 1998 Virology 246(2):317-328; Sukupolyi-Petty et al., 2007 Journal of Virology 81(23): 12816-12826). The molecular basis for the specificity of this mAb has been investigated; only one of three residues at the center of the 1A1D-2 epitope is conserved among all four DV serotypes (DV1-4). A similar A-strand epitope is also recognized by the broadly neutralizing cross reactive DV mAb 4E11 (Thullier et al., 2001 Journal Gen Virol. 82(8):1885-1892). Experimental approaches so far have however, failed to yield antibodies capable of potently neutralizing all four DV serotypes.

One particular murine monoclonal antibody, known as 4E11, that binds within EDIII of the E glycoprotein, shows potent neutralizing activity against DV serotypes 1-4. 4E11 binds to a conformational epitope on DV EDIII of E glycoprotein and cross reacts with all four serotypes. 4E11 potently neutralizes DV1-3 by interfering with attachment to host cell. However, it has poor affinity, and therefore weak neutralizing activity, against DV4

A hybridoma cell line that secretes mouse monoclonal antibody 4E11 has been deposited in the American Type Culture Collection (ATCC) Accession number: HB-9259. Sequences of wild type ("wt") 4E11 heavy chain (HC; SEQ ID NO. 1) and light chain (LC; SEQ ID NO. 2) are known. Sequences of wt 4E11 framework (FR) and complement determining regions (CDRs) are known (wt 4E11 HC FR1 is SEQ ID NO. 3, wt 4E11 HC FR2 is SEQ ID NO. 4, wt 4E11 HC FR3 is SEQ ID NO. 5, wt 4E11 HC FR4 is SEQ ID NO. 6, wt 4E11 HC CDR1 is SEQ ID NO. 7, wt 4E11 HC CDR2 is SEQ ID NO. 8, wt 4E11 HC CDR3 is SEQ ID NO. 9; wt 4E11 LC FR1 is SEQ ID NO. 10, wt 4E11 LC FR2 is SEQ ID NO. 11, wt 4E11 LC FR3 is SEQ ID NO. 12, wt 4E11 LC FR4 is SEQ ID NO. 13, wt 4E11 LC CDR1 is SEQ ID NO. 14, wt 4E11 LC CDR2 is SEQ ID NO. 15, wt 4E11 LC CDR3 is SEQ ID NO. 16).

```
SEQ ID NO. 1:
EVKLLEQSGAELVKPGASVRLSCTASGFNIKDTYMSWVKQRPEQGLEWIGRIDPANGDT

KYDPKFQGKATITADTSSNTAYLHLSSLTSGDTAVYYCSRGWEGFAYWGQGTLVTVSA

SEQ ID NO. 2:
ELVMTQTPASLAVSLGQRATISCRASENVDRYGNSFMHWYQQKAGQPPKLLIYRASNL

ESGIPARFSGSGSRTDFTLTINPVEADDVATYFCQRSNEVPWTFGGGTKLEIKR

SEQ ID NO. 3:
EVKLLEQSGAELVKPGASVRLSCTAS

SEQ ID NO. 4:
YMSWVKQRPEQGLEWIGRI

SEQ ID NO. 5:
TKYDPKFQGKATITADTSSNTAYLHLSSLTSGDTAVYYCSR

SEQ ID NO. 6:
WGQGTLVTVSA

SEQ ID NO. 7:
GFNIKDT

SEQ ID NO. 8:
DPANGD

SEQ ID NO. 9:
GWEGFAY

SEQ ID NO. 10:
ELVMTQTPASLAVSLGQRATISC

SEQ ID NO. 11:
WYQQKAGQPPKLLIY
```

```
-continued
SEQ ID NO. 12:
GIPARFSGSGSRTDFTLTINPVEADDVATYFC

SEQ ID NO. 13:
FGGGTKLEIKR

SEQ ID NO. 14:
RASENVDRYGNSFMH

SEQ ID NO. 15:
RASNLES

SEQ ID NO. 16:
QRSNEVPWT
```

The present invention encompasses the recognition that it would be desirable to develop antibodies (or other antibody agents) that are variants of wt 4E11. The present invention particularly provides such antibodies and antibody agents. That is, the present invention provides various antibody agents that show significant structural identity with 4E11 and moreover show improved functional characteristics (e.g., neutralization of DV4) as compared with that observed with wt 4E11.

The present disclosure provides a novel scoring metric for docking an antigen-antibody interaction. The scoring metric framework ranks protein-protein interfaces according to physicochemical features and propensities of pairwise amino acid interactions observed in intermolecular interfaces. The present disclosure uses this framework to modify properties of an existing antibody. In some embodiments, the specificity and affinity of an antibody for its antigen is modified. In some embodiments, the modified antibody is a monoclonal antibody. In some embodiments, the framework disclosed in the present invention is used to engineer broader specificity and affinity to an anti-DV neutralizing mAb.

Using the docked model, the mode of anti-DV antibodies binding to all four serotypes of DV (DV1-4) was examined and the structural basis of poor affinity of these antibodies towards DV4 were identified. Mutations were carefully designed on the paratope of these antibodies to improve their affinity, and thereby their neutralizing activity, towards DV4, while maintaining affinity, and neutralizing activity, towards DV1-3. For designing, the mutations, the CDR loop residues of the mAbs were carefully examined one at a time. At a given CDR position, the "wild-type" residue was systematically substituted by the remaining amino acids excluding glycine (Gly) and proline (Pro), and the probability of replacement was evaluated at each instance using the statistical pairwise propensities. Gly and Pro residues were not modified to avoid alteration in the backbone conformation. Single mutations with high replacement potential were modeled, and re-evaluated computationally to find mutations that: (1) do not alter phi-psi values; (2) do not bury polar groups; and (3) improved E1-bonds, salt bridge, van der Waals, hydrophobic contacts, and packing. Promising single mutations identified by the computational approach were screened using a high throughput indirect enzyme linked immunosorbent assay (ELISA) method to identify positive mutations that improve affinity towards DV4 EDIII while maintaining affinity towards DV1-3 EDIII. Finally, positive single mutations were combined to rationally design high affinity antibodies. Competition ELISA experiments were carried out to determine the affinity, at equilibrium and in solution, between the engineered antibodies and EDIII from each of the four serotypes. Binding measurements were verified using surface plasmon resonance (SPR) analysis.

In some embodiments, antibodies against A-strand epitope can be engineered to bind to all four serotypes of DV. In some embodiments, wt 4E11 anti-DV antibody is modified to improve its affinity, and thereby neutralizing activity towards DV4, while maintaining affinity towards DV1-3. In some embodiments, one of the engineered antibodies displays ~15 and ~450 fold improvement in affinity toward of DV2 and DV4, respectively, while maintaining original affinity towards EDIII of DV1 and DV3. In some embodiments, compared to wt mAb 4E11, the engineered antibody showed >75 fold increased neutralizing potential towards DV4, while still maintaining "wild-type" activity towards other serotypes. The engineered 4E11 antibody according to the present invention represents an interesting candidate for a therapeutic antibody to treat Dengue disease.

Provided Variant DV Antibody Agents

It will be appreciated that provided antibody agents may be engineered, produced, and/or purified in such a way as to improve characteristics and/or activity of the antibody agents. For example, improved characteristics of provided antibody agents include, but are not limited to, increased stability, improved binding affinity and/or avidity, increased binding specificity, increased production, decreased aggregation, decreased nonspecific binding, among others.

In general, as described herein, provided antibody agents can be or include, e.g., a polyclonal antibody; a monoclonal antibody or antigen binding fragment thereof; a modified antibody such as a chimeric antibody, reshaped antibody, humanized antibody, or fragment thereof (e.g., Fab', Fab, F(ab')$_2$); or a biosynthetic antibody, e.g., a single chain antibody, single domain antibody (DAB), Fv, single chain Fv (scFv), or the like.

Methods of making and using polyclonal and monoclonal antibodies are described, e.g., in Harlow et al., Using Antibodies: A Laboratory Manual: Portable Protocol I. Cold Spring Harbor Laboratory (Dec. 1, 1998). Methods for making modified antibody agents, such as, antibodies and antibody fragments (e.g., chimeric antibodies, reshaped antibodies, humanized antibodies, or fragments thereof, e.g., Fab', Fab, F(ab')$_2$ fragments); or biosynthetic antibodies (e.g., single chain antibodies, single domain antibodies (DABs), Fv, single chain Fv (scFv), and the like), are known in the art and can be found, e.g., in Zola, Monoclonal Antibodies: Preparation and Use of Monoclonal Antibodies and Engineered Antibody Derivatives, Springer Verlag (Dec. 15, 2000; 1st edition).

The present invention provides antibody agents that bind to all four serotypes of DV (DV1-4). In some embodiments, the present invention provides antibody agents that bind to DV1 with a higher affinity, as compared to the affinity of another antibody to DV1. In some embodiments, the present invention provides antibody agents that bind with a higher affinity to DV2, as compared to the affinity of another antibody to DV2. In some embodiments, the present invention provides antibody agents that bind with a higher affinity to DV3, as compared to the affinity of another antibody to DV3. In some embodiments, the present invention provides antibody agents that bind with a higher affinity to DV4, as compared to the affinity of another antibody to DV4. In some embodiments, the present invention provides antibody agents that bind with a higher affinity to DV1, DV2, DV3, and DV4, as compared to the affinity of another antibody to DV1, DV2, DV3, and DV4. In some embodiments, the present invention provides antibody agents that bind with higher affinity to DV4, and retain binding affinity to DV1, DV2, and DV3, as compared to the affinities of another antibody for these DV serotypes. In some embodiments, the present invention provides antibody agents that bind to DV1 and DV4 with higher affinities, as compared to the affinities of another antibody for these DV serotypes. In some embodiments, provided antibody agents bind with a higher affinity to DV1 and DV4, and retain their binding affinity to DV2 and DV3, as compared to the affinities of another antibody for these DV serotypes. In some embodiments, the present invention provides antibody agents that bind to DV2 and DV4 with higher affinities, as compared to the affinities of another antibody for these DV serotypes. In some embodiments, provided antibody agents bind with a higher affinity to DV2 and DV4, and retain their binding affinity to DV1 and DV3, as compared to the affinities of another antibody for these DV serotypes. In some embodiments, the present invention provides antibody agents that bind to DV3 and DV4 with higher affinities, as compared to the affinities of another antibody for these DV serotypes. In some embodiments, provided antibody agents bind with a higher affinity to DV3 and DV4, and retain their binding affinity to DV1 and DV2, as compared to the affinities of another antibody for these DV serotypes.

In some embodiments, provided antibody agents bind to one or more of DV1-4 with an affinity of at least 5%, 10%, 15%, 20%, 25%, 30%, 35%, 40%, 45%, 50%, 55%, 60%, 65%, 70%, 75%, 80%, 85%, 90% or more than the affinity of a different antibody for one or more of DV1-4. In some embodiments, provided antibody agents bind to one or more of DV1-4 with an affinity of at least 2-fold, at least 5-fold, at least 10-fold, at least 20-fold, at least 30-fold, at least 40-fold, at least 50-fold, at least 60-fold, at least 70-fold, at least 80-fold, at least 90-fold, at least 100-fold, at least 200-fold, at least 300-fold, at least 400-fold, at least 500-fold or greater affinity than that of a different antibody for one or more of DV1-4. In some embodiments, provided antibody agents show binding affinities for different DV serotypes that are within 2, within 5, within 10, within 25, within 50, within 100, within 150, within 200, within 250, within 300, within 350, or within 400-fold affinity of one another.

In some embodiments, provided antibody agents show a neutralization $IC_{50}$ (ug/ml) within a range as described and/or exemplified herein. In some embodiments, provided antibody agents show a neutralization $IC_{50}$ (ug/ml) whose lower bound is about 0.05 ug/ml and upper bound is about 10 ug/ml. In some embodiments, provided antibody agents show a neutralization $IC_{50}$ (ug/ml) whose lower bound is selected from the group consisting of 0.05 ug/ml, 0.1 ug/ml, 0.2 ug/ml, 0.3 ug/ml, 0.4 ug/ml, 0.5 ug/ml, 0.6 ug/ml, 0.7 ug/ml, 0.8 ug/ml, 0.9 ug/ml, 1.0 ug/ml, 1.1 ug/ml, 1.2 ug/ml, 1.3 ug/ml, 1.4 ug/ml, 1.5 ug/ml, 1.6 ug/ml, 1.7 ug/ml, 1.8 ug/ml, 1.9 ug/ml, 2.0 ug/ml, 2.5 ug/ml, 3.0 ug/ml, 3.5 ug/ml, 4.0 ug/ml, 4.5 ug/ml, 5.0 ug/ml or more, and whose upper bound is higher than the lower bound and is selected from the group consisting of 1.5 ug/ml, 1.6 ug/ml, 1.7 ug/ml, 1.8 ug/ml, 1.9 ug/ml, 2.0 ug/ml, 2.5 ug/ml, 3.0 ug/ml, 3.5 ug/ml, 4.0 ug/ml, 4.5 ug/ml, 5.0 ug/ml, 5.5 ug/ml, 6.0 ug/ml, 6.5 ug/ml, 7.0 ug/ml, 7.5 ug/ml, 8.0 ug/ml, 8.5 ug/ml, 9.0 ug/ml, 9.5 ug/ml, 10.0 ug/ml or more.

In some embodiments, provided antibody agents show binding to DV1-4 with a $K_D$ (nM) less than 40000 nM, less than 30000 nM, less than 20000 nM, less than 10000 nM, less than 5000 nM, less than 2000 nM, less than 1500 nM, less than 1000 nM, less than 500 nM, less than 250 nM, less than 225 nM, less than 200 nM, less than 175 nM, less than 150 nM, less than 125 nM, less than 100 nM, less than 75 nM, less than 50 nM, less than 25 nM, less than 15 nM, less than 10 nM, less than 5 nM, less than 2.5 nM, less than 1 nM, less than 0.5 nM, less than 0.25 nM, less than 0.1 nM.

In some embodiments, provided antibody agents show binding to DV1-4 with a $K_{on}$ ($M^{-1}s^{-1}$) whose lower bound is about $0.01 \times 10^5$ $M^{-1}s^{-1}$ and upper bound is about $5.0 \times 10^6$ $M^{-1}s^{-1}$. In some embodiments, provided antibodies show binding to DV1-4 with a $K_{on}$ ($M^{-1}s^{-1}$) whose lower bound is selected from the group consisting of $0.01 \times 10^5$ $M^{-1}s^{-1}$, $0.05 \times 10^5$ $M^{-1}s^{-1}$, $0.1 \times 10^5$ $M^{-1}s^{-1}$, $0.5 \times 10^5$ $M^{-1}s^{-1}$, $1.0 \times 10^5$ $M^{-1}s^{-1}$, $2.0 \times 10^5$ $M^{-1}s^{-1}$, $5.0 \times 10^5$ $M^{-1}s^{-1}$, $7.0 \times 10^5$ $M^{-1}s^{-1}$, or more, and whose upper bound is higher than the lower bound and is selected from the group consisting of $1.0 \times 10^6$ $M^{-1}s^{-1}$, $1.5 \times 10^6$ $M^{-1}s^{-1}$, $2.0 \times 10^6$ $M^{-1}s^{-1}$, $2.5 \times 10^6$ $M^{-1}s^{-1}$, $3.0 \times 10^6$ $M^{-1}s^{-1}$, $3.5 \times 10^6$ $M^{-1}s^{-1}$, $4.0 \times 10^6$ $M^{-1}s^{-1}$, $4.5 \times 10^6$ $M^{-1}s^{-1}$, $5.0 \times 10^6$ $M^{-1}s^{-1}$, or more.

In some embodiments, provided antibody agents show binding to DV1-4 with a $K_{off}$ ($s^{-1}$) whose lower bound is about $5 \times 10^{-4}$ $s^{-1}$ and upper bound is about $900 \times 10^{-4}$ $s^{-1}$. In some embodiments, provided antibody agents show binding to DV1-4 with a $K_{off}$ ($s^{-1}$) whose lower bound is selected from the group consisting of $5 \times 10^{-4}$ $s^{-1}$, $10 \times 10^{-4}$ $s^{-1}$, $12 \times 10^{-4}$ $s^{-1}$, $13 \times 10^{-4}$ $s^{-1}$, $14 \times 10^{-4}$ $s^{-1}$, $15 \times 10^{-4}$ $s^{-1}$, $18 \times 10^{-4}$ $s^{-1}$, $20 \times 10^{-4}$ $s^{-1}$, or more, and whose upper bound is higher than the lower bound and is selected from the group consisting of $50 \times 10^{-4}$ $s^{-1}$, $100 \times 10^{-4}$ $s^{-1}$, $120 \times 10^{-4}$ $s^{-1}$, $140 \times 10^4$ $s^{-1}$, $150 \times 10^4$ $s^{-1}$, $200 \times 10^4$ $s^{-1}$, $300 \times 10^4$ $s^{-1}$, $400 \times 10^4$ $s^{-1}$, $500 \times 10^4$ $s^{-1}$, $600 \times 10^4$ $s^{-1}$, $700 \times 10^{-4}$ $s^{-1}$, $800 \times 10^{-4}$ $s^{-1}$, $900 \times 10^{-4}$ $s^{-1}$, or more.

In some embodiments, provided antibody agents bind to E glycoprotein of DV1-4. In certain embodiments, provided antibody agents bind to EDIII of DV1-4 (SEQ ID NOs. 17-20). In some embodiments, provided antibody agents bind to A-strand of DV1-4. In some embodiments, the present invention provides antibody agents that bind with higher affinity to EDIII of DV4 (SEQ ID NO. 20). In some embodiments, the present invention provides antibody agents that bind with higher affinity to A-strand of DV4.

SEQ ID NO. 17:
MCTGSFKLEKEVAETQHGTVLVQVKYEGTDAPCKIPFSSQDEKGVTQNGRLITANPIVT

DKEKPVNIEAEPPFGESYIVVGAGEKALKLSWFK

SEQ ID NO. 18:
MCTGKFKVVKEIAETQHGTMVIRVQYEGDDSPCKIPFEIMDLEKKHVLGRLITVNPIVIE

KDSPINIEAEPPFGDSYIIIGVEPGQLKLNWFK

SEQ ID NO. 19:
MCTNTFVLKKEVSETQHGTILIKVEYKEDAPCKIPFSTEDGQGKAHNGRLITANPVVTK

KEEPVNIEAEPPFGESNIVIGIGDNALKINWYK

SEQ ID NO. 20:
MCSGKFSIDKEMAETQHGTTVVKVKYEGAGAPCKVPIEIRDVNKEKVVGRIISSTPLAEN

TNSVTNIELEPPFGDSYIVIGVGNSALTLHWFR

In some embodiments, the present invention identifies antibody agents that bind to one or more amino acid residues in EDIII of DV1-4 (SEQ ID NOs. 17-20) at positions 305, 306, 307, 308, 309, 310, 311, 312, 323, 325, 327, 329, 360, 361, 362, 363, 364, 385, 387, 388, 389, 390, 391, and/or combinations thereof. In some embodiments, the present invention identifies antibody agents that bind to one or more amino acid residues in EDIII of DV1-4 (SEQ ID NOs. 17-20) at positions 305, 310, 311, 323, 327, 329, and/or combinations thereof. In some embodiments, the present invention identifies antibody agents that bind amino acid residues in EDIII of DV1-4 (SEQ ID NOs. 17-20) at positions 305, 310, 311, 323, 327, and 329. In some embodiments, the present invention identifies antibody agents that bind amino acid residue in EDIII of DV1-4 (SEQ ID NOs. 17-20) at position 305. In some embodiments, the present invention identifies antibody agents that bind amino acid residue in EDIII of DV1-4 (SEQ ID NOs. 17-20) at position 310. In certain embodiments, the present invention identifies antibody agents that bind amino acid residue in EDIII of DV1-4 (SEQ ID NOs. 17-20) at position 311. In some embodiments, the present invention identifies antibody agents that bind amino acid residue in EDIII of DV1-4 (SEQ ID NOs. 17-20) at position 323. In some embodiments, the present invention identifies antibody agents that bind amino acid residue in EDIII of DV1-4 (SEQ ID NOs. 17-20) at position 327. In some embodiments, the present invention identifies antibody agents that bind amino acid residue in EDIII of DV1-4 (SEQ ID NOs. 17-20) at position 329.

In some embodiments, a serine, lysine, and/or threonine residue at position 305 contribute(s) to binding to provided antibody agents. In some embodiments, a lysine residue at position 310 contributes to binding to provided antibody agents. In some embodiments, a lysine residue at position 311 contributes to binding to provided antibody agents. In some embodiments, an arginine, lysine, and/or glutamine residue at position 323 contribute(s) to binding to provided antibody agents. In some embodiments, a serine and/or glutamate residue at position 327 contribute(s) to binding to provided antibody agents. In some embodiments, an arginine, aspartate, and/or glutamate residue at position 329 contribute(s) to binding to provided antibody agents.

In some embodiments, the present invention provides antibody agents that bind with higher affinity to DV1, as compared to a wild type ("wt") DV antibody. In some embodiments, the present invention provides antibody agents that bind with higher affinity to DV2, as compared to a wt or parent reference DV antibody. In some embodiments, the present invention provides antibody agents that bind with higher affinity to DV3, as compared to a reference antibody such as a wt DV antibody. In some embodiments, the present invention provides antibody agents that bind with higher affinity to DV4, as compared to a reference DV antibody. In some embodiments, the present invention provides antibody agents that bind with higher affinity to DV1, DV2, DV3, and DV4, as compared to a reference DV antibody. In some embodiments, the present invention provides antibody agents that bind with higher affinity to DV4 and retain binding affinity to DV1, DV2, and DV3, as compared to a reference DV antibody. In some embodiments, the present invention provides antibody agents that bind with higher affinity to DV2 and DV4, as compared to a reference (wt) DV antibody. In some embodiments, provided antibody agents that bind with higher affinity to DV2 and DV4 and retain their binding affinity to DV1 and DV3, as compared to a reference DV antibody. In some embodiments, a wt DV antibody is a wt 4E11 antibody.

As described herein, the present invention provides antibody agents that show certain structural (i.e., sequence) relationship with 4E11 and/or have particular functional attributes, including for example certain improved functional attributes as compared with wt 4E11.

In some embodiments, the present invention provides antibody agents whose amino acid sequences, show specified levels of homology and/or identity with wt 4E11. In some embodiments provided antibody agents show at least 60%, at least 70%, at least 80%, at least 90%, at least 95%, at least 99% identity with wt 4E11 (i.e., with SEQ ID NOs. 1-2).

In some embodiments, provided antibody agents have a heavy chain (HC; SEQ ID NO. 21) CDR1 comprising sequence GFNIKDT (SEQ ID NO. 23), a HC CDR2 comprising sequence DPENGD (SEQ ID NO. 24), a HC CDR3 comprising sequence GWEGFAY (SEQ ID NO. 25), a light chain (LC; SEQ ID NO. 22) CDR1 comprising sequence RASENVDKYGNSFMH (SEQ ID NO. 26), a LC CDR2 region comprising sequence RASELQW (SEQ ID NO. 27) and a LC CDR3 region comprising sequence QRSNEVPWT (SEQ ID NO. 28).

SEQ ID NO. 21:
EVKLLEQSGAELVKPGASVRLSCTASGFNIKDTYMSWVKQRPEQGLEWIGRIDPENGDT

KYDPKFQGKATITADTSSNTAYLHLSSLTSGDTAVYYCSRGWEGFAYWGQGTLVTVSA

SEQ ID NO. 22:
ELVMTQTPASLAVSLGQRATISCRASENVDKYGNSFMHWYQQKAGQPPKLLIYRASEL

QWGIPARFSGSGSRTDFTLTINPVEADDVATYFCQRSNEVPWTFGGGTKLEIKR

In some embodiments, provided antibody agents have one or more CDRs and/or one or more FRs that are identical in sequence to a corresponding CDR or FR of wt 4E11 (i.e. to one or more of SEQ ID NOs. 7-9, 14-16 or 3-6, 10-13). In some embodiments, provided antibody agents have one or more CDRs and/or FRs showing a specified degree of homology and/or identity with the corresponding CDRs and/or FRs of wt 4E11 as discussed below. In some embodiments, all CDRs and FRs of a provided antibody agents show at least the specified level of homology and/or identity. In some embodiments, a provided antibody agents has CDR and FR sequences that together contain no more than 18, 17, 16, 15, 14, 13, 12, 11, 10, 9, 8, 7, 6, 5, 4, 3, 2, or 1 substitutions as compared with wt 4E11.

In some embodiments, a complementarity determining region (CDR) 1 of an antibody agent of the present invention shows at least 65%, more than 70%, more than 75%, more than 80%, more than 85%, more than 90%, more than 95%, or more than 99% identity with wt 4E11 (SEQ ID NO. 7 and SEQ ID NO. 14). In some embodiments, a provided CDR1 has an amino acid sequence that is identical to that of wt 4E11 and/or does not contain any amino acid substitutions as compared with CDR1 of wt 4E11 (SEQ ID NO. 7 and SEQ ID NO. 14). In some embodiments, a provided CDR1 has one or more amino acid substitutions as compared to wt 4E11 (SEQ ID NO. 7 and SEQ ID NO. 14). In some embodiments, a provided CDR1 will have two or more amino acid substitutions as compared to wt 4E11 (SEQ ID NO. 7 and SEQ ID NO. 14). In some embodiments, a provided CDR has 1, 2, 3, 4 or 5 substitutions and in some embodiments 1, 2, or 3 substitutions as compared with wt 4E11.

In some embodiments, a CDR2 of an antibody agent of the present invention shows at least 65%, more than 70%, more than 75%, more than 80%, more than 85%, more than 90%, more than 95%, or more than 99% identity with wt 4E11 (SEQ ID NO. 8 and SEQ ID NO. 15). In some embodiments, a provided CDR2 has an amino acid sequence that is identical to that of wt 4E11 and/or does not contain any amino acid substitutions as compared with CDR2 of wt 4E11 (SEQ ID NO. 8 and SEQ ID NO. 15). In some embodiments, a provided CDR2 has one or more amino acid substitutions as compared to wt 4E11 (SEQ ID NO. 8 and SEQ ID NO. 15). In some embodiments, a provided CDR2 will have two or more amino acid substitutions as compared to wt 4E11 (SEQ ID NO. 8 and SEQ ID NO. 15). In some embodiments, a provided CDR has 1, 2, 3, 4 or 5 substitutions and in some embodiments 1, 2, or 3 substitutions as compared with wt 4E11.

In some embodiments, a CDR3 of an antibody agent of the present invention shows at least 65%, more than 70%, more than 75%, more than 80%, more than 85%, more than 90%, more than 95%, or more than 99% identity with wt 4E11 (SEQ ID NO. 9 and SEQ ID NO. 16). In some embodiments, a provided CDR3 has an amino acid sequence that is identical to that of wt 4E11 and/or does not contain any amino acid substitutions as compared with CDR3 of wt 4E11 (SEQ ID NO. 9 and SEQ ID NO. 16). In some embodiments, a provided CDR3 has one or more amino acid substitutions as compared to wt 4E11 (SEQ ID NO. 9 and SEQ ID NO. 16). In some embodiments, a provided CDR3 will have two or more amino acid substitutions as compared to wt 4E11 (SEQ ID NO. 9 and SEQ ID NO. 16). In some embodiments, a provided CDR has 1, 2, 3, 4 or 5 substitutions and in some embodiments 1, 2, or 3 substitutions as compared with wt 4E11.

In some embodiments, a provided framework region 1 (FR1) of an antibody agent of the present invention will share more than 65%, more than 70%, more than 75%, more than 80%, more than 85%, more than 90%, more than 95%, or more than 99% percent identity with wt 4E11 (SEQ ID ID NO. 3 and SEQ ID NO. 10). In some embodiments, a provided FR1 will not have an amino acid substitution as compared to wt 4E11 (SEQ ID ID NO. 3 and SEQ ID NO. 10). In some embodiments, a provided FR1 will have one or more amino acid substitutions as compared to wt 4E11 (SEQ ID ID NO. 3 and SEQ ID NO. 10). In some embodiments, a provided FR1 will have two or more amino acid substitutions as compared to wt 4E11 (SEQ ID ID NO. 3 and SEQ ID NO. 10).

In some embodiments, a provided framework region 2 (FR2) of an antibody agent of the present invention will share more than 65%, more than 70%, more than 75%, more than 80%, more than 85%, more than 90%, more than 95%, or more than 99% percent identity with wt 4E11 (SEQ ID NO. 4 and SEQ ID NO. 11). In some embodiments, a provided FR2 will not have an amino acid substitution as compared to wt 4E11 (SEQ ID NO. 4 and SEQ ID NO. 11). In some embodiments, a provided FR2 will have one or more amino acid substitutions as compared to wt 4E11 (SEQ ID NO. 4 and SEQ ID NO. 11). In some embodiments, a provided FR2 will have two or more amino acid substitutions as compared to wt 4E11 (SEQ ID NO. 4 and SEQ ID NO. 11).

In some embodiments, a provided framework region 3 (FR3) of an antibody agent of the present invention will share more than 65%, more than 70%, more than 75%, more than 80%, more than 85%, more than 90%, more than 95%, or more than 99% percent identity with wt 4E11 (SEQ ID NO. 5 and SEQ ID NO. 12). In some embodiments, a provided FR3 will not have an amino acid substitution as compared to wt 4E11 (SEQ ID NO. 5 and SEQ ID NO. 12). In some embodiments, a provided FR3 will have one or more amino acid substitutions as compared to wt 4E11 (SEQ ID NO. 5 and SEQ ID NO. 12). In some embodiments, a provided FR3 will have two or more amino acid substitutions as compared to wt 4E11 (SEQ ID NO. 5 and SEQ ID NO. 12).

In some embodiments, a provided framework region 4 (FR4) of an antibody agent of the present invention will share more than 65%, more than 70%, more than 75%, more than 80%, more than 85%, more than 90%, more than 95%, or more than 99% percent identity with wt 4E11 (SEQ ID NO. 6 and SEQ ID NO. 13). In some embodiments, a provided FR4 will not have an amino acid substitution as compared to wt 4E11 (SEQ ID NO. 6 and SEQ ID NO. 13). In some embodiments, a provided FR4 will have one or more amino acid substitutions as compared to wt 4E11 (SEQ ID NO. 6 and SEQ ID NO. 13). In some embodiments, a provided FR3 will have two or more amino acid substitutions as compared to wt 4E11 (SEQ ID NO. 6 and SEQ ID NO. 13).

In some embodiments, the VH CDR of the provided antibody agents show at least 60%, at least 70%, at least 80%, at least 90%, at least 95%, at least 99% identity with wt 4E11 (SEQ ID NOs.: 7-9). In some embodiments, the VH CDR of the provided antibody agents show at least 60%, at least 70%, at least 80%, at least 90%, at least 95%, at least 99% identity with wt 4E11 (SEQ ID NOs.: 7-9), but differs by substitution of at least one amino acid substitution within the CDR. In some embodiments, the VH CDR of provided antibody agents have a substitution of the corresponding amino acid residue at position 55 of the wt 4E11 antibody. In some embodiments, a substitute amino acid residue at position 55 is selected from the group consisting of glutamate and aspartate. In some embodiments, the substitute amino acid residue at position 55 is glutamate. In some embodiments, the amino acid residue in the VH CDR of provided antibodies corresponding to amino acid residue at position 55 of wt 4E11 is not alanine.

In some embodiments, the VL CDR of provided antibody agents show at least 60%, at least 70%, at least 80%, at least 90%, at least 95%, at least 99% identity with wt 4E11 (SEQ ID NOs.: 14-16). In some embodiments, the VL CDR of provided antibody agents show at least 60%, at least 70%, at least 80%, at least 90%, at least 95%, at least 99% identity with wt 4E11 (SEQ ID NOs.: 14-16), but differs by substitution of at least one amino acid substitution within the CDR. In some embodiments, the VL CDR of provided antibody agents have one or more substitutions of a corresponding amino acid residue at positions 31, 57, 59, 60 and/or combinations thereof, of the wt 4E11 antibody. In some embodiments, the VL CDR of provided antibody agents have a substitution of the corresponding amino acid residue at position 31 of the wt 4E11 antibody. In some embodiments, the substitute amino acid residue at position 31 is lysine. In some embodiments, the amino acid residue in the VL CDR of provided antibody agents corresponding to amino acid residue at position 55 of wt 4E11 is not arginine. In some embodiments, the VL CDR of provided antibody agents have a substitution of the corresponding amino acid residue at position 57 of the wt 4E11 antibody. In some embodiments, the substitute amino acid residue at position 57 is selected from the group consisting of glutamate and serine. In some embodiments, the substitute amino acid residue at position 57 is glutamate. In some embodiments, the amino acid residue in the VL CDR of provided antibody agents corresponding to amino acid residue at position 57 of wt 4E11 is not asparagine. In some embodiments, the VL CDR of provided antibody agents have substitution of the corresponding amino acid residue at position 59 of the wt 4E11 antibody. In some embodiments, the substitute amino acid residue at position 59 is selected from the group consisting of glutamine and asparagine. In some embodiments, the substitute amino acid residue at position 59 is glutamine. In some embodiments, the amino acid residue in the VL CDR of provided antibody agents corresponding to amino acid residue at position 59 of wt 4E11 is not glutamate. In some embodiments, the VL CDR of provided antibody agents have a substitution of the corresponding amino acid residue at position 60 of the wt 4E11 antibody. In some embodiments, the substitute amino acid residue at position 60 is selected from the group consisting of tryptophan, tyrosine, and arginine. In some embodiments, the substitute amino acid residue at position 60 is tryptophan. In some embodiments, the amino acid residue in the VL CDR of provided antibody agents corresponding to amino acid residue at position 60 of wt 4E11 is not serine.

In some embodiments, the VH and VL CDRs of the provided antibody agents show at least 60%, at least 70%, at least 80%, at least 90%, at least 95%, at least 99% identity with wt 4E11 (SEQ ID NOs.: 7-9 and 14-16, respectively). In some embodiments, the VH and VL CDRs of the provided antibody agents show at least 60%, at least 70%, at least 80%, at least 90%, at least 95%, at least 99% identity with wt 4E11 (SEQ ID NOs.: 7-9 and 14-16, respectively), but differ by substitution of at least one amino acid substitution within the CDRs. In some embodiments, the VH CDR of provided antibody agents have substitution of the corresponding amino acid residue at position 55, and VL CDR of provided antibody agents have substitution of the corresponding amino acid residue at positions 31, 57, 59 and 60, of the wt 4E11 antibody. In some embodiments, the substitute amino acid residue at position 55 is glutamate. In some embodiments, the substitute amino acid residue at position 31 is lysine. In some embodiments, the substitute amino acid residue at position 57 is glutamate. In some embodiments, the substitute amino acid residue at position 59 is glutamine. In some embodiments, the substitute amino acid residue at position 60 is tryptophan.

In some embodiments, the present invention provides antibody agents that show binding to EDIII-DV4 (SEQ ID NO. 20) with a $K_D$ (nM) less than 40000 nM, less than 30000 nM, less than 20000 nM, less than 15000 nM, less than 10000 nM, less than 8000 nM, less than 5000 nM, less than 4000 nM, less than 3000 nM, less than 2000 nM, less than 1500 nM, less than 1000 nM, less than 500 nM, less than 250 nM, less than 225 nM, less than 200 nM, less than 175 nM, less than 150 nM, less than 125 nM, less than 100 nM, less than 75 nM, or less than 50 nM.

In some embodiments, the present invention provides antibody agents that show binding to EDIII-DV1 (SEQ ID NO. 17) with a $K_D$ (nM) of less than 3 nM, less than 2.5 nM, less than 2 nM, less than 1.5 nM, less than 1.0 nM, less than 0.5 nM, less than 0.4 nM, less than 0.3 nM, less than 0.2 nM, less than 0.1 nM, or less than 0.05 nM.

In some embodiments, the present invention provides antibody agents that show binding to EDIII-DV2 (SEQ ID NO. 18) with a $K_D$ (nM) of less than 15 nM, less than 12 nM, less than 10 nM, less than 8 nM, less than 7 nM, less than 5 nM, less than 2.5 nM, less than 2 nM, less than 1.5 nM, less than 1 nM, less than 0.5 nM, less than 0.4 nM, less than 0.3 nM, less than 0.2 nM, or less than 0.1 nM.

In some embodiments, the present invention provides antibody agents that show binding to EDIII-DV3 (SEQ ID NO. 19) with a $K_D$ (nM) of less than 120 nM, less than 100 nM, less than 50 nM, less than 40 nM, less than 35 nM, less than 30 nM, less than 25 nM, less than 20 nM, less than 15 nM, less than 10 nM, less than 5 nM, less than 2.5 nM, or less than 1.0 nM.

In some embodiments, the present invention provides antibody agents with at least 2-fold, 5-fold, 10-fold, 20-fold, 30-fold, 40-fold, 50-fold, 60-fold, 70-fold, 80-fold, 90-fold, 100-fold, 200-fold, 300-fold, 400-fold, 500-fold, or greater affinity for binding to EDIII-DV4 than wt 4E11.

In some embodiments, the present invention provides antibody agents with at least 2-fold, 5-fold, 10-fold, 20-fold, 30-fold, 40-fold, 50-fold, 60-fold, 70-fold, 80-fold, 90-fold, or greater affinity for binding to EDIII-DV2 than wt 4E11.

In some embodiments, the present invention provides antibody agents with at least 1-fold, 1.5-fold, 2-fold, 5-fold, 10-fold, 20-fold, 30-fold, 40-fold, 50-fold, 60-fold, or greater affinity for binding to EDIII-DV1 and/or EDIII-DV3 than wt 4E11.

In some embodiments, the present invention provides antibody agents that show neutralization $IC_{50}$ (ug/ml) of EDIII-DV4 (SEQ ID NO. 20) of 60 ug/ml or less, 50 ug/ml or less, 40 ug/ml or less, 30 ug/ml or less, 20 ug/ml or less, 10 ug/ml or less, 5 ug/ml or less, 4 ug/ml or less, 3 ug/ml or less, 2 ug/ml or less.

In some embodiments, the present invention provides antibody agents that show neutralization $IC_{50}$ (ug/ml) of EDIII-DV3 (SEQ ID NO. 19) of 7.0 ug/ml or less, 6.0 ug/ml or less, 5.0 ug/ml or less, 4.0 ug/ml or less, 3.0 ug/ml or less, 2.0 ug/ml or less, 1.5 ug/ml or less, 1.0 ug/ml or less, 0.90 ug/ml or less, 0.80 ug/ml or less, 0.70 ug/ml or less, 0.60 ug/ml or less, 0.50 ug/ml or less.

In some embodiments, the present invention provides antibody agents that show neutralization $IC_{50}$ (ug/ml) of EDIII-DV2 (SEQ ID NO. 18) of 0.2 ug/ml or less, 0.19 ug/ml or less, 0.18 ug/ml or less, 0.17 ug/ml or less, 0.16 ug/ml or less, 0.15 ug/ml or less, 0.14 ug/ml or less, 0.13 ug/ml or less, 0.12 ug/ml or less, 0.11 ug/ml or less, 0.10 ug/ml or less, 0.09 ug/ml or less, 0.07 ug/ml or less, 0.06 ug/ml or less, 0.05 ug/ml or less, 0.04 ug/ml or less, 0.03 ug/ml or less, 0.02 ug/ml or less, 0.01 ug/ml or less.

In some embodiments, the present invention provides antibody agents that show neutralization $IC_{50}$ (ug/ml) of EDIII-DV1 (SEQ ID NO. 17) of 5.0 ug/ml or less, 4.0 ug/ml or less, 3.0 ug/ml or less, 2.5 ug/ml or less, 2.0 ug/ml or less, 1.5 ug/ml or less, 1.0 ug/ml or less, 0.90 ug/ml or less, 0.70 ug/ml or less, 0.50 ug/ml or less, 0.40 ug/ml or less, 0.30 ug/ml or less, 0.20 ug/ml or less, 0.10 ug/ml or less.

In some embodiments, the present invention provides antibody agents with at least 2-fold, 5-fold, 10-fold, 20-fold, 30-fold, 40-fold, 50-fold, 60-fold, 70-fold, 80-fold, 90-fold, 100-fold, 150-fold, 200-fold, 400-fold, 500-fold, or more reduction of $IC_{50}$ for neutralization of EDIII-DV4 than wt 4E11.

In some embodiments, the present invention provides antibody agents with at least 1-fold, 1.5-fold, 2-fold, 5-fold, 10-fold, 20-fold, 30-fold, 40-fold, 50-fold, 60-fold, or more reduction of $IC_{50}$ for neutralization of EDIII-DV2 than wt 4E11.

In some embodiments, the present invention provides antibody agents with at least 1-fold, 1.5-fold, 2-fold, 5-fold, 10-fold, 20-fold, 30-fold, 40-fold, 50-fold, 60-fold, or more reduction of $IC_{50}$ for neutralization of EDIII-DV1 and/or EDIII-DV3 than wt 4E11.

In some embodiments, one or more sequences in a provided antibody agents has been engineered (e.g., by affinity maturation or other optimization approach) to improve one or more characteristics or activities (e.g., to increase stability, decrease aggregation, decrease immunogenicity, etc.) as is known in the art.

In some embodiments, an antibody agent is modified by PEGylation, methylation, sialylation, amination or sulfation. In some embodiments, an antibody agent is conjugated to an amphiphilic core/shell to produce a polymeric micelle. In some embodiments, an antibody agent is conjugated to a hyperbranched macromolecule (i.e. dendrimer). In some embodiments, an antibody agent is conjugated to a natural polymer selected from the group consisting of albumin, chitosan, heparin, paclitaxel, poly-(L-glutamate), N-(2-hydroxypropyl)methacrylamide (HPMA), poly-(L-lactide) (PLA), poly(amidoamine) (PAMAM), folate and/or combinations thereof. In some embodiments, an antibody agent comprises one or more long unstructured tails of hydrophilic amino acids (rPEG). In some embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology may exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987).

Antibodies and/or Antibody Fragments

In some embodiments, a provided DV antibody agent is or comprises an antibody or fragment thereof. In some embodiments, a provided DV antibody agent is or comprises a monoclonal antibody or fragment thereof. In some embodiments, a provided DV antibody agent is or comprises a polyclonal antibody or fragment thereof. In some embodiments, the DV antibody agent is or comprises a "full length" antibody, in that it contains two heavy chains and two light chains, optionally associated by disulfide bonds as occurs with naturally-produced antibodies. In some embodiments, the DV antibody agent is or comprises a fragment of a full-length antibody in that is contains some, but not all of the sequences found in a full-length antibody. For example, in some embodiments, a DV antibody agent is or comprises antibody fragments which include, but are not limited to, Fab, Fab', F(ab')2, scFv, Fv, dsFv diabody, and Fd fragments. In some embodiments, a provided DV antibody agent is or comprises an antibody that is a member of an antibody class selected from the group consisting of IgG, IgM, IgA, IgD, IgE or fragment thereof. In some embodiments, a provided DV antibody agent is or comprises an antibody produced by chemical synthesis. In some embodiments, a provided DV antibody agent is or comprises an antibody produced by a cell. In some embodiments, a provided DV antibody agent is or comprises an antibody produced using a recombinant cell culture system. In some embodiments, a provided DV antibody agent is or comprises a chimeric antibody, for example from mouse, rat, horse, pig, or other species, bearing human constant and/or variable region domains.

In some embodiments, a DV antibody agent includes one or more antibody fragments, including, but not limited to Fab', Fab, F(ab')2, single domain antibodies (DABs), Fv, scFv (single chain Fv), polypeptides with antibody CDRs, scaffolding domains that display the CDRs (e.g., anticalins) or nanobodies. For example, a provided antibody may be a VHH (i.e., an antigen-specific VHH) antibody that comprises only a heavy chain. Such antibody molecules can be derived from a llama or other camelid antibody (e.g., a camelid IgG2 or IgG3, or a CDR-displaying frame from such camelid Ig) or from a shark antibody. In some embodiments the DV antibody agent is or comprises an avibody (diabody, tribody, tetrabody). Techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference).

In some embodiments, provided DV antibody agent include one or more "Mini-antibodies" or "minibodies". Minibodies are sFv polypeptide chains which include oligomerization domains at their C-termini, separated from the sFv by a hinge region (Pack et al. (1992) *Biochem* 31:1579-1584). The oligomerization domain comprises self-associating α-helices, e.g., leucine zippers, that can be further stabilized by additional disulfide bonds. The oligomerization domain is designed to be compatible with vectorial folding across a membrane, a process thought to facilitate in vivo folding of the polypeptide into a functional binding protein. Generally, minibodies are produced using recombinant methods well known in the art. See, e.g., Pack et al. (1992) Biochem 31:1579-1584; Cumber et al. (1992) *J Immunology* 149B:120-126.

Antibody Agent Conjugates

In some embodiments, a provided DV antibody agent is or comprises a conjugate, in which an antibody moiety comprises or consists of the antibody or a functional portion thereof with a conjugated moiety. In some particular embodiments, DV antibody agent as described herein are provided and/or utilized in association with one or more active agents or "payloads", such as a therapeutic or detection agent. In some such embodiments, association between the DV antibody agent and the active agent and/or payload comprises at least one covalent interaction so that a DV antibody conjugate is provided.

In some embodiments, an antibody agent is a therapeutic payload agent is an effector entity having a desired activity, e.g., anti-viral activity, anti-inflammatory activity, cytotoxic activity, etc. Therapeutic agents can be or comprise any class of chemical entity including, for example, proteins, carbohydrates, lipids, nucleic acids, small organic molecules, non-biological polymers, metals, ions, radioisotopes, etc. In some embodiments, therapeutic agents for use in accordance with the present invention may have a biological activity relevant to the treatment of one or more symptoms or causes of DV infection (e.g., for example, anti-viral, pain-relief, anti-inflammatory, immunomodulatory, sleep-inducing activities, etc). In some embodiments, therapeutic agents for use in accordance with the present invention have one or more other activities.

In some embodiments, an antibody agent is a payload detection agent that is or comprises any moiety which may be detected using an assay, for example due to its specific functional properties and/or chemical characteristics. Non-limiting examples of such agents include enzymes, radiolabels, haptens, fluorescent labels, phosphorescent molecules, chemiluminescent molecules, chromophores, luminescent molecules, photoaffinity molecules, colored particles or ligands, such as biotin.

Many appropriate payload detection agents are known in the art, as are systems for their attachment to antibodies (see, for e.g., U.S. Pat. Nos. 5,021,236; 4,938,948; and 4,472,509, each incorporated herein by reference). Examples of such payload detection agents include paramagnetic ions, radioactive isotopes, fluorochromes, NMR-detectable substances, X-ray imaging agents, among others. For example, in some embodiments, a paramagnetic ion is one or more of chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III), erbium (III), lanthanum (III), gold (III), lead (II), and/or bismuth (III).

In some embodiments, a radioactive isotope is one or more of astatine-211, 14-carbon, 51chromium, 36-chlorine, 57cobalt, 58cobalt, copper67, 152Eu, gallium67, 3hydrogen, iodine-123, iodine-125, iodine-131, indium111, 59iron, 32phosphorus, radium223, rhenium186, rhenium188, 75selenium, 35sulphur, technicium99m, thorium227 and/or yttrium90. Radioactively labeled antibody agents may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Provided antibody agents may be labeled with technetium99m by ligand exchange process, for example, by reducing pertechnate with stannous solution, chelating the reduced technetium onto a Sephadex column and applying the antibody to this column. In some embodiments, provided DV antibody agents are labeled using direct labeling techniques, e.g., by incubating pertechnate, a reducing agent such as $SNCl_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

In some embodiments, a fluorescent label is or comprises one or more of Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red, among others.

Several methods are known in the art for the attachment or conjugation of an antibody agent to a payload. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948, each incorporated herein by reference). Provided DV antibody agents may also be reacted with an enzyme in the presence of a coupling agent such as glutaraldehyde or periodate. Conjugates with fluorescein markers are prepared in the presence of these coupling agents or by reaction with an isothiocyanate.

Production of Antibodies

Provided antibody agents including antibodies, and/or characteristic portions thereof, or nucleic acids encoding them, may be produced by any available means. Methods for generating antibodies (e.g., monoclonal antibodies and/or polyclonal antibodies) are well known in the art. It will be appreciated that a wide range of animal species can be used for the production of antisera, including rabbit, mouse, rat, hamster, guinea pig or goat. The choice of animal may be decided upon the ease of manipulation, costs or the desired amount of sera, as would be known to one of skill in the art. It will be appreciated that antibody agent can also be produced transgenically through the generation of a mammal or plant that is transgenic for the immunoglobulin heavy and light chain sequences of interest and production of the antibody in a recoverable form therefrom. In connection with the transgenic production in mammals, antibodies can be produced in, and recovered from, the milk of goats, cows, or other mammals. See, e.g., U.S. Pat. Nos. 5,827,690, 5,756,687, 5,750,172, and 5,741,957.

Provided antibody agents (including antibodies and/or characteristic portions) may be produced, for example, by utilizing a host cell system engineered to express an inventive antibody-encoding nucleic acid. Alternatively or additionally, provided antibody agents may be partially or fully prepared by chemical synthesis (e.g., using an automated peptide synthesizer).

Exemplary sources for antibody agent preparations suitable for the invention include, but are not limited to, conditioned culture medium derived from culturing a recombinant cell line that expresses a protein of interest, or from a cell extract of, e.g., antibody-producing cells, bacteria, fungal cells, insect cells, transgenic plants or plant cells, transgenic animals or animal cells, or serum of animals, ascites fluid, hybridoma or myeloma supernatants. Suitable bacterial cells include, but are not limited to, *Escherichia coli* cells. Examples of suitable *E. coli* strains include: HB101, DH5α, GM2929, JM109, KW251, NM538, NM539, and any *E. coli* strain that fails to cleave foreign DNA. Suitable fungal host cells that can be used include, but are not limited to, *Saccharomyces cerevisiae, Pichia pastoris* and *Aspergillus* cells. Suitable insect cells include, but are not limited to, S2 Schneider cells, D. Mel-2 cells, SF9, SF21, High-5™, Mimic™-SF9, MG1 and KCl cells. Suitable exemplary recombinant cell lines include, but are not limited to, BALB/c mouse myeloma line, human retinoblasts (PER.C6), monkey kidney cells, human embryonic kidney line (293), baby hamster kidney cells (BHK), Chinese hamster ovary cells (CHO), mouse sertoli cells, African green monkey kidney cells (VERO-76), human cervical carcinoma cells (HeLa), canine kidney cells, buffalo rat liver cells, human lung cells, human liver cells, mouse mammary tumor cells, TR1 cells, MRC 5 cells, FS4 cells, and human hepatoma line (Hep G2).

Antibody agents of interest can be expressed using various vectors (e.g., viral vectors) known in the art and cells can be cultured under various conditions known in the art (e.g., fed-batch). Various methods of genetically engineering cells to produce antibodies are well known in the art. See e.g. Ausabel et al., eds. (1990), Current Protocols in Molecular Biology (Wiley, New York).

Provided antibody agents may be purified, if desired, using filtration, centrifugation and/or various chromatographic methods such as HPLC or affinity chromatography. In some embodiments, fragments of provided antibody agents are obtained by methods which include digestion with enzymes, such as pepsin or papain, and/or by cleavage of disulfide bonds by chemical reduction.

Nucleic Acids

In certain embodiments, the present invention provides nucleic acids which encode an antibody agent. In some embodiments, the invention provides nucleic acids which are complementary to nucleic acids which encode an antibody agent.

In some embodiments, the invention provides nucleic acid molecules which hybridize to nucleic acids encoding an antibody agent. Such nucleic acids can be used, for example, as primers or as probes. To give but a few examples, such nucleic acids can be used as primers in polymerase chain reaction (PCR), as probes for hybridization (including in situ hybridization), and/or as primers for reverse transcription-PCR(RT-PCR).

In certain embodiments, nucleic acids can be DNA or RNA, and can be single stranded or double-stranded. In some embodiments, nucleic acids may include one or more non-natural nucleotides; In some embodiments, nucleic acids include only natural nucleotides.

Characterization and/or Identification of DV-Related Agents

In some embodiments, the present invention provides antibody agents that can be used to identify and/or characterize one or more agents that mimic an DV epitope or agent and/or induce a strong antibody response to DV.

In some embodiments, such agents include one or more antibody-like binding peptidomimetics. Liu et al. *Cell Mol Biol* (Noisy-le-grand). 2003 March; 49(2):209-16 describe "antibody like binding peptidomimetics" (ABiPs), which are peptides that act as pared-down antibodies and have certain advantages of longer serum half-life as well as less cumbersome synthesis methods. Likewise, in some aspects, antibody-like molecules are cyclic or bicyclic peptides. For example, methods for isolating antigen-binding bicyclic peptides (e.g., by phage display) and for using the such peptides are provided in U.S. Patent Pub. No. 20100317547, incorporated herein by reference.

In some embodiments, such agents include one or more antibody-like binding scaffold proteins. For example, in some embodiments, one or more CDRs arising from an antibody may be grafted onto a protein scaffold. In general, protein scaffolds may meet the greatest number of the following criteria: (Skerra A., *J. Mol. Recogn.*, 2000, 13:167-187): good phylogenetic conservation; known three-dimensional structure (as, for example, by crystallography, NMR spectroscopy or any other technique known to a person skilled in the art); small size; few or no post-transcriptional modifications; and/or easy to produce, express and purify. The origin of such protein scaffolds can be, but is not limited to, fibronectin (e.g., fibronectin type III domain 10), lipocalin, anticalin (Skerra A., *J. Biotechnol.*, 2001, 74(4):257-75), protein Z arising from domain B of protein A of *Staphylococcus aureus*, thioredoxin A or proteins with a repeated motif such as the "ankyrin repeat" (Kohl et al., *PNAS*, 2003, vol. 100, No. 4, 1700-1705), the "armadillo repeat", the "leucine-rich repeat" and the "tetratricopeptide repeat". For example, anticalins or lipocalin derivatives are described in US Patent Publication Nos. 20100285564, 20060058510, 20060088908, 20050106660, and PCT Publication No. WO2006/056464, incorporated herein by reference. Scaffolds derived from toxins such as, for example, toxins from scorpions, insects, plants, mollusks, etc., and the protein inhibitors of neuronal NO synthase (PIN) may also be used in accordance with the present invention.

In some embodiments, such agents include a mimotope, which can be used to disrupt the interaction between an influenza virus and the HA polypeptide receptor. In some embodiment, the mimotope is used to elicit an antibody response identical or similar to the that elicited by its corresponding target epitope. In some embodiments, the target epitope is a sequence that is conserved across more than one DV serotype. In some embodiment, the conserved epitope is a sequence that is conserved across DV serotypes 1-4. In some embodiments, the epitope is a conserved sequence located within the A-strand region of the E glycoprotein. In some embodiments, a mimotope is a peptide. In some embodiments, a mimotope is a small molecule, carbohydrate, lipid, or nucleic acid. In some embodiments, mimotopes are peptide or non-peptide mimotopes of conserved influenza epitopes. In some embodiments, by mimicking the structure of a defined viral epitope, a mimotope interferes with the ability of DV particles to bind to its natural binding partners, e.g., by binding to the natural binding partner itself.

In some embodiments, such an agent is a stapled peptide. In some embodiments, the stapled peptide comprises an amino acid sequences encoding one or more CDRs and/or FRs comprising at least greater than 65, 70, 75, 80, 85, 86, 87, 88, 89, 90, 91, 92, 93, 94, 95, 96, 97, 98 or 99% homology and/or identity with the corresponding CDRs and/or FRs of an anti-DV antibody (e.g., 4E11). In some embodiments, the stapled peptide comprises an amino acid sequence encoding one or more VH and/or VL chain sequence comprising at least greater than 65, 70, 75, 80, 85, 86, 87, 88, 89, 90, 91, 92, 93, 94, 95, 96, 97, 98 or 99% homology and/or identity with the corresponding VH and VL chains of an anti-DV antibody (e.g., 4E11).

In certain embodiments, such an agent is or comprise a nucleic acid, such as DNA or RNA. In certain embodiments, nucleic acids can be DNA or RNA, and can be single stranded or double-stranded. In some embodiments, nucleic acids may include one or more non-natural nucleotides. In some embodiments, nucleic acids include only natural nucleotides. In some embodiments the nucleic acid is designed to mimic an epitope within a DV polypeptide. In some embodiments the nucleic acid is designed to mimic a conserved epitope within one or more DV serotypes. In some embodiments, such an agent is or comprises one or more oligonucleotides. In some embodiments, such an agent is or comprises one or more oligonucleotides comprising a secondary structure such as loop, hairpin, fold or combinations thereof. In some embodiments, such an agent is or comprises one or more oligonucleotides comprising a higher ordered (tertiary or quaternary) structure. In some embodiments, such an agent is or comprises an aptamer.

In some embodiments, a vaccine may be designed to induce production of antibodies that have been found to be lacking in the patient. In some embodiments, it is desirable for vaccine compositions to comprise antigens that have a native conformation, mediate a protective response (e.g., complement activation, virus neutralization, etc.), and/or can induce a strong antibody response. In some embodiments, a vaccine contains an epitope or mimotope thereof to which antibodies are not being produced naturally in the individual. For example, synthetic peptide mimotopes isolated with DV antibodies (e.g., DV antibodies recognizing multiple serotypes) have the potential to induce a potent immune response similar to the antibody used in the original isolation of the mimotope. Administration of such a vaccine might induce a patient's immune system to start producing a set of antibodies directed against the administered epitope. It will be appreciated that the mimotopes (or epitopes) in accordance with the invention can be used alone or in combination with recombinant proteins, inactivated DV virus, killed DV virus, and/or as a cocktail of several different mimotopes.

In some embodiments, vaccines to DV may be utilized for active immunization (i.e., immunization wherein microbes, proteins, peptides, epitopes, mimotopes, etc. are administered to a subject). In some embodiments, vaccines to DV may comprise any agent that mimics at least one conformational epitope of DV A-strand region of DV envelope glycoprotein may be used. For example, the agent may be a peptide, protein, glycopeptide, glycoprotein, small molecule, mimotope, organic compound, lipid, saccharide, organometallic compound, inorganic compound, etc. In some embodiments, epitopes represented in a vaccine include those against which antibodies known to prevent infection are directed. In some embodiments, epitopes represented in a vaccine in accordance with the invention include ones that are conserved among different genotypes and/or subtypes of the virus or among different strains of virus. In some embodiments, peptides or proteins that contain conformationally defined epitopes of A-strand region of DV are used in formulations of a vaccine to prevent, delay onset of, treat, ameliorate symptoms of, and/or reduce severity of infection by DV. In some embodiments, DV A-strand region epitopes may be linear epitopes. In some embodiments, A-strand region epitopes may be a mixture of linear and conformational epitopes. In some embodiments, A-strand region epitopes may be conformational epitopes. In some embodiments, peptide epitopes are less than 100 amino acids in length. In certain embodiments, peptide epitopes are less than 50, less than 40, less than 30, less than 20, or less than 10 amino acids in length. In some embodiments, peptides to be used in formulating a vaccine are peptide fragments of A-strand region protein of DV. Typically, a peptide is used that folds in a manner similar to its three-dimensional fold in the native A-strand region protein, thus preserving the three-dimensional structure of the conformational epitope.

Systems for Identifying and/or Characterizing DV-Binding Agents

The present invention provides a variety of systems for testing, characterizing, and/or identifying DV antibody agents. In some embodiments, provided DV antibody agent are used to identify and/or to characterize other DV-binding agents (e.g., antibodies, polypeptides, small molecules, etc.).

In some embodiments, provided DV-binding agents are characterized by such systems and methods that involve contacting the DV-binding agent with one or more candidate substrates, such as regions of DV polypeptides, N-glycans on DV polypeptides, DV receptors, sialylated DV receptors, and/or glycans on sialylated DV receptors.

In some embodiments, DV-binding agents (e.g., cross reactive antibodies) may be tested, characterized, and/or identified using computational approaches. In some embodiments, a computational approach involves using physicochemical features common to protein-protein (e.g., antibody-antigen) interactions to predict protein-protein interaction and affinity enhancing mutations. Potency of antibodies, for example, produced using this approach in neutralizing DV could then be predicted by various assays known in the art (e.g., plaque reduction neutralization test, ELISA, hemagglutination assay, and Western blot).

In some embodiments, a DV-binding agent and/or candidate substrate may be free in solution, fixed to a support, and/or expressed in and/or on the surface of a cell. The candidate substrate and/or agents may be labeled, thereby permitting detection of binding. Either the DV-binding agent or the candidate substrate is the labeled species. Competitive binding formats may be performed in which one of the substances is labeled, and one may measure the amount of free label versus bound label to determine the effect on binding.

In some embodiments, binding assays involve, for example, exposing a candidate substrate to a DV-binding agent and detecting binding between the candidate substrate and the agent. A binding assay may be conducted in vitro (e.g., in a candidate tube, comprising substantially only the components mentioned; in cell-free extracts; and/or in substantially purified components). Alternatively or additionally, binding assays may be conducted in cyto and/or in vivo (e.g., within a cell, tissue, organ, and/or organism; described in further detail below).

In certain embodiments, at least one DV-binding agent is contacted with at least one candidate substrate and an effect detected. In some embodiments, for example, a DV-binding agent is contacted with a candidate substrate, and binding between the two entities is monitored. In some embodiments, an assay may involve contacting a candidate substrate with a characteristic portion of an agent. Binding of the DV agent to the candidate substrate is detected. It will be appreciated that fragments, portions, homologs, variants, and/or derivatives of DV-binding agents may be employed, provided that they comprise the ability to bind one or more candidate substrates.

Binding of a DV agent to the candidate substrate may be determined by a variety of methods well-known in the art. In some embodiments, binding measurements may be conducted using SPR analysis. In some embodiments, SPR analysis may be used to measure affinity and kinetic binding parameters of a DV-binding agent. In some embodiments, assays involving solid phase-bound DV agents and detecting their interactions with one or more candidate substrates may be used. Thus, a DV-binding agent may comprise a detectable marker, such as a radioactive, fluorescent, and/or luminescent label. Furthermore, candidate substrate can be coupled to substances which permit indirect detection (e.g. by means of employing an enzyme which uses a chromogenic substrate and/or by means of binding a detectable antibody). Changes in the conformation of DV-binding agents as the result of an interaction with a candidate substrate may be detected, for example, by the change in the emission of the detectable marker. Alternatively or additionally, solid phase-bound protein complexes may be analyzed by means of mass spectrometry.

In some embodiments, the DV-binding agent can be non-immobilized. In some embodiments, the non-immobilized component may be labeled (with for example, a radioactive label, an epitope tag, an enzyme-antibody conjugate, etc.). Alternatively or additionally, binding may be determined by immunological detection techniques. For example, the reaction mixture may be subjected to Western blotting and the blot probed with an antibody that detects the non-immobilized component. Alternatively or additionally, ELISA may be utilized to assay for binding. In some embodiments, binding affinity of a DV agent to a candidate substrate may be determined by using a high throughput indirect ELISA assay.

In some embodiments, focus reduction neutralization test (FRNT) assay may be utilized for measuring activity or neutralizing potency of a DV-binding agent. In some embodiments, animal host may be used for measuring anti-DV activity in vivo.

In certain embodiments, cells may be directly assayed for binding between DV agents and candidate substrates. Immunohistochemical techniques, confocal techniques, and/or other techniques to assess binding are well known to those of skill in the art. Various cell lines may be utilized for such screening assays, including cells specifically engineered for this purpose. Examples of cells used in the screening assays include mammalian cells, fungal cells, bacterial cells, or viral cells. A cell may be a stimulated cell, such as a cell stimulated with a growth factor. One of skill in the art would understand that the invention disclosed herein contemplates a wide variety of in cyto assays for measuring the ability of DV-binding agents to bind to candidate substrates.

Depending on the assay, cell and/or tissue culture may be required. A cell may be examined using any of a number of different physiologic assays. Alternatively or additionally, molecular analysis may be performed, including, but not limited to, western blotting to monitor protein expression and/or test for protein-protein interactions; mass spectrometry to monitor other chemical modifications; etc.

In some embodiments, a binding assays described herein may be performed using a range of concentrations of DV-binding agents and/or candidate substrates. In some embodiments, the binding assays described herein are used to assess the ability of a candidate substrate to bind to a DV agent over range of antibody concentrations (e.g. greater than about 100 μg/ml, about 100 μg/ml, about 50 μg/ml, about 40 μg/ml, about 30 μg/ml, about 20 μg/ml, about 10 μg/ml, about 5 μg/ml, about 4 μg/ml, about 3 μg/ml, about 2 μg/ml, about 1.75 μg/ml, about 1.5 μg/ml, about 1.25 μg/ml, about 1.0 μg/ml, about 0.9 μg/ml, about 0.8 μg/ml, about 0.7 μg/ml, about 0.6 μg/ml, about 0.5 μg/ml, about 0.4 μg/ml, about 0.3 μg/ml, about 0.2 μg/ml, about 0.1 μg/ml, about 0.05 μg/ml, about 0.01 μg/ml, and/or less than about 0.01 μg/ml).

In some embodiments, any of the binding studies described herein can be executed in a high throughput fashion. Using high throughput assays, it is possible to screen up to several thousand agents in a single day. In some embodiments, each well of a microtiter plate can be used to run a separate assay against a selected candidate substrate, or, if concentration and/or incubation time effects are to be observed, every 5-10 wells can test a single candidate substrate. Thus, a single standard microtiter plate can assay up to 96 binding interactions between agents and candidate substrates; if 1536 well plates are used, then a single plate can assay up to 1536 binding interactions between agents and candidate substrates; and so forth. It is possible to assay many plates per day. For example, up to about 6,000, about 20,000, about 50,000, or more than about 100,000 assay screens can be performed on binding interactions between antibodies and candidate substrates using high throughput systems in accordance with the present invention.

In some embodiments, such methods utilize an animal host. As used herein, an "animal host" includes any animal model suitable for influenza research. For example, animal hosts suitable for the invention can be any mammalian hosts, including primates, ferrets, cats, dogs, cows, horses, rodents such as, mice, hamsters, rabbits, and rats. In certain embodiments, an animal host used for the invention is a ferret. In particular, in some embodiments, an animal host is naïve to viral exposure or infection prior to administration of an agent (optionally in an inventive composition). In some embodiments, the animal host is inoculated with, infected with, or otherwise exposed to virus prior to or concurrent with administration of an agent. An animal host used in the practice of the present invention can be inoculated with, infected with, or otherwise exposed to virus by any method known in the art. In some embodiments, an animal host may be inoculated with, infected with, or exposed to virus intranasally.

Naïve and/or inoculated animals may be used for any of a variety of studies. For example, such animal models may be used for virus transmission studies as in known in the art. It is contemplated that the use of ferrets in virus transmission studies may serve as a reliable predictor for virus transmission in humans. Virus transmission studies may be used to test agents. For example, DV-binding agents may be administered to a suitable animal host before, during or after virus transmission studies in order to determine the efficacy of said agent in blocking virus binding and/or infectivity in the animal host. Using information gathered from virus transmission studies in an animal host, one may predict the efficacy of an agent in blocking virus binding and/or infectivity in a human host.

Pharmaceutical Compositions

The present invention provides compositions comprising one or more provided antibody agents. In some embodiments the present invention provides at least one antibody and at least one pharmaceutically acceptable excipient. Such pharmaceutical compositions may optionally comprise and/or be administered in combination with one or more additional therapeutically active substances. In some embodiments, provided pharmaceutical compositions are useful in medicine. In some embodiments, provided pharmaceutical compositions are useful as prophylactic agents (i.e., vaccines) in the treatment or prevention of DV infection or of negative ramifications associated or correlated with DV infection. In some embodiments, provided pharmaceutical compositions are useful in therapeutic applications, for example in individuals suffering from or susceptible to DV infection. In some embodiments, pharmaceutical compositions are formulated for administration to humans.

For example, pharmaceutical compositions provided herein may be provided in a sterile injectible form (e.g., a form that is suitable for subcutaneous injection or intravenous infusion). For example, in some embodiments, pharmaceutical compositions are provided in a liquid dosage form that is suitable for injection. In some embodiments, pharmaceutical compositions are provided as powders (e.g. lyophilized and/or sterilized), optionally under vacuum, which are reconstituted with an aqueous diluent (e.g., water, buffer, salt solution, etc.) prior to injection. In some embodiments, pharmaceutical compositions are diluted and/or reconstituted in water, sodium chloride solution, sodium acetate solution, benzyl alcohol solution, phosphate buffered saline, etc. In some embodiments, powder should be mixed gently with the aqueous diluent (e.g., not shaken).

In some embodiments, provided pharmaceutical compositions comprise one or more pharmaceutically acceptable excipients (e.g., preservative, inert diluent, dispersing agent, surface active agent and/or emulsifier, buffering agent, etc.). In some embodiments, pharmaceutical compositions comprise one or more preservatives. In some embodiments, pharmaceutical compositions comprise no preservative.

In some embodiments, pharmaceutical compositions are provided in a form that can be refrigerated and/or frozen. In some embodiments, pharmaceutical compositions are provided in a form that cannot be refrigerated and/or frozen. In some embodiments, reconstituted solutions and/or liquid dosage forms may be stored for a certain period of time after reconstitution (e.g., 2 hours, 12 hours, 24 hours, 2 days, 5 days, 7 days, 10 days, 2 weeks, a month, two months, or longer).

Liquid dosage forms and/or reconstituted solutions may comprise particulate matter and/or discoloration prior to administration. In some embodiments, a solution should not be used if discolored or cloudy and/or if particulate matter remains after filtration.

Formulations of the pharmaceutical compositions described herein may be prepared by any method known or hereafter developed in the art of pharmacology. In some embodiments, such preparatory methods include the step of bringing active ingredient into association with one or more excipients and/or one or more other accessory ingredients, and then, if necessary and/or desirable, shaping and/or packaging the product into a desired single- or multi-dose unit.

A pharmaceutical composition in accordance with the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to a dose which would be administered to a subject and/or a convenient fraction of such a dose such as, for example, one-half or one-third of such a dose.

Relative amounts of active ingredient, pharmaceutically acceptable excipient, and/or any additional ingredients in a pharmaceutical composition in accordance with the invention may vary, depending upon the identity, size, and/or condition of the subject treated and/or depending upon the route by which the composition is to be administered. By way of example, the composition may comprise between 0.1% and 100% (w/w) active ingredient.

Pharmaceutical compositions of the present invention may additionally comprise a pharmaceutically acceptable excipient, which, as used herein, may be or comprise solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's The Science and Practice of Pharmacy, 21st Edition, A. R. Gennaro, (Lippincott, Williams & Wilkins, Baltimore, Md., 2006) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

Vaccines

In some embodiments, the present invention provides vaccine compositions for use, and/or for exam in passive immunization (i.e., immunization wherein antibodies are administered to a subject) of a subject who is suffering from or susceptible to DV infection. In some embodiments, passive immunization occurs when antibodies are transferred from mother to fetus during pregnancy. In some embodiments, passive immunization includes administration of antibody agents directly to an individual (e.g., by injection, orally, nasally, etc.).

In some embodiments, prophylactic applications may include administering vaccines. In some embodiments, vaccination is tailored to the individual patient. For example, as described below, serum may be collected from a patient and tested for presence of DV, and in some embodiments for one or more particular DV serotypes. In some embodiments, appropriate recipients of provided vaccines are individuals suffering from or susceptible to infection with one or more DV serotypes bound and/or neutralized by a provided antibody.

In some embodiments, a vaccine is administered orally, intranasally, subcutaneously, intramuscularly, intradermally, or via any other medically-appropriate route of administration. It will be appreciated that each route of administration may require distinct formulations or delivery mechanisms and such variable parameters are contemplated as within the scope of the present invention. In some embodiments, the route of administration and/or formulation may be dictated in part by the age and/or condition of the subject. For example, administration of a vaccine to a baby may be performed via injection to the anterolateral aspect of the thigh, due to the large muscle mass. In some embodiments, where the subject is a child or an adult, administration of a vaccine to the deltoid muscle may be preferred. It is understood that sounds medical judgment should be used to determine the proper route and/or formulation for administration to a particular subject.

In some embodiments, a vaccine composition comprises at least one adjuvant. Any adjuvant may be used in accordance with the present invention. A large number of adjuvants are known; a useful compendium of many such compounds is prepared by the National Institutes of Health and can be found on www.niaid.nih.gov/daids/vaccine/pdf/compendium.pdf; see also Allison (1998, Dev. Biol. Stand., 92:3-11; incorporated herein by reference), Unkeless et al. (1998, Annu Rev. Immunol., 6:251-281; incorporated herein by reference), and Phillips et al. (1992, Vaccine, 10:151-158; incorporated herein by reference). Hundreds of different adjuvants are known in the art and could be employed in the practice of the present invention. Exemplary adjuvants that can be utilized in accordance with the invention include, but are not limited to, cytokines, gel-type adjuvants (e.g., aluminum hydroxide, aluminum phosphate, calcium phosphate, etc.); microbial adjuvants (e.g., immunomodulatory DNA sequences that include CpG motifs; endotoxins such as monophosphoryl lipid A; exotoxins such as cholera toxin, *E. coli* heat labile toxin, and pertussis toxin; muramyl dipeptide, etc.); oil-emulsion and emulsifier-based adjuvants (e.g., Freund's Adjuvant, MF59 [Novartis], SAF, etc.); particulate adjuvants (e.g., liposomes, biodegradable microspheres, saponins, etc.); synthetic adjuvants (e.g., nonionic block copolymers, muramyl peptide analogues, polyphosphazene, synthetic polynucleotides, etc.); and/or combinations thereof. Other exemplary adjuvants include some polymers (e.g., polyphosphazenes; described in U.S. Pat. No. 5,500,161, which is incorporated herein by reference), Q57, QS21, squalene, tetrachlorodecaoxide, etc. Pharmaceutically acceptable excipients have been previously described in further detail in the above section entitled "Pharmaceutical Compositions."

Combination Therapy

It will be appreciated that DV antibody agents in accordance with the present invention and/or pharmaceutical compositions thereof can be employed in combination therapies. By "in combination with," it is not intended to imply that the agents must be administered at the same time and/or formulated for delivery together, although these methods of delivery are within the scope of the invention. Compositions can be administered concurrently with, prior to, or subsequent to, one or more other desired therapeutics or medical procedures. In will be appreciated that therapeutically active agents utilized in combination may be administered together in a single composition or administered separately in different compositions. In general, each agent will be administered at a dose and/or on a time schedule determined for that agent.

The particular combination of therapies (e.g., therapeutics or procedures) to employ in a combination regimen will take into account compatibility of the desired therapeutics and/or procedures and the desired therapeutic effect to be achieved. It will also be appreciated that pharmaceutical compositions of the present invention can be employed in combination therapies (e.g., combination vaccine therapies), that is, the pharmaceutical compositions can be administered concurrently with, prior to, or subsequent to, one or more other desired therapeutic and/or vaccination procedures.

Therapeutically effective amounts of antibody agents in accordance with the invention combined with for use in combination with a provided pharmaceutical composition and at least one other active ingredient. In some embodiments, an active ingredient is an anti-viral agent, such as, but not limited to, interferons (e.g., interferon α-2b, interferon-γ, etc.), anti-DV monoclonal antibodies, anti-DV polyclonal antibodies, RNA polymerase inhibitors, protease inhibitors, helicase inhibitors, immunomodulators, antisense compounds, short interfering RNAs, short hairpin RNAs, micro RNAs, RNA aptamers, ribozymes, and combinations thereof. The particular combination of therapies to employ in a combination regimen will generally take into account compatibility of the desired therapeutics and/or procedures and the desired therapeutic effect to be achieved. It will also be appreciated that the therapies and/or vaccines employed may achieve a desired effect for the same disorder (for example, an inventive antigen may be administered concurrently with another DV vaccine), or they may achieve different effects.

It will be appreciated that the therapies employed may achieve a desired effect for the same purpose (for example, DV antibodies useful for treating, preventing, and/or delaying the onset of DV infection may be administered concurrently with another agent useful for treating, preventing, and/or delaying the onset of DV infection), or they may achieve different effects (e.g., control of any adverse effects). The invention encompasses the delivery of pharmaceutical compositions in combination with agents that may improve their bioavailability, reduce and/or modify their metabolism, inhibit their excretion, and/or modify their distribution within the body.

In some embodiments, agents utilized in combination with be utilized at levels that do not exceed the levels at which they are utilized individually. In some embodiments, the levels utilized in combination will be lower than those utilized individually.

In some embodiments, DV antibodies in accordance with the invention may be administered with interferon, with RNA polymerase inhibitors, or with both interferon and RNA polymerase inhibitors.

In some embodiments, combination therapy may involve administrations of a plurality of antibody agents directed to a single epitope (e.g. a single conformational epitope). In some embodiments, combination therapy can comprise a plurality of antibody agents that recognize distinct epitopes (e.g., on the same viral envelope protein or on different viral envelope proteins, where epitopes may or may not be conformational), for example to simultaneously interfere with multiple mechanisms in the infectious process.

In certain embodiments, compositions in accordance with the invention comprise exactly one antibody agent to A-strand region. In certain embodiments, compositions include and/or combination therapy utilize exactly two DV A-strand region antibody agents.

It will be appreciated by one of skill in the art that any permutation or combination of antibody agents in accordance with the present invention can be combined with any other antibody agent to formulate compositions and/or combination therapy regimens comprising a plurality of different antibody agents.

Methods of Administration

DV antibody agents in accordance with the invention and pharmaceutical compositions thereof in accordance with the present invention may be administered according to any appropriate route and regimen. In some embodiments, a route or regimen is one that has been correlated with a positive therapeutic benefit. In some embodiments, a route or regimen is one that has been approved by the FDA and/or EP.

In some embodiments, the exact amount administered may vary from subject to subject, depending on one or more factors as is well known in the medical arts. Such factors may include, for example, one or more of species, age, general condition of the subject, severity of the infection, particular composition, its mode of administration, its mode of activity, the disorder being treated and the severity of the disorder; the activity of the specific DV antibody agent employed; the specific pharmaceutical composition administered; the half-life of the composition after administration; the age, body weight, general health, sex, and diet of the subject; the time of administration, route of administration, and rate of excretion of the specific compound employed; the duration of the treatment; drugs used in combination or coincidental with the specific compound employed and the like. Pharmaceutical compositions may be formulated in dosage unit form for ease of administration and uniformity of dosage. It will be understood, however, that the total daily usage of the compositions of the present invention will be decided by the attending physician within the scope of sound medical judgment.

Pharmaceutical compositions of the present invention may be administered by any route, as will be appreciated by those skilled in the art. In some embodiments, pharmaceutical compositions of the present invention are administered by oral (PO), intravenous (IV), intramuscular (IM), intra-arterial, intramedullary, intrathecal, subcutaneous (SQ), intraventricular, transdermal, interdermal, intradermal, rectal (PR), vaginal, intraperitoneal (IP), intragastric (IG), topical (e.g., by powders, ointments, creams, gels, lotions, and/or drops), mucosal, intranasal, buccal, enteral, vitreal, sublingual; by intratracheal instillation, bronchial instillation, and/or inhalation; as an oral spray, nasal spray, and/or aerosol, and/or through a portal vein catheter.

In specific embodiments, DV antibody agents in accordance with the present invention and/or pharmaceutical compositions thereof may be administered intravenously, for example, by intravenous infusion. In specific embodiments, DV antibody agents in accordance with the present invention and/or pharmaceutical compositions thereof may be administered by intramuscular injection. In specific embodiments, DV antibody agents in accordance with the present invention and/or pharmaceutical compositions thereof may be administered by subcutaneous injection. In specific embodiments, DV antibody agents in accordance with the present invention and/or pharmaceutical compositions thereof may be administered via portal vein catheter. However, the invention encompasses the delivery of DV antibody agents in accordance with the present invention and/or pharmaceutical compositions thereof by any appropriate route taking into consideration likely advances in the sciences of drug delivery.

In certain embodiments, DV antibody agents in accordance with the present invention and/or pharmaceutical compositions thereof in accordance with the invention may be administered at dosage levels sufficient to deliver from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg of subject body weight per day to obtain the desired therapeutic effect. The desired dosage may be delivered more than three times per day, three times per day, two times per day, once per day, every other day, every third day, every week, every two weeks, every three weeks, every four weeks, every two months, every six months, or every twelve months. In certain embodiments, the desired dosage may be delivered using multiple administrations (e.g., two, three, four, five, six, seven, eight, nine, ten, eleven, twelve, thirteen, fourteen, or more administrations).

Prophylactic Applications

In some embodiments, DV antibody agents in accordance with the invention may be utilized for prophylactic applications. In some embodiments, prophylactic applications involve systems and methods for preventing, inhibiting progression of, and/or delaying the onset of DV infection, and/or any other DV-associated condition in individuals susceptible to and/or displaying symptoms of DV infection. In some embodiments, prophylactic applications involve systems and methods for preventing, inhibiting progression of, and/or delaying the onset of infection of the brain. In some embodiments, prophylactic applications involve systems and methods for preventing, inhibiting progression of, and/or delaying the impairment of vital organs (e.g., liver).

Diagnostic Applications

In some embodiments, DV antibody agents in accordance with the invention are used for diagnostic applications. For example, by virtue of the variety of binding profiles of DV antibody agents, diagnostic assays may be employed which will detect a plurality of DV serotypes, so as to provide a pan-DV antibody agent, while at the same time being able to dissect individual serotypes by subtractive analysis.

For diagnostic purposes, antibody agents may be used in a wide variety of formats for detecting A-strand region of envelope glycoprotein, discerning DV serotypes, detecting virions and antibodies (see, e.g., U.S. Pat. No. 5,695,390; incorporated herein by reference). Antibody agents may be used individually or in combination with other antibodies of the subject group or other antibodies or with lectins which bind to the glycosyl groups present on DV envelope proteins. For diagnostic purposes, a wide variety of labels may be employed, which for the most part have been mentioned previously. These include, but are not limited to, fluorophores, chemiluminescent moieties, radioisotopes, enzymes, particles (e.g., colloidal carbon particles, gold particles, latex particles, etc.) ligands for which there are high affinity receptors, and prolabels, which can be activated to provide a detectable signal.

In some embodiments, a surface is coated with a protein, which can bind to DV antigens as free protein (e.g., circulating proteins) or as part of an intact or partially intact virion. One may use antibodies of the subject invention which bind to multiple DV serotypes or to lectins (e.g., Galanthus nivalis lectin; "GNA").

In some embodiments, assays may involve contacting a surface with a medium, which may contain free or DV-associated protein(s), where the medium may be the sample or a solution of known A-strand region of one or more serotypes. After incubation and washing to remove non-specifically bound protein, the assay may proceed in various manners depending upon what is being assayed. Where a blood sample suspected of being seropositive is being assayed, the sample may be applied to the layer of A-strand region protein, incubated, and washed, and the presence of human antibodies bound to the protein layer determined. One may use labeled α-human antibodies (other than against the isotype of the subject antibodies, where the subject antibodies have been initially used). In assays for antibodies in seropositive subjects, subject antibodies may be used as controls with the same reagent used to detect any human anti-DV antibodies in the sera of such subjects. The specificity of the antibodies in the sample can be confirmed by using the subject antibodies, which are differentially labeled from the anti-human antibodies and determine whether they are blocked by the antibodies in the sample.

Where the sample is assayed for DV A-strand region protein, detection employs labeled subject antibodies, the selection depending upon whether one is interested in genotyping or detection of A-strand region protein. After washing away non-specifically bound antibody, the presence of labeled antibodies is determined by detecting the presence of the label in accordance with known techniques. Alternatively or additionally, where the subject antibodies are bound to a surface, a labeled lectin for A-strand region may be employed to detect the presence of A-strand region protein.

Antibody agents in accordance with the invention can be used to measure the reactivity of other antibodies, including antibodies in sera, monoclonal antibodies, antibodies expressed as a result of genetic engineering, etc. In some embodiments, intact virions are used. In some embodiments, conformationally conserved envelope proteins are used. For virion capture, see, for example, Kimura et al., 1998, J. Med. Virology, 56:25-32; Morita et al., 1996, Hapato-Gastroenterology, 43:582-585; Sata et al., 1993, Virology, 196:354-357; and Hijikata et al., 1993, J. Virol., 67:1953-1958; all of which are incorporated herein by reference. One protocol involves steps of coating a solid support with a lectin (e.g., GNA) and then contacting the surface with a medium (e.g., serum of a seropositive patient) comprising intact DV virions. Additives which might destroy virions should usually be avoided (e.g., detergents). After incubating the medium and washing to remove non-specifically bound components of the medium, virions may be contacted with antibodies in accordance with the invention and antibodies of the sample. This may be performed concurrently or consecutively, where the sample is added first. An amount of the subject antibody is used which is sensitive to displacement by another antibody. Such amount may be determined empirically, and one may wish to use different amounts of the subject antibody in a series of tests. By knowing the signal, which is obtained in the absence and presence of the sample, one can determine the reactivity or binding affinity of the antibodies in the sample. Various techniques may be used to determine the amount of a subject antibody bound to the virions. Where the subject antibodies are labeled, e.g., with biotin or digoxigenin, streptavidin or anti-digoxigenin labeled with a fluorophore or enzyme whose substrate produces a detectable signal can serve to determine the amount of the subject antibodies.

Labeled subject antibody agents may be used in assaying for the presence of DV from biopsy material. Labeled antibody may be incubated with immobilized biopsy material, such as a liver slice, with a solution of one or more of the subject labeled antibodies. After washing away non-specifically bound antibodies, the presence of the antibodies bound to the cells of the biopsied tissue may be detected in accordance with the nature of the label.

In some embodiments, DV antibody agents in accordance with the invention can be used to identify DV receptors. Those skilled in the art will appreciate the multitude of ways this can be accomplished (Sambrook J., Fritsch E. and Maniatis T. Molecular Cloning: A Laboratory Manual. Cold Spring Harbor Press, Cold Spring Harbor, N.Y., 1989; and Ausubel et al., eds., Current Protocols in Molecular Biology, 1987; both of which are incorporated herein by reference). Typically, protein and peptide receptors can be identified by determining whether an antibody to A-strand region of DV envelope glycoprotein can inhibit attachment of DV virions to a cell susceptible to DV infection. Thus, receptors for DV A-strand region proteins and peptides can be identified in this manner. A susceptible cell can be incubated in the presence of DV and anti-DV A-strand region antibody, and a cell-binding assay can be utilized to determine whether attachment is decreased in the presence of the antibody.

Cells expressing putative receptors for DV and/or libraries of putative receptors for DV may be screened for their abilities to bind DV. For example, cells expressing a putative DV receptor (e.g., a receptor for DV A-strand region) can be contacted with an DV protein or peptide in the presence of an antibody for a time and under conditions sufficient to allow binding of the DV protein or peptide to putative receptor on the surface of the cell. Alternatively or additionally, DV proteins, peptides, or virions can be pre-incubated with antibody prior to contacting the putative receptor on the cell surface. Binding can be detected by any means known in the art, e.g., flow cytometry etc. (see Ausubel et al. or Sambrook et al., supra). A decrease in binding to the surface of the cell in the presence of antibody compared to binding in the absence of the cell in the absence of the antibody indicates the identification of an DV receptor.

In some embodiments, methods of identifying DV receptors include the use of solid supports, such as beads, columns, and the like. For example, receptors for DV proteins and peptides (e.g., A-strand region proteins and/or fragments thereof) and/or DV virions can be identified by attaching an DV antibody to a solid support and then contacting the antibody with an DV protein or peptide for a time sufficient for the DV protein or peptide to bind to the antibody. This provides an DV protein ligand for putative DV receptors that can be contacted with the antibody:ligand complex on the solid support for a time and under conditions sufficient to allow binding of a receptor to the DV protein or peptide. Proteins can be expressed from a library or provided as a cell extract or purified protein preparation from natural or recombinant cells. Once specific binding complexes between the DV protein peptide are formed, unbound DV proteins or peptides, e.g., library proteins or peptide that did not bind specifically to the DV proteins or peptides, are removed, e.g., by standard washing steps. Bound proteins are then eluted and identified, e.g., by gel electrophoresis.

Kits

The invention provides a variety of kits for conveniently and/or effectively carrying out methods in accordance with the present invention. Kits typically comprise one or more DV antibody agents in accordance with the invention. In some embodiments, kits comprise a collection of different DV antibody agents to be used for different purposes (e.g., diagnostics, treatment, and/or prophylaxis). Typically kits will comprise sufficient amounts of DV antibody agents to allow a user to perform multiple administrations to a subject(s) and/or to perform multiple experiments. In some embodiments, kits are supplied with or include one or more DV antibody agents that have been specified by the purchaser.

In certain embodiments, kits for use in accordance with the present invention may include one or more reference samples; instructions (e.g., for processing samples, for performing tests, for interpreting results, for solubilizing DV antibody agents, for storage of DV antibody agents, etc.); buffers; and/or other reagents necessary for performing tests. In certain embodiments kits can comprise panels of antibodies. Other components of kits may include cells, cell culture media, tissue, and/or tissue culture media.

Kits may comprise instructions for use. For example, instructions may inform the user of the proper procedure by which to prepare a pharmaceutical composition comprising DV antibody agents and/or the proper procedure for administering pharmaceutical compositions to a subject.

In some embodiments, kits include a number of unit dosages of a pharmaceutical composition comprising DV antibody agents. A memory aid may be provided, for example in the form of numbers, letters, and/or other markings and/or with a calendar insert, designating the days/times in the treatment schedule in which dosages can be administered. Placebo dosages, and/or calcium dietary supplements, either in a form similar to or distinct from the dosages of the pharmaceutical compositions, may be included to provide a kit in which a dosage is taken every day.

Kits may comprise one or more vessels or containers so that certain of the individual components or reagents may be separately housed. Kits may comprise a means for enclosing the individual containers in relatively close confinement for commercial sale, e.g., a plastic box, in which instructions, packaging materials such as styrofoam, etc., may be enclosed.

In some embodiments, kits are used in the treatment, diagnosis, and/or prophylaxis of a subject suffering from and/or susceptible to DV. In some embodiments, such kits comprise (i) at least one DV antibody agent; (ii) a syringe, needle, applicator, etc. for administration of the at least one DV antibody agent to a subject; and (iii) instructions for use.

In some embodiments, kits are used in the treatment, diagnosis, and/or prophylaxis of a subject suffering from and/or susceptible to DV. In some embodiments, such kits comprise (i) at least one DV antibody agent provided as a lyophilized powder; and (ii) a diluent for reconstituting the lyophilized powder. Such kits may optionally comprise a syringe, needle, applicator, etc. for administration of the at least one DV antibody agent to a subject; and/or instructions for use.

The present invention provides kits containing reagents for the generation of vaccines comprising at least one DV antibody agent. In some embodiments, such kits may include cells expressing DV antibodies, characteristic portions thereof, and/or biologically active portions thereof; (ii) media for growing the cells; and (iii) columns, resin, buffers, tubes, and other tools useful for antibody purification. In some embodiments, such kits may include (i) plasmids containing nucleotides encoding DV antibodies, characteristic portions thereof, and/or biologically active portions thereof; (ii) cells capable of being transformed with the plasmids, such as mammalian cell lines, including but not limited to, Vero and MDCK cell lines; (iii) media for growing the cells; (iv) expression plasmids containing no nucleotides encoding DV antibodies as negative controls; (v) columns, resin, buffers, tubes, and other tools useful for antibody purification; and (vi) instructions for use.

In some embodiments, kits are used to detect the presence of DV in one or more samples. Such samples may be pathological samples, including, but not limited to, blood, serum/plasma, peripheral blood mononuclear cells/peripheral blood lymphocytes (PBMC/PBL), sputum, urine, feces, throat swabs, dermal lesion swabs, cerebrospinal fluids, cervical smears, pus samples, food matrices, and tissues from various parts of the body such as brain, spleen, and liver. Such samples may be environmental samples, including, but not limited to, soil, water, and flora. Other samples that have not been listed may also be applicable. In some embodiments, such kits comprise (i) at least one DV antibody; (ii) a sample known to contain DV, as a positive control; and (iii) a sample known not to contain DV, as a negative control; and (iv) instructions for use.

In some embodiments, kits are used to neutralize DV in one or more samples. Such kits may provide materials needed to treat an DV-containing sample with at least one DV antibody agent and to test the ability of the treated sample to infect cultured cells relative to untreated sample. Such kits may include (i) at least one DV antibody agent; (ii) cells capable of being cultured and infected with DV; (iii) an antibody that is incapable of binding to and neutralizing DV, as a negative control; (iv) an antibody that is capable of binding to and neutralizing DV, as a positive control; (v) a sample known not to contain DV, as a negative control; (vi) a sample known to contain DV, as a positive control; and (vii) instructions for use.

EXAMPLES

The present invention will be better understood in connection with the following Examples. However, it should be understood that these examples are for illustrative purposes only and are not meant to limit the scope of the invention. Various changes and modifications to the disclosed embodiments will be apparent to those skilled in the art and such changes and modifications including, without limitation, those relating to the formulations and/or methods of the invention may be made without departing from the spirit of the invention and the scope of the appended claims.

Example 1

Prediction of Protein-Protein Complex Structure by Analyzing Physicochemical Features of the Interaction Studies in this Example illustrate the development and use of key physicochemical features to model a protein-protein (e.g., antigen-antibody) interaction. Analysis in this Example assists in distinguishing accurate native-like structures for an antigen-antibody interaction from inaccurate structures and thus, helps in overcoming the limitations of using only energetic functions to rank poses, as performed in modeling of protein-protein interaction using computational docking models. Furthermore, the failure to identify the native pose of nine test cases analyzed in this Example, highlights the limitations of the current search algorithm and the challenges associated with designing affinity enhancing mutations for antigen-antibody complexes.

To capture as many geometrical and chemical properties that form the basis of a molecular recognition, thirteen atomic level features: seven chemical and six physical (Table 1) were used to describe an antigen-antibody interface. Further, a data set comprising of 77 non-redundant 3D structures of antigen-antibody complexes was assembled (see Methods section) and split into two parts, a training set consisting of 40 structures and a test set consisting of the remaining 37 structures. Corresponding to each structure, 100 decoy models were constructed using computational docking (see Methods section), yielding a total of 7,777 structures (7,700 decoy+77x-ray). In the training phase, multivariate logistic regression analysis (MLR) was used to determine the relationship between each feature (explanatory variable) and the degree to which it can successfully discriminate x-ray versus decoys poses (outcome variable). This analysis assisted in achieving a subset of all the explanatory variables that could be combined to predict the value of the outcome variable. Input features generated from each PDB file (and its decoys) were represented as standardized Z-scores to prevent non-uniform learning, which can lead to over (or under) estimation of significance. For the prediction phase, the pre-computed significant features were employed to predict the probability that a structure in the test data set is native-like.

The results from MLR analysis suggested that the relative dominance of individual features affecting the probability of accurately discriminating native versus decoy structures was in the order of ZEPII>main chain-main chain H-bonds>density of H-bonds>percentage of charged groups>density of cation-pi interactions>buried surface area>percentage of neutral polar groups>density of ionic bonds. Each of the above features was found to be significant at an alpha level of 0.05. Based on the logistic regression coefficients, H-bond and ionic bond density, main chain-main chain H-bonds and buried surface area appear to be over-estimated in the docked models. This is anticipated since increasing the values of the above features tends to maximize the scoring function. On the contrary, ZEPII, cation-pi interactions, percentage of charged and neutral polar groups appear to be under-represented in the docked models. Cation-pi interactions, percentage of charged and neutral polar groups do not contribute significantly to the energy scoring function; hence these features were not optimized in the docked interfaces. Further, assessment of docked models shows that docking procedure does not faithfully recapitulate the pairwise interactions common to dissociable antigen-antibody complexes; hence the mock interfaces were found to have low ZEPII values.

Figure 2:
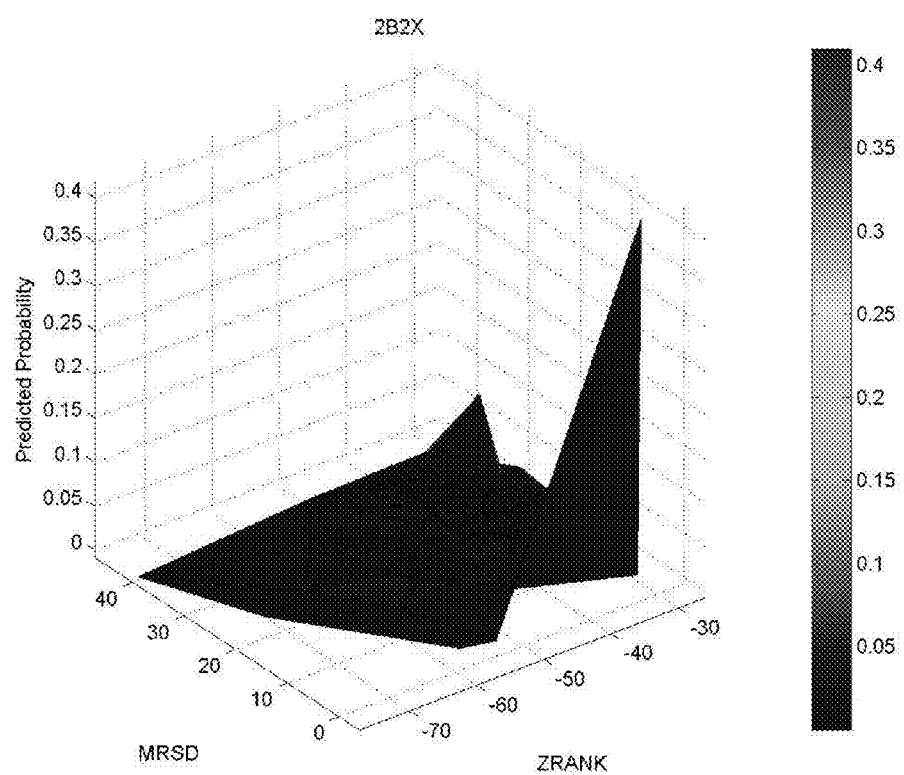
FIGS. 2A-C illustrate docking results of a local search. For this assessment, native-like structures are defined as having less that 3 angstroms (Å) RMSD from the ligand in the x-ray structure, calculated for ligand atoms that are within 7 Å of the fixed receptor. Structures that have RMSD>3 Å are referred as non-native structures. (A) Each point on the surface plot represents a docking decoy. The x-axis shows the ZRANK score; the Y-axis represents RMSD (in Å) to the X-ray structure; the Z axis represents MLR based prediction probabilities. ZRANK scores of native-like structures vary between −60 to −30 Kcal/mol. (B) Correlation between ZRANK scores α-axis) and RMSD (y-axis). Data points inside dotted circles are close to native x-ray structure. (C) Correlation between MLR-based probability and RMSD. There is a significant correlation between prediction probabilities vs. RMSD but no such correlation exists between ZRANK and RMSD.
Figure 2:
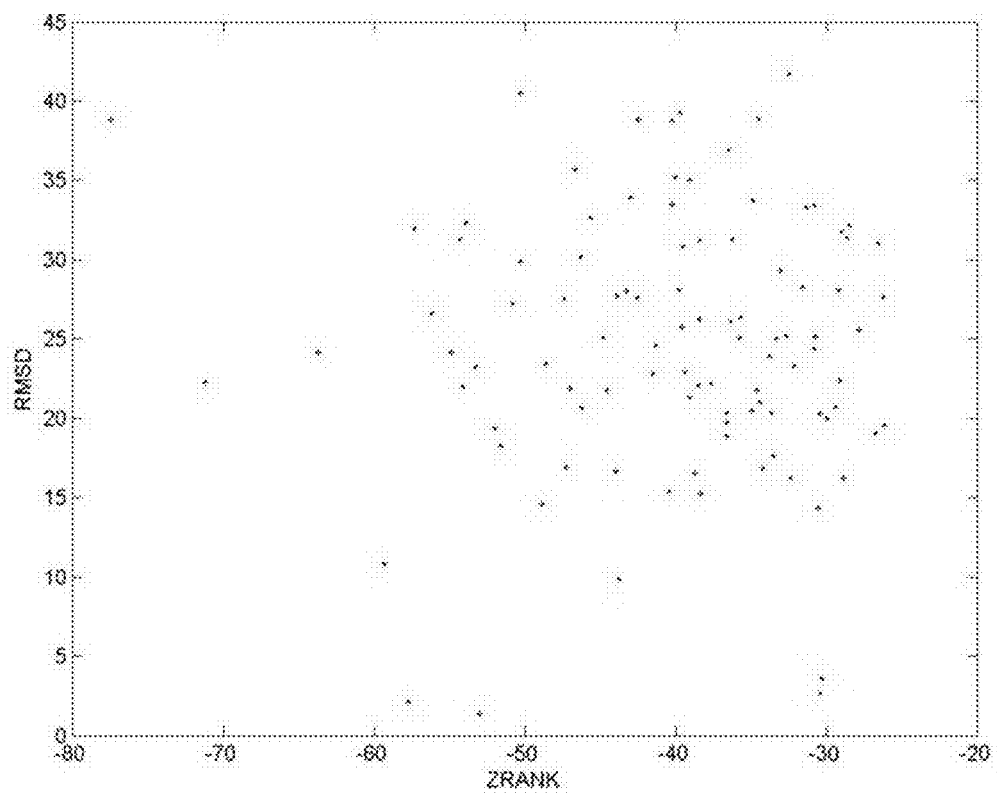
Figure 2C:
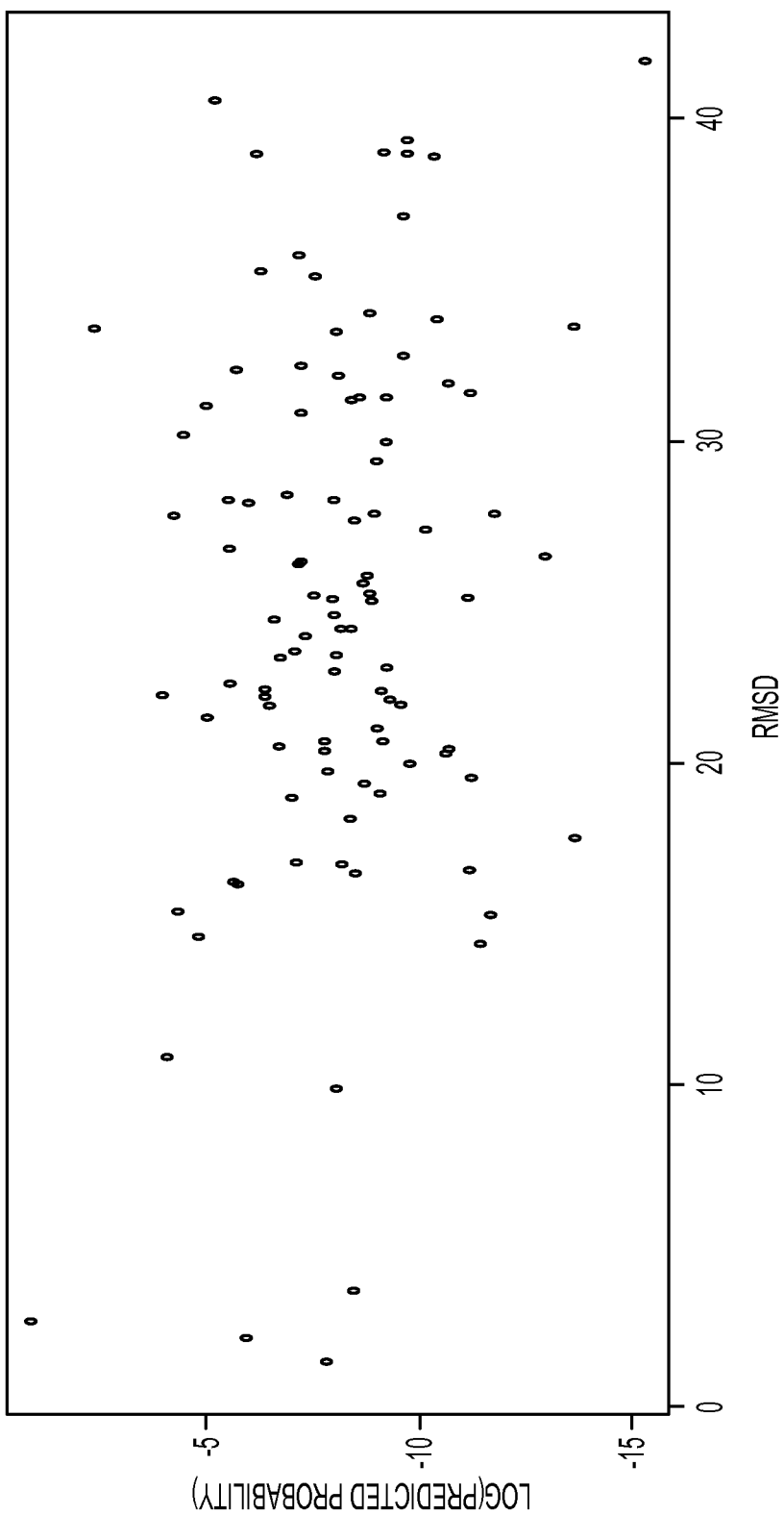

Next, MLR was used to predict x-ray structures of 37 antigen-antibody interactions in the test data set using the pre-computed significant features, and then the sensitivity of the MLR-based prediction was compared to those of the ZRANK energy function, used in docked models (see Methods section). Overall, MLR was shown to be better at predicting x-ray structures than ZRANK energy function (FIG. 1), suggesting that MLR approach yielded improvements over ZRANK in predicting native-like binding poses. Closer examination of the decoy models, their ZRANK scores and MLR-based prediction probabilities revealed interesting insights (FIG. 2). ZDOCK identified native-like structures for 29 out of the 37 structures indicating that computational search algorithms to be very accurate. However, (1) ZRANK score varied significantly even between structurally similar poses (FIG. 2A); (2) very different structures could receive approximately the same score making it difficult to discriminate accurate from inaccurate solutions (FIG. 2A); (3) worse, inaccurate solutions often received better score than native-like structures (FIG. 2A); (4) while MLR-based prediction probability also varied between structurally similar poses, non-native poses rarely received high prediction probability indicating that the likelihood of a false positive structure prediction was lower when the poses are ranked according to prediction probability. Accordingly, prediction probability was seen to correlate better with RMSD when compared to ZRANK score (FIGS. 2B & 2C).

Example 2

Using Physicochemical Features for Prediction of Affinity-Enhancing Mutations

Studies in this Example show the development of a scoring scheme for designing affinity enhancing mutations for protein-protein (e.g., antigen-antibody) interactions.

Specifically, this Example describes a mathematical model developed to quantify the propensities of pairwise amino acid interactions (see Methods section). These statistical propensities were formulated as an interaction matrix that assigns a weight to each possible pair of amino acids. The fitness of a residue at a CDR position, also called the amino acid interface fitness (AIF), was the combined propensity of all inter-protein pairwise contacts (defined as two amino acids within a certain distance of each other) involving that residue. Substitutions that lead to an improvement in AIF value without any structural consequences were considered as candidates for affinity enhancement. The propensities were determined using statistics on amino acid contacts in a database of known protein structures (see Methods section). Avoiding multiple distance cutoffs and energy minimization steps eliminated heavy dependencies on atomic coordinates.

Consistent with the observations made by previous studies, the propensity data showed the dominance of tyrosine, tryptophan, serine and phenylalanine over other residues in the paratope (Table 2). The AIF metric was then used to predict affinity enhancing mutations of antibodies across three different systems for which published data validated the predictions. One of the test case was the anti-EGFR antibody drug cetuximab (Erbitux), where a 10-fold affinity improvement to 52 µM was engineered by three mutations on the light chain. Two of these predicted mutations, S26D and T31E were shown to improve binding affinity as single mutations in cetuximab and closer inspection of the third mutation (N93A) revealed that Ala is among a set of residues with weak contact propensities overall. Another test case was the anti-lysozyme model antibody D44.1, where eighteen mutations were predicted to be suitable for affinity enhancement. Four of the predicted mutations on the heavy chain, T28D, T58D, E35S, G99D, were part of a published high-affinity variant of D44.1. Another test case was the antibody E2 that targets cancer-associated serine protease MT-SP 1. AIF metric predicted eight mutations which included T98R, confirming a previous in-silico affinity enhancement study, which had identified a single mutation T98R for improving the antibody affinity by 14-fold to 340 µM.

Example 3

Design of Affinity Enhancing Mutations in Dengue Antibody

Analysis in this Example illustrates that an anti-DV antibody that binds only certain serotypes of DV can be modified through engineering such that a variant is generated that potently neutralizes activity of all four serotypes of DV. Specifically, studies in this Example show that rationally designed mutations in a Dengue mAb 4E11 augments its affinity for DV serotype 4 (DV4), and do not significantly detrimentally affect its binding to DV serotypes 1-3 (DV1-3).

Figure 3:
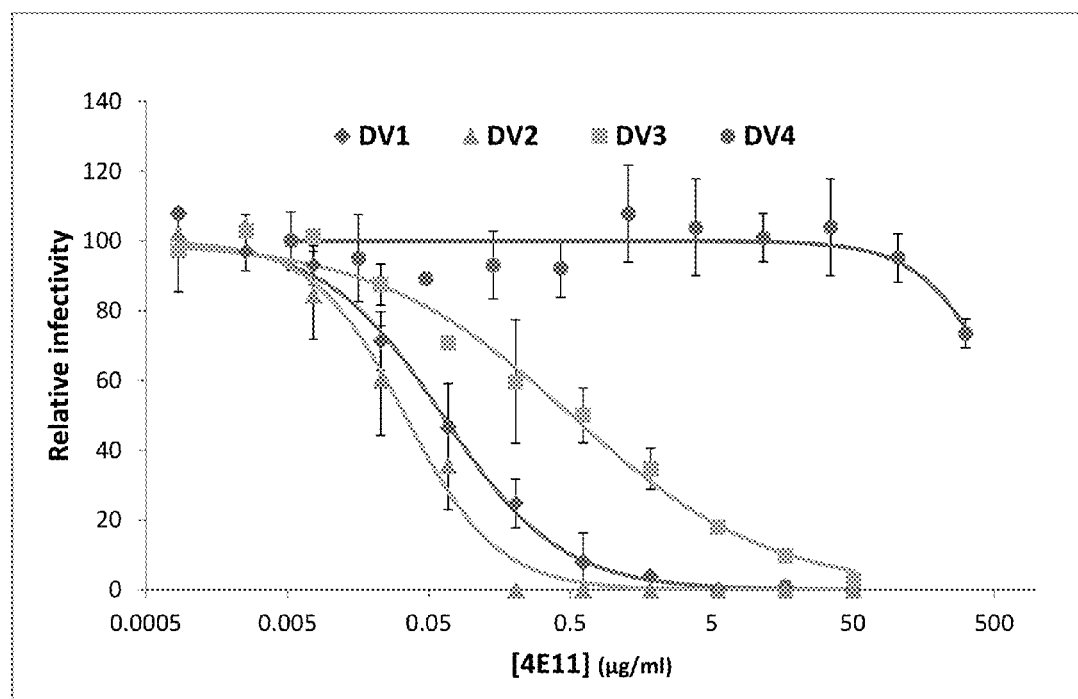
FIG. 3 demonstrates the affinity and in vitro activity of 4E11 antibody.

Binding and neutralizing activity profiles of mAb 4E11 show high affinity and inhibitory potency to DV1-3, but low affinity and neutralizing activity to DV4 (FIG. 3). To engineer 4E11 for potent neutralization activity to all four serotypes, the design approach (FIG. 4) relied on three important factors: (1) to generate an accurate model of 4E11-EDIII interaction, (2) to understand the serotype-specific structural elements and recapturing the determinants of affinity and specificity, and (3) to design of substitutions which confer favorable interaction and hence improved affinity with DV4.

Figure 5:
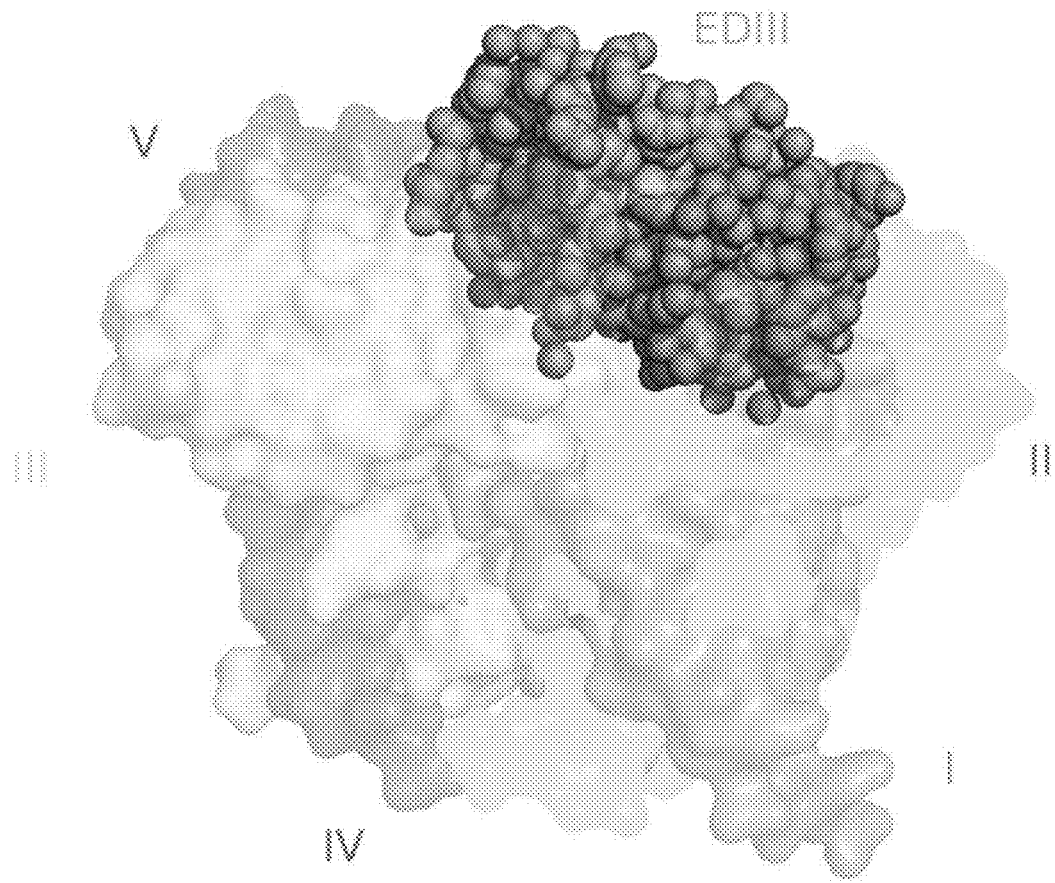
FIG. 5 demonstrates the superposition of the top five docking models on fixed EDIII. EDIII domain is represented as spheres; 4E11, displayed as the surface in each model.

In the absence of the antibody crystal structure, a structural model of the Fv region was built and the modeled Fv was docked against EDIII of DV1 using ZDOCK software, and previously published functional data on the epitope and CDR H3 paratope (Watanabe et al., 2012 Trends in Microbiology 20:11-20) were included as specific residues in the binding interface to ensure docked poses did not deviate significantly from the native complex (see Methods section). ZDOCK was run five times with different combinations of input interface residues and the best ranking model from each run (FIG. 5) was re-ranked using MLR probabilities (Table 3). The top model predicted by the MLR approach did not match with the prediction of the ZRANK method.

The top model predicted by the MLR approach was validated by comparison performed between paratope hot spots computationally predicted by the web server ANCHOR [Dosztanyi et al., 2009 Bioinformatics 25:2745-2746] and hot spots determined experimentally by Ala-scanning of each position in all CDR loops of 4E11 with binding assessment by indirect ED-III (DV1) ELISA. Hot spot prediction of the selected model correctly identified 61% of experimentally determined hot spots, whereas the remaining poses had hot spot prediction accuracies of <45% (range 28-44%), thus indicating that the selected pose was likely to reflect the true 4E11/ED-III binding configuration.

Figure 6:
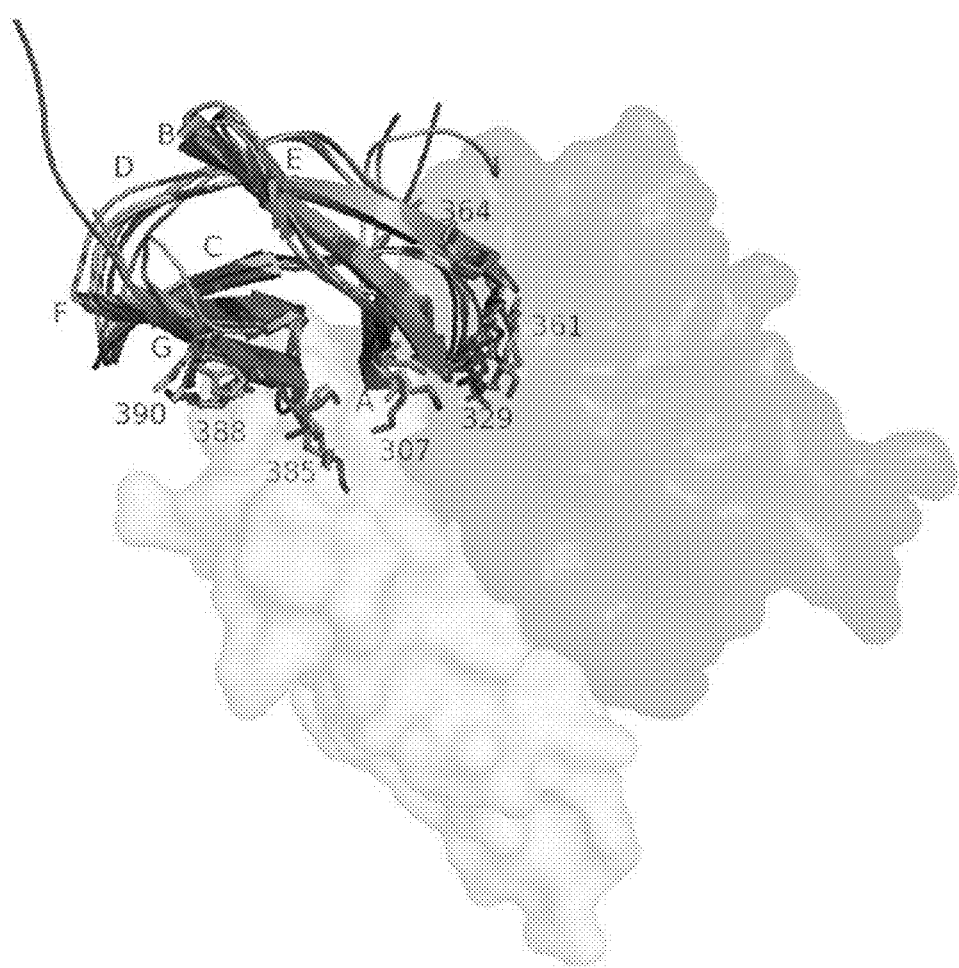
FIG. 6.

The top 4E11-ED-III (DV1) model was used to guide the modeling of the interaction between 4E11 and a representative EDIII strain from each of the other three serotypes (see Methods section). Using the four structural models, the mode of antibody binding to each of the serotypes was examined and the molecular basis of poor affinity towards DV4 serotype was identified using a combination of sequence and ED-III domain-level structural analysis. Analysis revealed multiple amino acid differences within and around the 4E11 binding interface between DV4 and other serotypes. Notably, the orientation of the A-strand (residues 305-308) relative to neighboring β-strands was different in DV4 owing to a localized difference at position 307 (FIG. 6). Consistent with the low affinity and neutralizing potency to DV4, the 4E11-EDIII (DV4) interface possessed smaller BSA, fewer H-bonds and salt bridge contacts.

AIF index was next applied to design mutations which enhance affinity to DV4 binding. This resulted in a set of 87 mutations spanning 23 CDR positions. The predicted mutations included amino acids of all types. The choice of amino acid replacements were not always intuitive (e.g., if the epitope region surrounding a paratope CDR position was negatively charged, Arg and Lys were not always statistically favored at that CDR position). While residues that improve energetics were favored, affinity gain might happen through improvements in electrostatic complementarity, packing and hydrophobic surface area. A conscious effort was taken in designing affinity-enhancing mutations at CDR positions proximal to DV4 serotype-specific residues (FIG. 6). Mutations that had potential to improve DV4 affinity while not being detrimental to other serotypes were given higher preference. In an effort to learn about the effects of point mutations on binding affinity, mutants were not restricted to residues with the highest probabilities of success.

Example 4

Experimental Characterization of Engineered Dengue Antibody

Experiments in this Example elucidate that specific engineered site-directed mutations in an antibody increase its affinity and/or potency for EDIII of DV4 without, or with only minimal reduction in binding affinity and/or potency to EDIII of DV1-3. Experiments in this Example also demonstrate that binding properties of engineered antibodies can also be accurately quantified. Experiments in this study moreover show that an engineered Dengue antibody designed by combining specific successful single-mutations results in maximum increase in the affinity of the antibody. Furthermore, experiments in this Example confirm that engineered antibodies designed in this study not only exhibit strong inhibitory activity to all four serotypes of DV, but also have potent antiviral activity in vivo.

Figure 7:
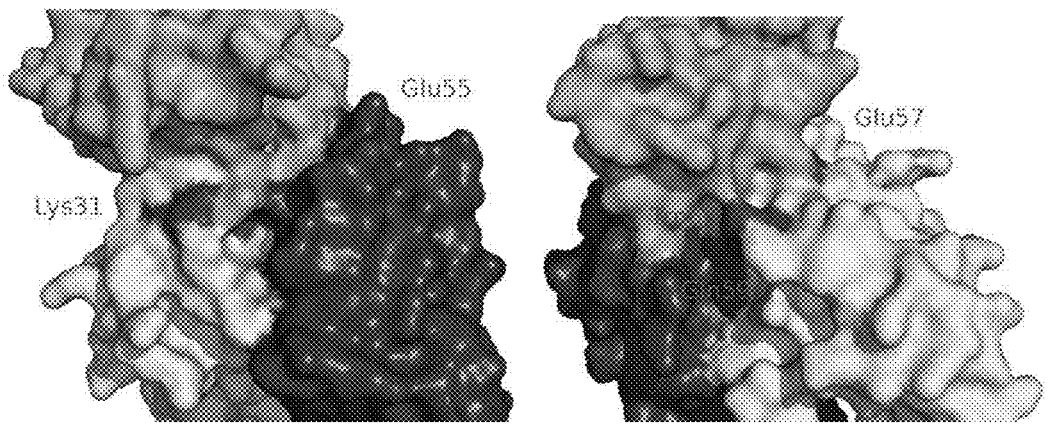

A total of 87 mutations were selected for experimental testing by indirect ELISA using purified recombinant EDIII of DV1-4 as the coated antigen. Mutants were generated by site-directed mutagenesis, sequence-confirmed, and expressed from 293 cells by transient transfection. Ten mutations were identified with enhanced EDIII-DV4 affinity with no or minimal reduction in binding to EDIII of DV1-3 (Table 3). These 10 mutations spanned five CDR positions, with four in VL (R31, N57, E59, and S60) and one in VH (A55). Eight of the 10 mutations were in VL, with 7 being in L2 alone. The successful mutations were mostly charged or polar in nature, and found to reside at the periphery of the antibody-antigen interface area (FIG. 7). Structural analysis showed the mutant side chains created contacts with highly conserved epitope residues, suggesting why they were not detrimental to DV1-3 binding (FIG. 6 and Table 5).

For further accurate quantification of binding properties of these 10 single-mutants discussed above, competition ELISA experiments were performed to determine affinities at equilibrium and in solution. Table 6 outlines affinity results from five single mutant antibodies, representing those mutations which demonstrated greatest EDIII-DV4 affinity enhancement while maintaining affinity to EDIII of DV1-3. The extent of DV4 affinity enhancement ranged from 1.1-fold (VL-R31K) to 9.2-fold (VH-A55E). Surprisingly, two mutations conferred increased affinity to other serotypes; VH-A55E resulted in a 16- and 7-fold affinity increase to ED-III-DV2 and ED-III-DV3, respectively, while VL-N57E demonstrated a 3-fold affinity increase to ED-III-DV2. Only three of the 15 affinities measured to serotypes 1-3 (with the five single mutant antibodies) showed a decrease greater than 2-fold, and only one antibody-EDIII affinity (VL-E59Q for EDIII-DV3) resulted in greater than a 3-fold decrease in affinity.

Structurally, the five affinity-enhancing positions map to spatially distinct regions of the paratope (FIG. 7) suggesting that additional enhancement could be achieved by combining successful single mutations. Multiple three-, four- and five-mutant combinations were tested, and a quintuple mutant antibody, termed 4E5A, showed the greatest increase in affinity. Surprisingly, 4E5A was composed of five substitutions representing the amino acid change at each position which conferred greatest affinity improvement to EDIII-DV4 as a single mutant. Compared to the parental mAb, 4E5A displayed 450-fold affinity improvement to EDIII-DV4 ($K_D$=91 nM) while maintaining affinity to EDIII of DV1 and DV3 and a 15-fold affinity increase to DV2 (Table 7 and Table 8). Significantly, these results illustrated that affinity of an antibody could be increased from micromolar to near-nanomolar affinity. Surface Plasmon Resonance (SPR) was used to verify affinity measurements as well as obtain kinetic binding parameters (Table 9 and FIG. 8). Affinity values from SPR were in good quantitative agreement with those obtained by competition ELISA, with the exception that specific binding of 4E11 WT to EDIII-DV4 could not be detected, indicating a very low affinity, which was in general agreement with competition ELISA results ($K_D$=41 µM).

Figure 9:
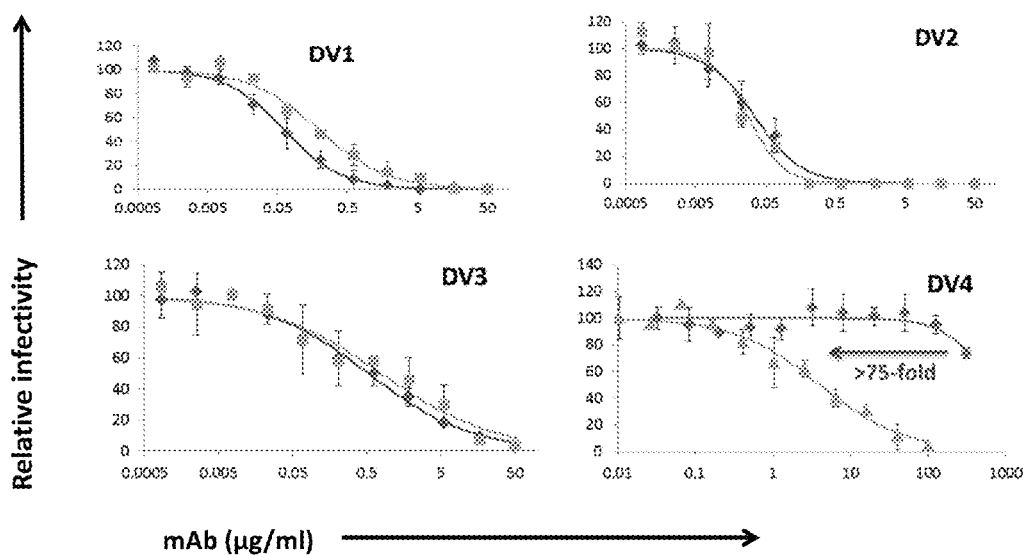
Figure 10:
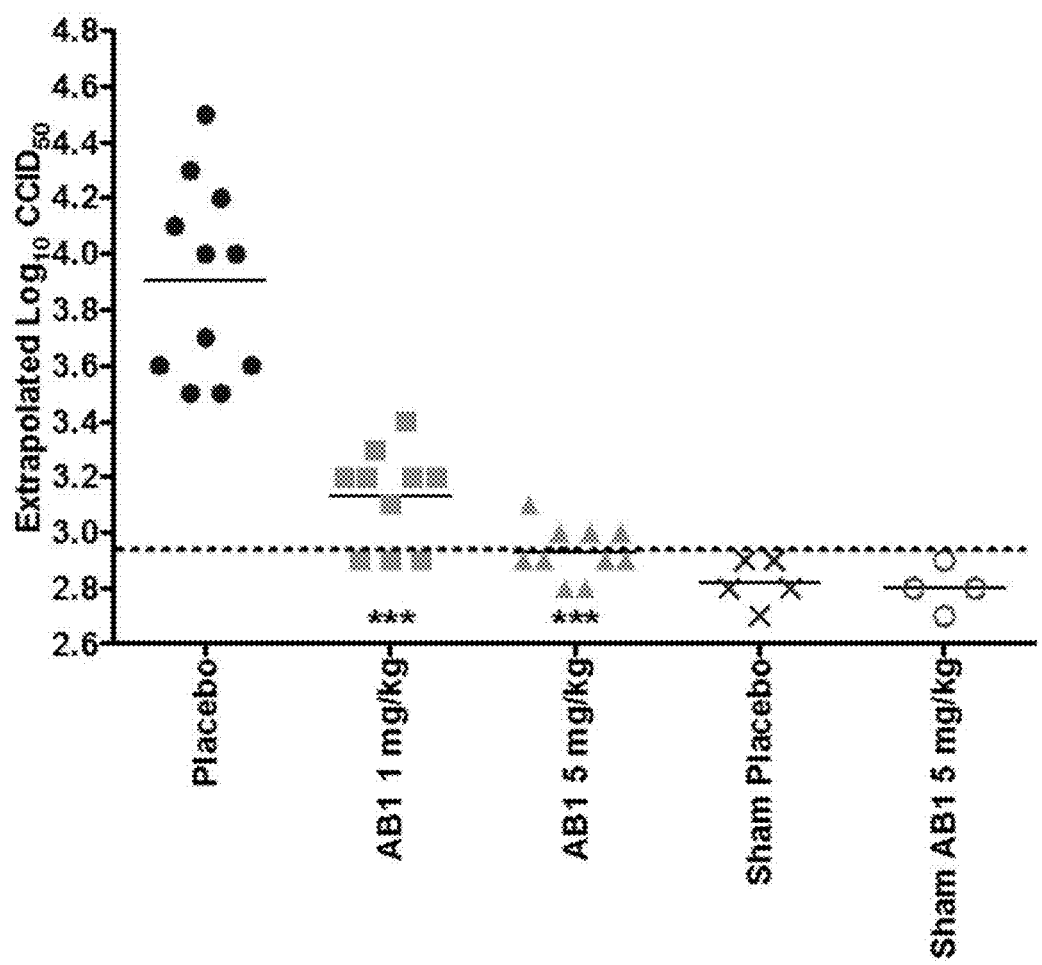

To determine whether increased affinity of 4E5A to EDIII-DV4 translated to enhanced activity, a focus reduction neutralization test (FRNT) assay was used. Compared to WT 4E11, 4E5A showed a >75 fold increase in neutralizing potency towards DV4, and it maintained potency to DV1-3 (FIG. 9). 4E5A showed strong inhibitory activity to all four serotypes, with $FRNT_{50}$ values of 0.19, 0.028, 0.77, and 4.0 µg/ml for DV1-4, respectively. To further elucidate 4E5A activity, the antibody was assessed in an AG129 mouse model of DV2 challenge, which shows peak viremia at day 3 post-infection. At both 1 mg/kg and 5 mg/kg, 4E5A demonstrated a significant reduction in viremia, with 5 mg/kg treatment resulting in virus titer levels below the limit of detection (FIG. 10). Collectively, these results showed that the engineered mAb 4E5A exhibited strong inhibitory activity to all four serotypes of DV and had potent antiviral activity in vivo.

Engineered antibodies that can be designed based on this study (e.g., 4E5A) represent important drug candidates and additionally can be taken up for further rounds of affinity maturation and humanization as is known in the art. The crystal structure of 4E11/ED-III complex was published prior to submission of the present patent application, which allowed comparison of the structural model discussed in this study with the published complex structure and indeed, excellent correspondence between the two structures with C-alpha RMSD value of 1.4 angstrom was observed, further confirming the significance of this study.

Discussion

Traditional approaches for discovering antibodies of therapeutic interest rely on experimental methods such as phage-display techniques. However, these approaches are expensive, technically challenging and time consuming. For instance, the influenza FI6 mAb, which neutralizes clade 1 & 2 viruses, was identified by screening 104,000 B cells. An alternate strategy would be to modify the properties of an existing antibody via rational engineering. In this study, computational methods for ab initio modeling and antibody re-design were presented. In test runs, the sensitivity of the MLR prediction method in picking X-ray structures (out of several decoy models) appeared superior to ZRANK. Further, it was shown that the AIF metric could capture known affinity enhancing mutations across multiple systems. This framework was then applied to engineer broader specificity and affinity to an anti-Dengue neutralizing mAb. The results obtained by this study were important as: (1) only few studies have attempted to improve the cross-reactivity of an antibody; (2) this is the first study that has employed an empirical approach towards antibody re-design and affinity enhancement; and (3) affinity enhancing mutations were predicted without the crystal structure of the antibody-antigen complex (aka blind prediction). This study showed for the first time that application of a computational approach led to a greater than ~400-fold improvement in affinity of an antibody (Table 10). Given the simplicity of these computational methods, they could be broadly employed for antibody engineering, and unlike physicsbased energetic approaches, they are not affected by the precise location of the atom coordinates of the starting structure.

The top docking solution from ZRANK was structurally very different from the native-structure, indicating that any affinity enhancement efforts following the top ZRANK model would not have led to fruitful results. Affinity enhancing mutations were also predicted using the X-ray structure by energetics approach and results highlighted the challenges in discriminating stabilizing and neutral mutations (Table 11). More significantly the affinity enhancing mutations N57E, N57S and E59N were classified as destabilizing (Table 11). Since ZRANK is widely used and has shown considerable success in the CAPRI experiments, the method presented in this study would perform comparatively well when stacked against other docking algorithms. The fact that ZEPII appeared significantly, indicated that amino acid composition and inter-residue contacts contained discriminatory power. Interestingly, some geometrical features also have the predictive power to discriminate native interfaces from decoys. This correlated with the observation made by previous studies that antigen-antibody interfaces were more planar and significantly well-ordered or packed. Between the different combinations of interface residues that were used to generate the five different models, the accurate model was produced by using all the known epitope and paratope interface residues as adding more context narrowed the search space and therefore increased the chances of finding a near-native complex structure.

Phage display and directed evolution methods randomized select CDR loops, especially VH-CDR loops since they accounted for most of the stabilizing contacts. The results on 4E11 showed that diversification strategies must use a rational approach and involve VL-loops for targeted diversification. The observation that affinity enhancing mutations were mainly polar in nature and were present at the periphery of the binding interface was consistent with known data. It is likely that these mutations increased the association rate by increasing the efficiency of collision. The success rate in predicting mutations with targeted activities is 12% (10/87).

These results were encouraging given the complexity of the design problem (i.e. involvement of multiple antigens) and considering that random mutations would have in average a detrimental effect on binding affinity.

Studies have shown that murine germline harbors gene segments with an inherent capacity for high-affinity binding to EDIII domain (Ref 24, 32). Despite the beneficial effect of the 5 mutations, these mutations have not co-evolved in vivo. Codon-level analysis showed that amino acid replacements at N57E and S60W required at least two base changes highlighting the limitations at the genomic level. Previous studies have shown that the epitopes recognized by anti-DV antibodies fall into three different regions: (1) lateral-ridge epitope on ED-III (serotype-specific potent neutralizers); (2) A-strand of DIII (subcomplex-specific neutralizers); and (3) other DII and DIII epitopes (complex-specific or flavivirus cross-reactive moderately potent neutralizers). In this study, it was shown for the first time that antibody against A-strand epitope could be engineered to bind all four serotypes with good in vitro potency. Collectively, 4E5A exhibited an interesting broad spectrum neutralization profile and would be an antibody of interest for potential therapeutic development for treatment of Dengue disease. mAb therapeutics against DV in humans could face regulatory hurdles due to antibody-dependent enhancement. However, recent studies have shown that modifications to the Fc region of recombinant anti-DV antibodies prevent ADE in vivo, thus presenting opportunities for these newer complementary approaches. The degree of conservation of mAb epitope can be a significant factor in determining neutralizing spectrum and in vivo protection. Phylogenetic analysis of DV4 viruses has revealed the existence of four distinct genotypes: I (Southeast Asia), II (Indonesia), III and IV (Sylvatic or Malaysia). Within genotype II, viruses cluster into two distinct clades previously defined as IIa and IIb. Sequence analysis of 4E11-5A's epitope region revealed high degree of conservation in genotypes IIa, IIb and 4, while relatively lower conservation in genotype I, suggesting to the present inventors that the engineered antibody would likely be effective against the majority of DV4 viruses.

TABLE 1

Description of physicochemical features.

| Feature No. | Description of feature | Feature sub-classification |
|---|---|---|
| Chemical | | |
| 1 | Number of various types of interactions | (1) hydrophobic, (2) disulphide bridges, (3) hydrogen bond, (4) ionic interactions, (5) aromatic-aromatic, (6) aromatic-sulphur, (7) cation-pi |
| 2 | density of each type of interactions (i.e. how many contacts of each type is observed on average per 100 square angstroms of the interface) | (1) hydrophobic, (2) disulphide bridges, (3) hydrogen bond, (4) ionic interactions, (5) aromatic-aromatic, (6) aromatic-sulphur, (7) cation-pi |
| 3 | classification of hydrogen-bonds | (1) main chain - main chain, (2) main chain - side chain, (3) side chain-side chain) |
| 4 | number of salt bridge interactions | |
| 5 | number of hydrogen bonds that involve charged residues | |
| 6 | composition of chemical groups | (1) polar, (2) neutral and (3) non-polar chemical groups |
| 7 | ZEPII | Assesses the frequencies of favorable interactions to indicate the probability of antibody binding to a given surface (see Methods section) |
| Physical | | |
| 7 | buried surface area | |
| 8 | planarity | |
| 9 | surface complementarity | |
| 10 | interface atom packing density | |

TABLE 1-continued

Description of physicochemical features.

| Feature No. | Description of feature | Feature sub-classification |
|---|---|---|
| 11 | distance between the binding site of the antigen from its center of mass | |
| 12 | novel metric that quantifies the antibody binding potential of a surface by enumerating the number of favorable interactions that are common to antigen-antibody interfaces | |

TABLE 2

The 20 × 20 amino acid propensity matrix. Paratope amino acids are indicated on the left side and epitope amino acids are indicated on the upper side. The propensity data was generated using 77 non-redundant antigen-antibody complexes.

| | ALA | ARG | ASN | ASP | CYS | GLU | GLN | GLY | HIS | ILE | LEU | LYS | MET | PHE | PRO | SER | THR | TRP | TYR | VAL |
|---|---|---|---|---|---|---|---|---|---|---|---|---|---|---|---|---|---|---|---|---|
| ALA | 0.25 | 0.59 | 0.14 | 0.53 | 0 | 0.28 | 0.6 | 0.35 | 1.33 | 0.68 | 1.1 | 0.33 | 2.3 | 2.94 | 0.77 | 0.25 | 0.38 | 1.49 | 0.59 | 1 |
| ARG | 0.58 | 0.87 | 1.11 | 2.29 | 0 | 1.75 | 0.87 | 0.67 | 0.95 | 1.03 | 0.99 | 0.44 | 0.79 | 0.75 | 0.15 | 0.5 | 0.66 | 0.29 | 2.24 | 0.57 |
| ASN | 0.74 | 1.32 | 1.04 | 0.94 | 0.72 | 1.28 | 1.32 | 1.08 | 1.94 | 1.03 | 0.33 | 1.05 | 1.53 | 0.54 | 0.74 | 0.78 | 0.58 | 0.83 | 0.82 | 0.41 |
| ASP | 0.23 | 1.68 | 0.81 | 0.6 | 0 | 0.75 | 0.54 | 0.79 | 1.04 | 0.4 | 1.27 | 2.2 | 0.62 | 0.58 | 0.51 | 0.84 | 1.08 | 0.89 | 1.05 | 0.27 |
| CYS | 5.29 | 0 | 0 | 5.59 | 36.02 | 0 | 0 | 2.46 | 0 | 0 | 0 | 0 | 0 | 6.85 | 2.68 | 0 | 0 | 0 | 0 | 4.17 |
| GLU | 0.22 | 1.41 | 0.6 | 0.23 | 0 | 0.36 | 0.39 | 0.2 | 0.57 | 0.39 | 0.14 | 0.85 | 0.39 | 0.56 | 0.44 | 0.75 | 0.55 | 0.85 | 0.17 | 0.34 |
| GLN | 0.44 | 0.2 | 0.72 | 0.23 | 0 | 0.48 | 0.26 | 0.61 | 0 | 0.78 | 0.82 | 0.38 | 0 | 0.57 | 0.44 | 0.65 | 0.44 | 0 | 1.02 | 0 |
| GLY | 0.31 | 1.01 | 0.57 | 0.49 | 1.06 | 1.37 | 0.99 | 0.72 | 0.68 | 0.56 | 0.39 | 0.9 | 0.76 | 0.94 | 0.89 | 0.51 | 0.84 | 0.61 | 0.97 | 0.74 |
| HIS | 0.55 | 0.64 | 0.76 | 0.87 | 0 | 0.91 | 1.15 | 0.51 | 0.73 | 0.49 | 0.52 | 0.6 | 1 | 0 | 0.84 | 0.27 | 0.56 | 0 | 0.43 | 0.65 |
| ILE | 0.31 | 0.57 | 0.17 | 0.32 | 0 | 0.34 | 0.73 | 0.14 | 1.2 | 0.55 | 1.33 | 0.66 | 2.22 | 1.58 | 0.31 | 0.45 | 0.92 | 3 | 2.36 | 1.2 |
| LEU | 0.42 | 0.88 | 0.7 | 0.22 | 0.72 | 0.7 | 0.63 | 0.59 | 1.12 | 1.51 | 1.98 | 0.83 | 1.16 | 1.37 | 0.86 | 0.52 | 0.43 | 2.09 | 1.64 | 1 |
| LYS | 0 | 0.31 | 0.37 | 0.71 | 0 | 1.86 | 0.4 | 0.16 | 0.89 | 0 | 0.42 | 0.59 | 0 | 1.31 | 0.17 | 0.67 | 0.17 | 1.33 | 0 | 0.27 |
| MET | 0 | 0.99 | 1.17 | 0 | 0 | 1.17 | 0.64 | 0.5 | 1.4 | 0.95 | 0 | 0 | 3.88 | 0 | 0.54 | 0 | 0 | 2.1 | 1.65 | 0.84 |
| PHE | 1.81 | 1.36 | 0.74 | 0.72 | 0.77 | 0.87 | 1.22 | 1.16 | 2.98 | 0.81 | 1.41 | 1.17 | 0.82 | 2.05 | 1.49 | 0.67 | 1.03 | 1.78 | 0.35 | 1.6 |
| PRO | 0.75 | 1.04 | 0.41 | 0.2 | 0 | 0.41 | 1.12 | 0.17 | 1.97 | 1 | 1.4 | 0.49 | 2.72 | 1.94 | 0.38 | 0.55 | 0.57 | 0.74 | 1.16 | 0 |
| SER | 1.12 | 1.27 | 0.62 | 0.93 | 1.37 | 1.64 | 1.54 | 0.6 | 1.16 | 0.43 | 1.25 | 0.97 | 1.02 | 1.04 | 0.73 | 0.83 | 0.93 | 1.42 | 1.43 | 0.82 |
| THR | 0.84 | 1.17 | 0.79 | 1.14 | 0 | 1.06 | 1.15 | 0.34 | 1.42 | 0.54 | 0.37 | 0.83 | 1.31 | 0.16 | 0.79 | 0.77 | 1.03 | 0.24 | 0.56 | 0.76 |
| TRP | 1.27 | 1.71 | 1.16 | 1.05 | 3.37 | 0.47 | 2.03 | 0.99 | 2.61 | 0.51 | 1.06 | 1.78 | 1.03 | 0.73 | 1 | 1.12 | 0.86 | 0.56 | 1.86 | 1.56 |
| TYR | 1.48 | 2.21 | 1.83 | 1.56 | 2.04 | 1.96 | 1.6 | 1.73 | 2.01 | 1.9 | 2.38 | 1.78 | 1.89 | 2.69 | 1.88 | 1.35 | 1.21 | 1.4 | 1.36 | 1.46 |
| VAL | 0.3 | 1.1 | 0.49 | 0.78 | 1.01 | 1.3 | 0.88 | 0.28 | 1.56 | 0.79 | 1.11 | 0.26 | 0.54 | 1.15 | 0.3 | 0.59 | 0.45 | 2.92 | 0.69 | 0.47 |

TABLE 3

Physicochemical properties of the top five docked structural models. Columns 2-9 provide values of pre-computed significant features for the docked models. The p-value and odds ratio (OR) are listed in the column headers. The MLR regression coefficient of the features is listed in the last row of the table. Columns 10 and 11 provide MLR-based prediction probability and ZRANK score, respectively.

| Pose | ZEPII (OR = 4.948081868; p-value = 2E−16) | BSA (OR = 0.595234401; p-value = 0.000994) | Ionic contact density (OR = 0.769203281; p-value = 0.048709) | Cation-pi density (OR = 1.453682511; p-value 0.000831) | Hydrogen bond density (OR = 0.409261894; p-value 0.000000432) |
|---|---|---|---|---|---|
| 1 | 1.1032203 | 2269 | 0.485 | 0.176 | 0.661 |
| 2 | 1.0727273 | 1941 | 0.567 | 0.155 | 0.824 |
| 3 | 1.1028767 | 2340 | 0.513 | 0.128 | 1.026 |
| 4 | 1.0836066 | 2436 | 0.369 | 0.164 | 0.698 |
| 5 | 0.9682895 | 2481 | 0.363 | 0.202 | 0.846 |
| Regression coefficient | 1.599 | −0.5188 | −0.2624 | 0.3741 | −0.8934 |

| Pose | Main chain-main chain contacts (OR = 0.072352881; p-value 3.06E−11) | Percentage of charged groups (OR = 4.853984917; p-value 0.000000516) | Percentage of neutral polar groups (OR = 1.412696091; p-value 0.03383) | MLR prediction probability | ZRANK score |
|---|---|---|---|---|---|
| 1 | 15 | 10 | 0.1071 | 0.00263 | −75.833 |
| 2 | 16 | 15 | 0.0982 | 0.00159 | −85.636 |

TABLE 3-continued

Physicochemical properties of the top five docked structural models. Columns 2-9 provide values of pre-computed significant features for the docked models. The p-value and odds ratio (OR) are listed in the column headers. The MLR regression coefficient of the features is listed in the last row of the table. Columns 10 and 11 provide MLR-based prediction probability and ZRANK score, respectively.

| | | | | | |
|---|---|---|---|---|---|
| 3 | 24 | 19 | 0.1389 | 0.00003 | −66.75 |
| 4 | 17 | 14 | 0.1186 | 0.00192 | −71.73 |
| 5 | 21 | 16 | 0.1587 | 0.00001 | −72.775 |
| Regression coefficient | −2.6262 | 1.5798 | 0.3455 | | |

TABLE 4

Mutations that led to increase in EDIII-DV4 affinity while maintaining original EDIII-DV1-3 affinity.

| Chain | CDR | Position | WT residue | Mutation |
|---|---|---|---|---|
| VH | H2 | 55 | Ala | Glu |
| VH | H2 | 55 | Ala | Asp |
| VL | L1 | 31 | Arg | Lys |
| VL | L2 | 57 | Asn | Glu |
| VL | L2 | 57 | Asn | Ser |
| VL | L2 | 59 | Glu | Gln |
| VL | L2 | 59 | Glu | Asn |
| VL | L2 | 60 | Ser | Trp |
| VL | L2 | 60 | Ser | Tyr |
| VL | L2 | 60 | Ser | Arg |

TABLE 5

Contacts made by affinity enhancing mutations.

| Chain & CDR | Position | WT residue | Mutation | Predicted DV4 contacts |
|---|---|---|---|---|
| VH-H2 | 55 | Ala | Glu | H-bond, Ionic contact with Lys (310), Lys (323) |
| | | | Asp | H-bond, Ionic contact with Lys (310), Lys (323) |
| VL-L1 | 31 | Arg | Lys | Ionic contact with Glu (311) |
| VL-L2 | 57 | Asn | Glu | Ionic contact with Lys (305) |
| | | | Ser | H-bond with Lys (310) |
| VL-L2 | 59 | Glu | Gln | H-bond with Glu (327) |
| | | | Asn | H-bond with Glu (327) |
| VL-L2 | 60 | Ser | Trp | Hydrophobic contact with Ala (329) |
| | | | Tyr | H-bond with Glu (327) |
| | | | Arg | Ionic, H-bond with Glu (327) and H-bond with Gly (328) |

TABLE 6

Affinities of single mutant antibodies with increased EDIII-DV4 affinity and similar EDIII-DV1-3 affinities relative to 4E11 WT.

| Mutation | CDR | EDIII-DV1 $K_D$ (nM) | EDIII-DV2 $K_D$ (nM) | EDIII-DV3 $K_D$ (nM) | EDIII-DV4 $K_D$ (nM) |
|---|---|---|---|---|---|
| 4E11 WT | - | 0.328 | 5.20 | 21.8 | 40,793 |
| A55E | H2 | 0.295 | 0.323 | 2.95 | 4442 |
| R31K | L1 | 0.378 | 5.35 | 21.1 | 37,292 |
| N57E | L2 | 0.281 | 1.75 | 33.9 | 8408 |
| E59Q | L2 | 0.772 | 10.8 | 102 | 11,034 |
| S60W | L2 | 0.284 | 6.30 | 23.1 | 26,351 |

Affinity relative to WT 0.1  1  10+

Mutations included are those which, for each identified position, demonstrated greatest EDIII-DV4 affinity while approximately maintaining EDIII-DV1-3 affinity. $K_D$ values represent the average of at least two independent experiments.

TABLE 7

Affinity of combination mutant 4E11-5A.

| Method | mAb | EDIII-DV1 $K_D$ (nM) | EDIII-DV1 Fold-change | EDIII-DV2 $K_D$ (nM) | EDIII-DV2 Fold-change | EDIII-DV3 $K_D$ (nM) | EDIII-DV3 Fold-change | EDIII-DV4 $K_D$ (nM) | EDIII-DV4 Fold-change |
|---|---|---|---|---|---|---|---|---|---|
| Competition ELISA | 4E11 WT | 0.328 | — | 5.20 | — | 21.8 | — | 40,793 | — |
| | 4E11-5A | 0.309 | 1.1 | 0.246 | 21.1 | 16.5 | 1.3 | 91.2 | 447.3 |
| SPR | 4E11 WT | 0.50 | — | 6.20 | — | 7.58 | — | NB | — |
| | 4E11-5A | 1.78 | 0.28 | 0.70 | 8.9 | 5.19 | 1.5 | 114 | — |

TABLE 8

Energetic calculations of 4E5A showing mutations have additive effect on binding energy.

| Antibody | EDIII-DV4 ΔG (kcal/mol)[a] | EDIII-DV4 ΔΔG (kcal/mol)[b] |
|---|---|---|
| 4E11 WT | −5.98 | — |
| VH-A55E | −7.29 | −1.31 |
| VL-R31K | −6.03 | −0.05 |
| VL-N57E | −6.92 | −0.93 |
| VL-E59Q | −6.76 | −0.77 |
| VL-S60W | −6.24 | −0.26 |
| 4E5A | −9.59 | −3.61 |

[a] Free energy calculated by ΔG = RTln($K_D$) at 25° C.
[b] ΔΔG = ΔG$_{mut

TABLE 11

Antibody mutations predicted using energetics approach.

| Mutation at ALA55 | Mutation Energy | Effect of Mutation |
|---|---|---|
| VH:ALA55 | | |
| GLU | −1 | stabilizing |
| THR | −0.44 | neutral |
| TRP | −0.4 | neutral |
| ASP | −0.37 | neutral |
| GLN | −0.33 | neutral |
| LEU | −0.33 | neutral |
| TYR | −0.29 | neutral |
| ARG | −0.23 | neutral |
| PRO | −0.23 | neutral |
| ILE | −0.17 | neutral |
| MET | −0.17 | neutral |
| VAL | −0.14 | neutral |
| PHE | −0.09 | neutral |
| CYS | −0.04 | neutral |
| ALA | 0 | neutral |
| HIS | 0.06 | neutral |
| GLY | 0.07 | neutral |
| ASN | 0.13 | neutral |
| SER | 0.17 | neutral |
| LYS | 1.06 | destabilizing |

TABLE 11-continued

Antibody mutations predicted using energetics approach.

| Mutation at ARG31 | Mutation Energy | Effect of Mutation |
|---|---|---|
| VL:ARG31 | | |
| LYS | −1.01 | stabilizing |
| HIS | −0.13 | neutral |
| MET | −0.04 | neutral |
| PRO | −0.04 | neutral |
| ARG | 0 | neutral |
| ILE | 0.16 | neutral |
| THR | 0.22 | neutral |
| VAL | 0.22 | neutral |
| ASN | 0.24 | neutral |
| ALA | 0.3 | neutral |
| CYS | 0.32 | neutral |
| SER | 0.34 | neutral |
| GLY | 0.41 | neutral |
| TYR | 0.46 | neutral |
| PHE | 0.47 | neutral |
| GLN | 0.48 | neutral |
| LEU | 0.48 | neutral |
| TRP | 0.68 | destabilizing |
| ASP | 1.14 | destabilizing |
| GLU | 1.26 | destabilizing |

TABLE 11-continued

Antibody mutations predicted using energetics approach.

| Mutation at ASN57 | Mutation Energy | Effect of Mutation |
|---|---|---|
| VL:ASN57 | | |
| LEU | -1.79 | stabilizing |
| PHE | -1.69 | stabilizing |
| TYR | -1.44 | stabilizing |
| ARG | -0.88 | stabilizing |
| TRP | -0.64 | stabilizing |
| GLN | -0.62 | stabilizing |
| MET | -0.57 | stabilizing |
| HIS | -0.51 | stabilizing |
| LYS | -0.04 | neutral |
| ASN | 0 | neutral |
| ILE | 0.53 | destabilizing |
| ASP | 0.58 | destabilizing |
| PRO | 0.68 | destabilizing |
| THR | 0.93 | destabilizing |
| CYS | 1.14 | destabilizing |
| GLU | 1.17 | destabilizing |
| ALA | 1.32 | destabilizing |
| SER | 1.53 | destabilizing |
| VAL | 1.88 | destabilizing |
| GLY | 1.95 | destabilizing |

TABLE 11-continued

Antibody mutations predicted using energetics approach.

| Mutation at GLU59 | Mutation Energy | Effect of Mutation |
|---|---|---|
| VL:GLU59 | | |
| PHE | -1.02 | stabilizing |
| TYR | -1 | stabilizing |
| GLN | -0.86 | stabilizing |
| ARG | -0.5 | neutral |
| LYS | -0.35 | neutral |
| ASP | -0.29 | neutral |
| MET | -0.24 | neutral |
| HIS | -0.23 | neutral |
| LEU | -0.1 | neutral |
| ILE | -0.01 | neutral |
| GLU | 0 | neutral |
| PRO | 0.05 | neutral |
| VAL | 0.06 | neutral |
| THR | 0.17 | neutral |
| SER | 0.34 | neutral |
| CYS | 0.39 | neutral |
| ALA | 0.51 | destabilizing |
| GLY | 0.52 | destabilizing |
| ASN | 0.68 | destabilizing |
| TRP | 2.53 | destabilizing |

TABLE 11-continued

Antibody mutations predicted using energetics approach.

| Mutation at SER60 | Mutation Energy | Effect of Mutation |
|---|---|---|
| VL:SER60 | | |
| SER | -2.21 | stabilizing |
| PHE | -2.17 | stabilizing |
| ARG | -1.69 | stabilizing |
| LYS | -1.69 | stabilizing |
| GLN | -1.65 | stabilizing |
| LEU | -1.44 | stabilizing |
| TRP | -1.31 | stabilizing |
| MET | -1.26 | stabilizing |
| HIS | -0.8 | stabilizing |
| ASN | -0.79 | stabilizing |
| CYS | -0.64 | stabilizing |
| THR | -0.57 | stabilizing |
| ALA | -0.56 | stabilizing |
| ASP | -0.45 | neutral |
| GLU | -0.42 | neutral |
| GLY | -0.05 | neutral |
| TYR | 0 | neutral |
| ILE | 0.43 | neutral |
| VAL | 0.61 | destabilizing |
| PRO | 3.31 | destabilizing |

Mutations that are the affinity of 4E11 are shaded.

Methods

A Mathematical Model for Estimating Contact Propensities of Amino Acids in the Antigen-Antibody Interface Briefly, in an antigen-antibody interface, a pair of residues presumably interact if they had favorable energetics of interaction or by chance occurrence. The propensity of amino acid interaction was calculated by computing the number of interactions expected by chance i.e. the expected frequency, and dividing the observed frequency by this number.

If two amino acids, one from each side of the antigen-antibody interface, were within 4.5 Å (i.e. shortest non-H atom distance is less than 4.5 Å) from each other, they were defined as pair residues. If the total number of pairwise interactions between residues x (antigen) and y (antibody) at the interface was N (x, y), then their concurrence frequency, F (x, y), was defined as follows:

$$F(x, y) = \frac{N(x, y)}{\sum_{l=1}^{20} \sum_{m=1}^{20} N(l, m)}$$

The denominator of the above equation indicates the summation of pairwise interactions of all residue pairs in the interface.

The frequency of occurrence of every amino acid at paratope and epitope must be calculated. The frequency of a particular amino acid x in the epitope, $F^{epitope}(x)$, was defined as follows:

$$F^{epitope}(x) = \frac{N(x)}{\sum_{l=1}^{20} N(l)}$$

In the above equation N(x) denotes the count of amino acid x in the epitope. The denominator represents the total number of all amino acids in the epitopes.

Similarly, the frequency of occurrence of amino acid y in the paratope, $F^{paratope}(y)$ was defined as follows:

$$F^{paratope}(y) = \frac{N(y)}{\sum_{l=1}^{20} N(l)}$$

In the above equation, N(y) denotes the number of amino acid y in the paratope. The denominator indicates the total number of all amino acids in the paratopes.

Figure 11:
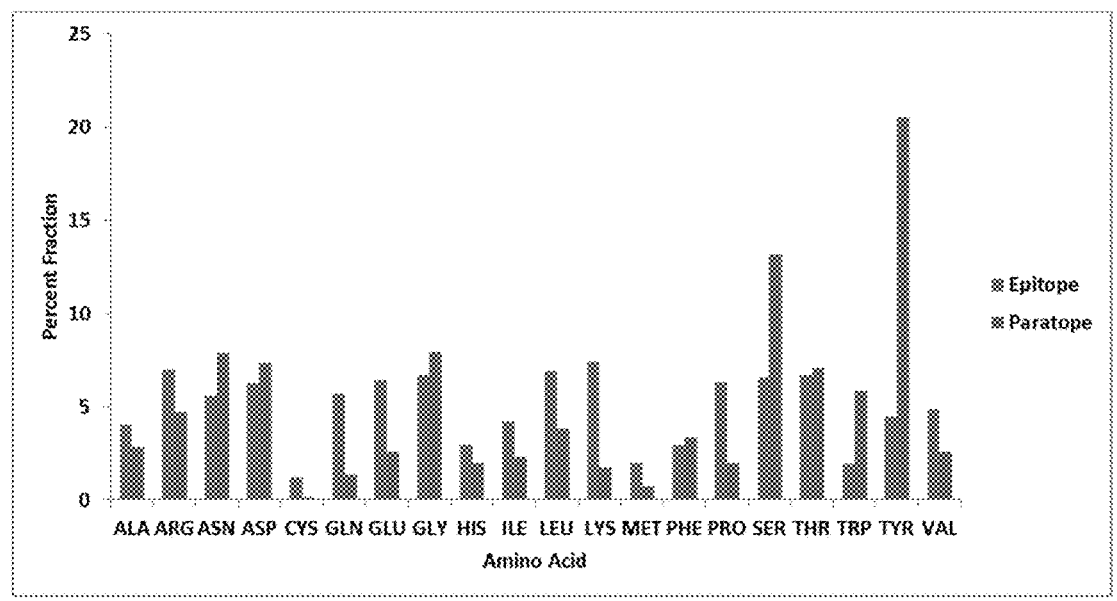

Parameters F (x, y), $F^{epitope}(x)$ and $F^{paratope}(y)$ were determined using all the seventy-seven benchmarked antigen-antibody structures in the data set. Consistent with observations made by previous studies, tyrosine, serine, glycine and asparagine were the most abundant paratope residues whereas lysine, arginine, leucine and glycine were the most abundant epitope residues (FIG. 11). If the occurrences of amino acids x and y were independent, $EF^{epitope-paratope}(x, y)$ defined in the below equation was an expected frequency rate that amino acids x and y appear concurrently.

$$EF(x,y) = F^{epitope}(x) F^{paratope}(y)$$

If the concurrence rate of the amino acids x and y at the interface for the antigen was more than the expected rate, the following ratio $RA_a$ (x, y) becomes greater than 1.

$$RA(x, y) = \frac{F(x, y)}{EF(x, y)}$$

$RA_s(x, y)$ was a 20×20 matrix. Exemplary applications of $RA_s$ (x, y) are suggested below.

Using RA (x, y) to determine the AIF of a CDR residue. The AIF of a CDR residue in the interface was defined as the sum of the RA (x, y) with its neighbors. Neighbors were defined by a distance criterion (4.5 Å).

Determine the optimal choice of amino acid at an interface position (paratope re-engineering). Given an antigen-antibody complex, amino acid preferences at a CDR position were computed using the contact potential score. Specifically, at a given CDR position, the wild type (WT) residue was systematically substituted by the remaining amino acids excluding glycine and proline (to avoid backbone conformation alterations) and the probability of replacement was evaluated at each instance using the AIF metric. Single mutations with replacement potential higher than wild type residue were reevaluated computationally to find mutations that—(a) do not bury polar groups, and (b) do not cause steric hindrance.

Using RA (x, y) to quantify the strength of interaction of antigen-antibody interface (the Epitope-Paratope Interface Index). The interaction between an antigen and antibody results from the formation of numerous non-covalent bonds. Therefore, the interaction affinity was directly related to summation of the attractive and repulsive forces (van der Waals interactions, hydrogen bonds, salt bridges and hydrophobic force). Herein, the strength of interaction of an antibody-antigen interface was investigated quantitatively by a linear combination of RAs for all combinations of amino acid pairs. An index expressing the strength of an antigen-antibody interface 'i' (called Epitope-Paratope Interface Index (EPII)) was defined by:

$$EPII_i = \frac{\sum_{x=1}^{20} \sum_{y=1}^{20} F^i(x, y)RA(x, y)}{\sum_{x=1}^{20} \sum_{y=1}^{20} F^i(x, y)}$$

In the equation above $F^i$ (x, y) denotes the concurrence frequency of amino acids x (x belongs to secondary structural groups) and y at interface i.

Using EPII to discriminate a true antigen-antibody interaction from docking decoys. In order to distinguish an interface with the most potential from other decoy interfaces generated by computational docking, the EPII values should be normalized by all the interfaces in the protein. Z-scored EPII were used for this purpose. If M interfaces were found in a protein, the Z-scored EPII for interface i was calculated as follows:

$$Z_{EPII_i} = \frac{EPII_i - \mu}{\sigma}, \text{ where}$$

$$\mu = \frac{\sum_{i=1}^{M} EPII_i}{M}$$

$$\sigma = \sqrt{\frac{\sum_{i=1}^{M} (EPII_i - \mu)*(EPII_i - \mu)}{M}}$$

The $Z_{EPII_i}$ score was an indicator of the probability of antibody binding to a given interface. Interface with the highest $Z_{EPII_i}$ score (or with $Z_{EPII_i}$ above the consensus value established for antigen-antibody interaction (discussed above)) in a protein was the most probable site for antibody binding.

Data Set of Non-Redundant Antigen-Antibody Structural Complexes and Computational Docking to Generate Decoy Models A total of 568 antigen-antibody complexes from the Protein Data Bank were analyzed. In order to ensure proper enumeration of geometric interface features (planarity, buried surface area etc.), structures wherein the antigen length was less than 20 amino acids were excluded. Additionally, many structures contained same or similar antigen, which could bias the studies, giving higher weight for factors derived from multiply-represented protein antigen. To remove redundant structures from the data set, structures that have homologous antigen (defined by BLAST_EN-REF_40 P-value 10e27) and share 50% epitope residues were classified under the same group and the structure with the highest resolution was selected as the representative. This led to seventy-seven non-redundant antigen-antibody complex structures.

ZDOCK was used to generate decoy computational models of antigen-antibody interaction. The protocol for generating the decoys models were the same for all the seventy seven structural complexes. Only the variable domain of the antibody was used for docking. The larger of the two molecules was considered the receptor while the smaller molecule was considered the ligand. The ligand orientation was rotated 6 degrees at each step to sample the various conformations. Since, the initial docking procedure explores a relative large area, distance constraints between putative hotspot residues on epitope and paratope were set up to ensure the generated models did not shift significantly from the native pose. Two hotspot residues were selected on either side to ensure the challenges faced with structure prediction was equivalent to the 4E11 scenario. In all the decoys models, the putative epitope and paratope hotspots were within 10 angstroms from each other. Hotspots were identified using the web server, ANCHOR. The initial docking procedure generated 2,000 poses which were then clustered based on an all-versus-all RMSD matrix, described previously. The RMSD between two docked poses was calculated based on the ligand residues within 7 angstroms of the binding interface. Docked protein poses representing the cluster centers were considered as decoy models. ZDOCK uses shape complementarity along with desolvation and electrostatic energy terms ('ZRANK') to rank the docked poses. Each of these decoys was further refined using CHARMm minimization.

The X-ray structures were combined with the decoy models for evaluating the sensitivity of the prediction methods.

Homology Modeling of 4E11 Fv

Structural model of 4E11 Fv was built using SIWW-MODEL homology modeling server. Studies indicated that the overall accuracy of modeling the hypervariable CDR was appropriate when (1) the degree of sequence similarity between the target and the template was high, (2) main-chain conformations of the CDR loops L1, L2, L3, H1, H2 follow the "canonical structure" and (3) heavy chain CDR3 (H3) was not unusually long.

Computational Docking for Generating 4E11-EDIII (DV1-4) Poses

The modeled Fv was docked against EDIII of a select DV1 strain using ZDOCK. DV1 antigen was used because mAb 4E11 was originally isolated from a mouse infected with a DV1 virus. The structure of the DV1 antigen was modeled using SWISS MODEL homology modeling server keeping the solved crystal structure of DV1 EDIII (PDB: 3IRC) as the template. ZDOCK uses shape complementarity along with desolvation and electrostatic energy terms ('ZRANK') to rank the docked poses. In order to ensure the docked poses do not deviate significantly from the native complex, mapped epitope and paratope residues found in the literature were forced to be included in the binding interface. Residues included in the interface were 307K, 389L and 391W (epitope; DV1 numbering as in 3IRC) and 101W, 102E (paratope; numbering based on sequence position).

The structures of 4E11 in complex with DV2, 3, 4 (EDIII) were modeled using 4E11-DV1 EDIII structural model as the template.

EQUIVALENTS AND SCOPE

Those skilled in the art will recognize, or be able to ascertain using no more than routine experimentation, many equivalents to the specific embodiments of the invention, described herein. The scope of the present invention is not intended to be limited to the above Description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein. It is noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein.

The publications discussed above and throughout the text are provided solely for their disclosure prior to the filing date of the present application. Nothing herein is to be construed as an admission that the inventors are not entitled to antedate such disclosure by virtue of prior disclosure.

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

What is claimed is:

1. An antibody agent specific to Dengue virus, which antibody agent comprises a heavy chain variable region and a light chain variable region, each of which includes complementarity determining regions (CDRs), wherein
the heavy chain variable region comprises CDRs whose amino acid sequences are set forth in SEQ ID NO: 23, SEQ ID NO: 24, and SEQ ID NO: 25; and
the light chain variable region comprises CDRs whose amino acid sequences are set forth in SEQ ID NO: 26, SEQ ID NO: 27, and SEQ ID NO: 28.

2. The antibody agent according to claim 1, which is an IgG.

3. The antibody agent according to claim 1, which is a monoclonal antibody.

4. The antibody agent according to claim 1, wherein the antibody agent is selected from the group consisting of: a mouse antibody, a humanized antibody, a human antibody, a purified antibody, an isolated antibody, a chimeric antibody, a polyclonal antibody, and combinations thereof.

5. The antibody agent according to claim 1, wherein the antibody agent is selected from the group consisting of: a Fab fragment, a Fab' fragment, a F(ab')$_2$ fragment, a Fd fragment, a Fd' fragment, a Fv fragment, a dAb fragment, a scFv fragment, an isolated CDR region, a dsFv diabody, a single chain antibody, and combinations thereof.

6. A kit comprising:
at least one antibody agent according to claim 1;
a syringe, needle, or applicator for administration of the at least one antibody or fragment thereof that is specific to Dengue virus to a subject; and instructions for use.

7. A method of manufacturing a pharmaceutical composition, the method comprising steps of:
providing an antibody agent according to claim 1; and
formulating the antibody agent with at least one pharmaceutically acceptable carrier or excipient,
so that a pharmaceutical composition is generated.

8. An antibody agent whose heavy chain is or comprises an amino acid sequence as set forth in SEQ ID NO: 21 or whose light chain is or comprises an amino acid sequence as set forth in SEQ ID NO: 22 or both.

9. A composition comprising an immunoglobulin heavy chain of SEQ ID NO: 21.

10. A composition comprising an immunoglobulin light chain of SEQ ID NO: 22.

* * * * *